United States Patent [19]

Semple et al.

[11] Patent Number: 6,011,047
[45] Date of Patent: Jan. 4, 2000

[54] SUBSTITUTED 3-AMINO-2-HYDROXYPHENYLACETAMIDE DERIVATIVES AS ENZYME INHIBITORS

[75] Inventors: Joseph Edward Semple, San Diego; Marguerita S. Lim-Wilby, LaJolla; Terence K. Brunck, San Diego, all of Calif.

[73] Assignee: Corvas International Inc., San Diego, Calif.

[21] Appl. No.: 08/980,114

[22] Filed: Nov. 26, 1997

[51] Int. Cl.$^7$ .......................... A01N 43/40; A01N 47/34; C07D 211/22; C07C 281/02
[52] U.S. Cl. .......................... 514/327; 514/329; 514/590; 514/604; 546/221; 546/231; 564/36; 564/92
[58] Field of Search ..................................... 546/221, 231; 564/36, 92; 514/327, 329, 590, 604

[56] References Cited

U.S. PATENT DOCUMENTS

| | | | |
|---|---|---|---|
| 5,196,404 | 3/1993 | Maraganore et al. | 514/13 |
| 5,371,072 | 12/1994 | Webb et al. | 514/18 |
| 5,492,895 | 2/1996 | Vlasuk et al. | 514/18 |
| 5,534,498 | 7/1996 | Brunck et al. | 514/19 |
| 5,597,804 | 1/1997 | Webb et al. | 514/18 |
| 5,637,599 | 6/1997 | Levy et al. | 514/326 |
| 5,646,165 | 7/1997 | Abelman et al. | 514/315 |
| 5,656,600 | 8/1997 | Abelman et al. | 514/13 |
| 5,656,645 | 8/1997 | Tamura et al. | 514/349 |

FOREIGN PATENT DOCUMENTS

| | | |
|---|---|---|
| 0 293 881 A2 | 12/1988 | European Pat. Off. |
| 0 363 284 A2 | 4/1990 | European Pat. Off. |
| 0 526 877 A2 | 2/1993 | European Pat. Off. |
| 2287 027 | 9/1995 | United Kingdom . |
| 94/13693 | 6/1994 | WIPO . |
| 95/35311 | 12/1995 | WIPO . |
| 95/35313 | 12/1995 | WIPO . |
| 96/19493 | 6/1996 | WIPO . |

OTHER PUBLICATIONS

Database CAPLUS on STN, Acc. No. 1995:348022, Harrington et al., 'Cysteine and methionine linked by carbon pseudopeptides inhibit farnesyl transferase.' Bioorg. Med. Chem. Sett. (1994), 4(23), p. 2775–80, abstract.

Bajusz et al., "Highly Active and Selective Anticoagulants: D–Phe–Pro–Arg–H, a Free Tripeptide Aldehyde Prone to Spontaneous Inactivation, and Its Stable N–Methyl Derivative, D–MePhe–Pro–Arg–H," *J. Med. Chem.* 33(6):1729–1735 (1990).

Bajusz, "Interaction of Trypsin–Like Enzymes with Small Inhibitors," *Symposia Biologica Hungarica* 25:277–298 (1984).

Bajusz et al., "Inhibition of Thrombin and Trypsin by Tripeptide Aldehydes," *Int. J. Peptide Protein Res.* 12:217–221 (1978).

Banner et al., "Crystallographic Analysis at 3.0– Å Resolution of the Binding to Human Thrombin of Four Active Site–Directed Inhibitors," *J. Biol. Chem.* 266:20085–20093 (1991).

Berndt et al., "Ch. 3: Platelet Membrane Proteins: Composition and Receptor Function," *Platelets in Biology and Pathology–2*, Elsevier/North Holland Biomedical Press, pp. 43–75 (1981).

Bock et al., "Isolation of Human Blood Coagulation α–Factor Xa by Soybean Trypsin Inhibitor–Sepharose Chromatography and its Active–Site Titration with Fluorescein Mono–p–guanidinobenzoate" *Arch. Biochem. Biophys.* 273:375–388 (1989).

Buchanan, "The Dakin–West Reaction" *Chem. Soc. Rev.,* 17:91–109 (1988).

Cairns et al., "Antithrombotic Agents in Coronary Artery Disease" *Chest,* 102:456S–481S (1992).

Califf et al., "Restenosis After Coronary Angioplasty: An Overview," *J. Am. Coll. Cardiol.* 17(6):2B–13B (1991).

Chari et al., "Faecal Chymotrypsin Assay in Tropical and Alcoholic Chronic Pancreatitis," *Trop. Gastroenterol.* 11:144–147 (1990).

Chen et al., "Mitogenic Activity of Blood Components. I. Thrombin and Prothrombin (Chick Embryo Fibroblasts/ Growth Factors in Plasma and Serum/Wound Healing)," *Proc. Natl. Acad. Sci. USA* 72(1):131–135 (1975).

Claeson et al., "New Derivatives of p–Guanidino–Phenylalanine as Potent Reversible Inhibitors of Thrombin," *Thromb. Haemstas.,* 50:53 Abstract No. 0147 (1983).

Döring, "The Role of Neutrophil Elastase in Chronic Inflammation," *Am. J. Respir. Crit. Care Med.,* 150:S114–S117 (1994).

Eidt et al., "Thrombin is an Important Mediator of Platelet Aggregation in Stenosed Canine Coronary Arteries with Endothelial Injury," *J. Clin. Invest.,* 84:18–27 (1989).

Esmon, "The Regulation of Natural Anticoagulant Pathways," *Science* 235:1348–1352 (1987).

Fieser et al., "Reagents for Organic Synthesis", p. 46, John Wiley & Sons, New York (1974).

Freidinger, R.M., et al., "Titanium (III) as a Selective Reducing Agent for Nitroarginyl Peptides: Synthesis of Arginine Vasotocin," *J. Org. Chem.,* 43:4800–4803 (1978).

Fujii et al., "New Synthetic Inhibitors of C1r,C1 Esterase, Thrombin, Plasmin, Kallikrein and Trypsin," *Biochimica et Biophysica Acta* 661:342–345 (1981).

(List continued on next page.)

*Primary Examiner*—Gary Geist
*Assistant Examiner*—Brian J. Davis
*Attorney, Agent, or Firm*—Lyon & Lyon LLP

[57] ABSTRACT

The present invention provides peptide aldehydes having a 3-amino-2-hydroxyphyenyl-acetamide group as part of the peptide backbone and an arginine mimic group such as an amidinopiperidine or amidinophenyl tail. These compounds are potent and specific inhibitors of thrombin. Their pharmaceutically salts, pharmaceutically acceptable compositions thereof, and methods of using them as therapeutic agents for disease states in mammals characterized by abnormal thrombosis are also described. Also described are 3-amino-2-hydroxyphenyl-acetamide derivatives having inhibitory activity toward proteases of the trypsin/chymotrypsin class.

28 Claims, 12 Drawing Sheets

OTHER PUBLICATIONS

Geratz et al., "Novel Bis(benzamidino) Compounds with an Aromatic Central Link. Inhibitors of Thrombin, Pancreatic Kallikrein, Trypsin, and Complement," *J. Med. Chem,* 19:634–9 (1976).

Geratz et al., "Structure–Activity Relationships for the Inhibition of Plasmin and Plasminogen Activation by Aromatic Diamidines and a Study of the Effect of Plasma Proteins on the Inhibition Process," *Thromb. Diath. Haemorrh* 29:154–67 (1973).

Geratz et al., "Diamidino –α, ω–diphenoxyalkanes. Structure–Activity Relationships for the Inhibition of Thrombin, Pancreatic Kallikrein, and Trypsin," *J. Med Chem.* 16:970–5 (1973).

Gold et al., "Evidence for a Rebound Coagulation Phenomenon After Cessation of a 4–hour Infusion of a Specific Thrombin Inhibitor in Patients with Unstable Angina Pectoris," *J. Am Coll. Cardiol.,* 21:1039–1047 (1993).

Hirsch, "Drug Therapy," *N. Eng. J. Med.,* 324:1565–1574 (1991).

Hitomi et al., "Inhibitory Effect of a New Synthetic Protease Inhibitor (FUT–175) on the Coagulation System," *Haemostasis,* 15:164–8 (1985).

Jakubowski et al., "Inhibition of Coagulation and Thrombin–Induced Platelet Activities by a Synthetic Dodecapeptide Modeled on the Carboxy–Terminus of Hirudin," *Blood* 75(2):399–406 (1990).

Jang et al., "In Vivo Thrombin Inhibition Enhances and Sustains Arterial Recanalization With Recombinant Tissue–Type Plasminogen Activator," *Circulation Research* 67:1552–1561 (1990).

Jang et al., "Prevention of Platelet–Rich Arterial Thrombosis by Selective Thrombin Inhibition," *Circulation* 81(1):219–225 (1990).

Kasten, "Specimen Collection," *Laboratory Test Handbook,* 2nd Edition, Lexi–Comp Inc. Cleveland pp. 15–20 (Edits. Jacobs, D.S. Et al. 1990).

Kelly et al., "Hirudin Interruption of Heparin–Resistant Arterial Thrombus Formation in Baboons," *Blood* 77(5):1006–1012 (1991).

Kettner et al., "Synthesis of Peptides of Arginine Chloromethyl Ketone. Selective Inactivation of Human Plasma Kallikrein," *Biochemistry,* 17:4778–4781 (1978).

Kettner et al., "Inactivation of Trypsin–Like Enzymes with Peptides of Arginine Chloromethyl Ketone," *Methods in Enzymology* 80:826–842 (1981).

Kettner et al., "The Susceptibility of Urokinase to Affinity Labeling by Peptides of Arginine Chloromethyl Ketone," *Biochim. Biophys. Acta,* 569:31–40 (1979).

Kettner et al., "The Selective Inhibition of Thrombin by Peptides of Boroarginine," *J. Biol. Chem.* 265:18289–18297 (1990).

Kurz et al., "Rat Model of Arterial Thrombosis Induced by Ferric Chloride," *Thrombosis Research* 60:269–280 (1990).

Levin et al., "Specificity of the Thrombin–Induced Release of Tissue Plasminogen Activator From Cultured Human Endothelial Cells," *Thrombosis and Haemostasis* 56(2):115–119 (1986).

Lidon et al., "Initial Experience With a Direct Antithrombin, Hirulog, in Unstable Angina: Anticoagulant, Antithrombotic, and Clinical Effects," *Circulation,* 88:1495–1501 (1993).

Liu et al., "The Region of the Thrombin Receptor Resembling Hirudin Binds to Thrombin and Alters Enzyme Specificity," *J. Biol. Chem.* 266(26):16977–16980 (1991).

Lorand et al., "Activation of the Fibrin Stabilizing Factor of Plasma by Thrombin," *Arch. Biochem. Biophys.* 105:58–67 (1964).

Mann et al., "Surface–Dependent Reactions of Vitamin K–Dependent Enzyme Complexes," *Blood* 76(1):1–16 (1990).

Maraganone et al., Comparison of Anticoagulant and Antithrombotic Activities of Hirulog–1 and Argatroban (MD–805) *Thromb. Haemostas.,* 65: 651 at abstract 17 (1991).

Maraganore et al., "Anticoagulant Activity of Synthetic Hirudin Peptides," *J. Biol. Chem.* 264(15):8692–8698 (1989).

Maraganore et al., "Design and Characterization of Hirulogs: A Novel Class of Bivalent Peptide Inhibitors of Thrombin," *Biochemistry* 29:7095–7101 (1990).

Märki et al., "The Anticoagulant of Antithrombotic Properties of Hirudins," *Thrombosis and Haemostasis* 64(3):344–348 (1990).

Markwardt et al., "Nα–Arylsulfonyl–ω–(4–Amidinophenyl)–α–Aminoalkylcarboxylic Acid Amides—Novel Selective Inhibitors of Thrombin," *Thromb. Res.,* 17:425–31 (1980).

Markwardt, "Hirudin and Derivatives as Anticoagulant Agents," *Thrombosis and Haemostasis* 64(1):141–152 (1991).

Markwardt et al., "Pharmacological Survey of Recombinant Hirudin," *Pharmazie* 43:202–207 (1988).

Markwardt et al., "The Antithrombotic Effect of Symthetic Thrombin Inhibitors," *Thromb. Res.,* 1:243–52 (1972).

Musci et al., "Evidence for Multiple Conformational Changes in the Active Center of Thrombin Induced by Complex Formation with Thrombomodulin: An Analysis Employing Nitroxide Spin–Labels," *Biochemistry* 27:769–773 (1988).

Nemerson et al., "The Biology of Thrombosis," *Ann. Rev. Med.* 33:479–488 (1982).

Ohno et al., [Ethyl p–(6–guanidinohexanoyloxy) benzoate] Methanesulfonate as a Serine Proteinase Inhibitor. I. Inhibition of Trombin and Factor Xa In Vitro, *Thromb. Res.,* 19:579–588 (1980).

Okamoto et al., "Potent Inhibition of Thrombin by the Newly Synthesized Arginine Derivative No. 805. The Importance of Stero–Structure of Its Hydrophobic Carboxamide Portion," *Biochemical and Biophysical Research Communications* 101(2):440–446 (1981).

Pless et al., "Boron Tris (trifluoroacetate) for Removal of Protecting Groups in Peptide Chemistry" *Angew. Chem. Internat. Ed.,* 12:147–148 (1973).

Prins et al., "Heparin as Adjunctive Treatment After Thrombolytic Therapy for Acute Myocardial Infarction," *American Journal of Cardiology* 67:3A–11A (1991).

Rabinovitch, "Elastase and Cell Matrix Interactions in the Pathobiology of Vascular Disease," *Acta Paediatrica Japonica,* 37:657–666 (1995).

Riedel et al., "Limitations of Faecal Chymotrypsin as a Screening Test for Chronic Pancreatis" *Gut.* 32:321–324 (1991).

Ross, "Ch. 17—Myocardial Infarction: Adjunctive Antithrombotic Therapy to Thrombolysis," in *Thrombosis in Cardiovascular Disorders,* edited by Fuster and Verstraete, W.B. Saunders Company, Philadelphia, pp. 327–341 (1991).

Ross, "The Pathogenesis of Atherosclerosis—An Update," *New England J. Med.* 314(8):488–500 (1986).

Rydel et al., "The Structure of a Complex of Recombinant Hirudin and Human α–Thrombin," *Science* 249:277–280 (1990).

Saito, "Normal Hemostatic Mechanisms," in *Disorders of Hemostasis,* edited by Ratnoff and Forbes, Grune & Stratton, Inc., pp. 27–29 (1984).

Sarembock et al., "Effectiveness of Recombinant Desulphatohirudin in Reducing Restenosis After Balloon Angio-Plasty of Atherosclerotic Femoral Arteries in Rabbits," *Circulation* 84:232–243 (1991).

Sharma et al., "Usefulness and Tolerability of Hirulog, a Direct Thrombin–Inhibitor, in Unstable Angina Pectoris," *Am. J. Cardiol.,* 72:1357–1360 (1993).

Shuman, "Thrombin–Cellular Interactions," *Ann. NY Acad. Sci.* 485:228–239 (1986).

Skrzypczak–Jankun et al., "X–Ray Crystallographic Structures of the Hirugen: Thrombin and Hirulog: Thrombin Complexes at 2.2 a Resolution," *Thromb. Haemostas.* 65:830 at abstract 507 (1991).

Sturzebecher et al., "Cyclic Amides of Nα–Arylsulfonylaminoacylated 4–Amidinophenylalanine–Tight Binding Inhibitors of Thrombin," *Thromb. Res.,* 29:635–42 (1983).

Tans et al., "Comparison of Anticoagulant and Procoagulant Activities of Stimulated Platelets and Platelet–Derived Microparticles," *Blood* 77(12):2641–2648 (1991).

Teitel et al., "Protection of Factor Xa from Neutralization by the Heparin–antithrombin Complex," *J. Clin. Invest.* 71:1383–1391 (1983).

Ueda et al., "The Synthesis of Arginylfluoroalkanes, Their Inhibition of Trypsin and Blood–Coagulation Serine Proteinases and their Anticoagulant Activity," *Biochem. J.,* 265: 539–545 (1990).

Walsmann et al., "Synthetische Inhibitoren der Serinproteinasen" *Acta. Biol. Med. Germ.,* 35:K1–8 (1976).

Walz et al., "Thrombin–Elicited Contractile Responses of Aortic Smooth Muscle (42211)," *Proceedings of the Society for Experimental Biology and Medicine* 180:518–526 (1985).

Williams et al., "[17] The Kinetics of Reversible Tight–Binding Inhibition," *Methods in Enzymology,* 63:437–467 (1979).

Wityak et al., "Synthesis of Thrombin Inhibitor DuP 714," *J. Org. Chem.,* 60:3717–3722 (1995).

SUBSTITUTED 3-AMINO-2-HYDROXYPHENYLACETAMIDE DERIVATIVES AS ENZYME INHIBITORS

TECHNICAL FIELD

In one aspect, the present invention relates to compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., *Ann. Rev. Med.*, 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", *Disorders of Hemostasis*, pp. 27–29, Grune & Stratton, Inc. (O. D. Ratnoff, M. D. and C. D. Forbes, M. D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", *Blood*, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", *J. Clin. Invest.*, 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., *Arch. Biochem. Biophys.*, 105: 58 (1964). Beyond its direct role in the formation and stabilization of fibrin rich clots, the enzyme has been reported to have profound bioregulatory effects on a number of cellular components within the vasculature and blood. Shuman, M. A., *Ann. NY Acad. Sci.*, 405: 349 (1986).

It is believed that thrombin is the most potent agonist of platelet activation, and it has been demonstrated to be the primary pathophysiologic-mediator of platelet-dependent arterial thrombus formation. Edit, J. F. et al., *J. Clin. Invest.*, 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., *Platelets in Biology and Pathology*, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., *Blood*, 77: 2641 (1991). This positive feedback process results in the local generation of large concentrations of thrombin within the vicinity of the thrombus which supports further thrombus growth and extension. Mann, K. G. et al., *Blood*, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., *Biochemistry*, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., *Science*, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., *Proc. Natl. Acad. Sci. USA*, 72: 131 (1975). The direct interaction of thrombin with vascular smooth muscle also results in vasoconstriction. Walz, D. A. et al., *Proc. Soc. Exel. Biol. Med.*, 180: 518 (1985). Thrombin acts as a direct secretagogue inducing the release of a number of bioactive substances from vascular endothelial cells including tissue plasminogen activator. Levin, E. G. et al., *Thromb. Haemost.*, 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., *N. Enal. J. Med.*, 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., *Thrombosis in Cardiovascular Disorder*, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., *J. Am. Coll. Cardiol.*, 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., *J. Am. Coll. Cardiol.*, 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

```
P4  P3  P2  P1  P1'
Gly-Gly-Val-Arg/Gly Fibrinogen α Chain
[SEQ. ID. NO. 1]

Phe-Ser-Ala-Arg/Gly Fibrinogen β Chain
[SEQ. ID. NO. 2]
```

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., *Symposia Biologica Hungarica*, 25: 277 (1984), Bajusz, S. et al, *J. Med. Chem.*, 33: 1729 (1990) and Bajusz, S. et al., Int. *J. Peotide Protein Res*. 12: 217 (1970); Kettner, C. and Shaw, E., *Methods Enzymol.*, 80: 826 (1987), Kettner, C. et al., EP 293,881 (published Dec. 7, 1988), Kettner, C., et al., *J. Biol. Chem.*, 265: 18209 (1990). These molecules have been reported to be potent anticoagulants in the prevention of platelet-rich arterial thrombosis. Kelly, A. B. et al., *Thromb. Haemostas.*, 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-L-argininy]-2-piperdinecarboxylic acid), is also reported to bind directly to the active site of thrombin and has been thought to be the most potent and selective compound in the class of non-peptidyl inhibitors of this enzyme. Okamoto, S. et al., *Biochem. Biophys. Res. Commun.*, 101: 440 (1981). Argatroban has been reported to be a potent antithrombotic agent in several experimental models of acute arterial thrombosis. Jang, I. K. et al., in both *Circulation*, 81: 219 (1990) and *Circ. Res.*, 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., *Thromb. Haemostas.*, 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., *Thromb. Haemostas.*, 64: 344 (1990). It has been reported to inhibit thrombin by binding to both its anion-binding exo-site and to its catalytic active site which are distinct and physically distant from each other. Rydel, T. J. et al., *Science*, 249:277 (1990). Hirudin has been reported to be a potent antithrombotic agent in vivo. Markwardt, F. et al., *Pharmazie*, 43: 202 (1988); Kelly, A. B. et al., *Blood*, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., *Circulation*, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., *J. Biol. Chem.*, 264: 8692 (1989); Naski, M. C. et al., *J. Biol. Chem.*, 265: 13484 (1990). The region of hirudin represented by hirugen has been reported, as according to by x-ray crystallographic analysis, to bind directly to the exo site of thrombin. Skrzypczak-Jankun, E. et al., *Thromb. Haemostas.*, 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, L. W. et al., *J. Biol. Chem.*, 266:16977 (1991). Hirugen also is reported to block thrombin-mediated platelet aggregation. Jakubowski, J. A. and Maraganore, J. M., *Blood*, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., *Biochemistry*, 29: 7095 (1990). The hirulogs have been reported to be an effective antithrombotic agents in preventing both fibrin-rich and platelet-rich thrombosis. Maraganone, J. M. et al., *Thromb. Haemostas.*, 65: 651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., *Thromb. Res.*, 1:243–52 (1972). Other benzamidine-derived structures which have been reported to inhibit thrombin include the cylic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., *Thromb. Res.*, 17:425–31 (1980). Moreover, derivatives of 4-amidinophenylalanine whose α-amino group is linked to the arylsulfonyl residue via an ω-aminoalkylcarboxylic acid as spacer have also been assessed for their inhibitory effect. Among these $N^\alpha$-(2-naphthylsulphonylglycyl)-4-amidino-phenylalanine piperidide (α-NAPAP) has been reported to possess an affinity for thrombin ($K_i=6\times10^{-9}$ M). Banner et al., *J. Biol. Chem.*, 266:20085 (1991) and Sturzebecher et al., *Thromb. Res.*, 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et. al., *Thromb. Diath. Haemorrh.*, 29:154–67 (1973); Geratz et. al., *J. Med. Chem.*, 16:970–5 (1973); Geratz et. al., *J. Med. Chem.*, 19:634–9 (1976); Walsmann et. al., *Acta Biol. Med. Germ.*, 35: K1–8 (1976); and Hauptmann et. al., *Acta Biol. Med. Germ.*, 35:635–44 (1976).

Certain amidino-bearing aromatic ring structures such a β-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., *Biochim. Biophys. Acta*, 661:342–5 (1981); and Hitomi et. al., *Haemostasis*, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et. al., *Thromb. Haemostas.*, 50:53 (1983). Another compound, [ethyl p-(6-guanidinohexanoyloxy) benzoate] methane sulfonate (FOY) was reported to be a non-selective competitive inhibitor of thrombin. Ohno et al., *Thromb. Res.*, 19:579–588 (1980).

Certain compounds having inhibitory activity toward serine proteases, including thrombin, factor Xa, and trypsin, are disclosed within the following commonly assigned United States patents or published PCT applications: U.S. Pat. Nos. 5,371,072; 5,492,895; 5,534,498; 5,597,804; 5,637,599; 5,646,165; 5,656,600; 5,656,645; WO 94/13693; WO 95/35311; WO 95/35313; WO 96/19493.

SUMMARY OF THE INVENTION

Novel compounds of the present invention include compounds of the formula (I):

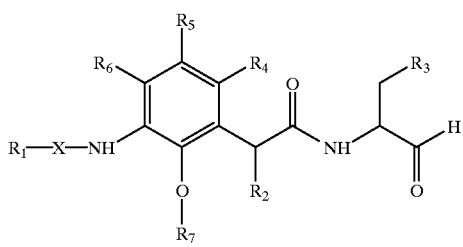

wherein
- (a) X is selected from the group consisting of —S(O)$_2$—, —N(R')—S(O)$_2$—, —C(=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NHR', OR', R', or SR';
- (b) R$_1$ is selected from the group consisting of:
  - (1) alkyl of 1 to about 12 carbon atoms,
  - (2) alkyl of 1 to about 3 carbon atoms substituted with cycloalkyl of about 5 to about 8 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (3) cycloalkyl of 3 to about 15 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, and which is optionally substituted on the ring carbons with hydroxyl, amino, guanidino, amidino, C$_1$ to C$_3$ alkyl, C$_1$ to C$_3$ alkoxy, or —CO$_2$R',
  - (5) heterocyclo of 4 to about 10 ring atoms with the ring atoms selected from carbon and heteroatoms, wherein the heteroatoms are selected from the group consisting of oxygen, nitrogen, and S(O)$_i$ and which is optionally substituted on the ring carbons with hydroxyl, amino, guanidino, amidino, C$_1$ to C$_3$ alkyl or alkoxy, or —CO$_2$R',
  - (6) alkenyl of 2 to about 6 carbon atoms which is optionally substituted with cycloalkyl of about 3 to about 8 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (7) aryl of about 6 to about 14 carbon atoms which is optionally mono-, di- or tri-substituted with Y$_1$, Y$_2$, and/or Y$_3$,
  - (8) heteroaryl of about 5 to about 14 ring atoms with the ring atoms selected from carbon and heteroatoms, wherein the heteroatoms are selected from oxygen, nitrogen, and S(O)$_i$, and which is optionally mono-, di- or tri-substituted on the ring carbons with Y$_1$, Y$_2$, and/or Y$_3$,
  - (9) aralkyl of about 7 to about 15 carbon atoms which is optionally substituted on the alkyl chain with hydroxy or halogen which is optionally mono-, di-, or tri-substituted on the aryl ring with Y$_1$, Y$_2$, and/or Y$_3$,
  - (10) heteroaralkyl of 5 to about 14 ring atoms with the ring atoms selected from carbon and heteroatoms, wherein the heteroatoms are selected from oxygen, nitrogen, and S(O)$_i$, which is optionally substituted on the alkyl chain with hydroxy or halogen and which is optionally mono-, di- or tri-substituted on the ring with Y$_1$, Y$_2$, and/or Y$_3$,
  - (11) aralkenyl of about 8 to about 16 carbon atoms having 5 to about 14 ring atoms which is optionally mono-, di-, or tri-substituted on the aryl ring with Y$_1$, Y$_2$, and/or Y$_3$,
  - (12) heteroaralkenyl of 5 to about 14 ring atoms with the ring atoms selected from carbon and heteroatoms, wherein the heteroatoms are selected from oxygen, nitrogen, and S(O)$_i$, and which is optionally mono-, di- or tri-substituted on the ring with Y$_1$, Y$_2$, and/or Y$_3$,

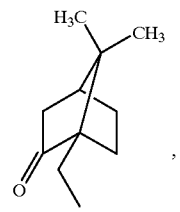

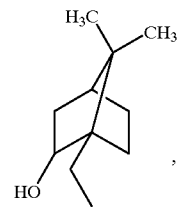

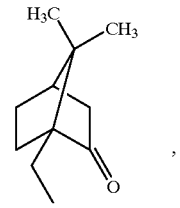

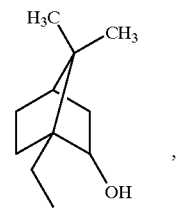

- (17) perfluoroalkyl of 1 to about 12 carbon atoms,
- (18) perfluoroaryl of about 6 to about 14 carbon atoms,
- (19) perfluoroaralkyl of about 7 to about 15 carbon atoms,
- (20) hydrogen, and (21)

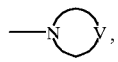

wherein

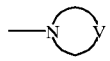

is a 5 to 7 membered heterocyclic ring having 3 to 6 ring carbon atoms, where V is —CH$_2$—, —O—, —S(=O)—, —S(O)$_2$— or —S—, wherein Y$_1$, Y$_2$, and Y$_3$ are
  (i) independently selected from the group consisting of hydrogen, halogen, cyano, nitro, tetrazolyl, amino, guanidino, amidino, methylamino, methylguanidino, —CF$_3$, —CF$_2$CF$_3$, —CF$_2$H, —CH(CF$_3$)$_2$, —C(OH)(CF$_3$)$_2$, —OCF$_3$, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NZ$_1$Z$_2$, —C(O)OH, —C(O)NH$_2$, —C(O)NHZ$_1$, —C(O)NZ$_1$Z$_2$, —C(O)OZ$_1$, —P(O)$_3$H, —P(O)$_3$H$_2$, —PH(O)OH, —P(O)$_3$(Z$_1$)$_2$, —S(O)$_3$H, —S(O)$_m$Z$_1$, —Z$_1$, —OZ$_1$, —OH, —NH$_2$, —NHZ$_1$, and —NZ$_1$Z$_2$, wherein m is 0, 1 or 2, and Z$_1$ and Z$_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
  (ii) Y$_1$ and Y$_2$ are selected together to be —O[C(Z$^3$)(Z$^4$)]$_q$O—, wherein q is an integer from 1 to 4 and Z$_3$ and Z4 are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms;
(c) R$_2$ is selected from the group consisting of hydrogen, alkyl of 1 to about 4 carbon atoms, and alkenyl of about 2 to about 4 carbon atoms;
(d) R$_3$ is selected from the group consisting of

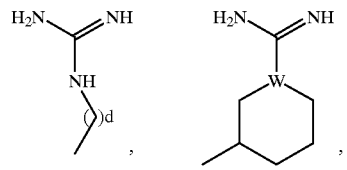

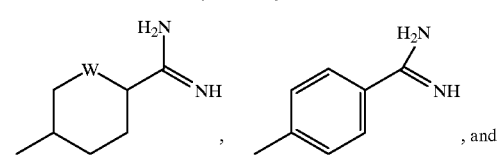

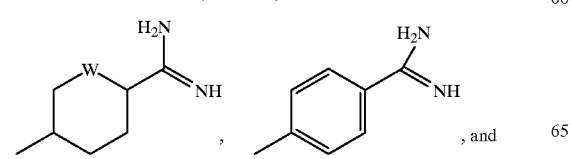, and

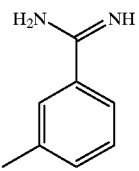

where d is an integer from 0 to 5 and W is —N— or —CH—;
(e) R$_4$ is selected from the group consisting of
  (i) —R$_1$, —OR$_1$, —NHR$_1$, —S(O)$_n$R$_1$, wherein n is 0, 1 or 2, and R$_1$ is as defined above, with the proviso that R$_1$ is not a camphor derivative or

heterocycle,
  (ii) —CF$_3$, —CF$_2$H, —OCF$_3$, or —OCF$_2$H,
  (iii) halogen,
  (iv) alkyl of 1 to 6 carbon atoms substituted with Z$_5$, wherein Z$_5$ is selected from the group consisting of hydrogen, —OH, —OR$_8$, —CH$_3$, halogen, —C(O)OH, —C(O)OR$_8$ and —S(O)$_p$R$_8$, wherein R$_8$ is alkyl of 1 to about 6 carbon atoms, and p is 0, 1 or 2
  (v) alkyl of 1 to 3 carbon atoms substituted with cycloalkyl of 3 to 5 carbon atoms,
  (vi) alkenyl of about 3 to about 6 carbon atoms,
  (vii) cycloalkyl of about 3 to about 10 carbon atoms,
  (viii) heteroaryl of about 5 to about 10 ring atoms having 1 to about 9 ring carbon atoms and the remainder of the ring atoms heteroatoms selected from oxygen, sulfur and nitrogen, and
  (ix) heteroaralkyl of about 5 to about 10 ring atoms having about 2 to about 15 carbon atoms which include 1 to about 9 ring carbon atoms and the remainder of the ring atoms heteroatoms selected from oxygen, sulfur and nitrogen;
(f) R$_5$ is selected from the group consisting of
  (i) —R$_1$, —OR$_1$, —NHR$_1$, —S(O)$_n$R$_1$, wherein R$_1$ is as defined above, with the proviso that R$_1$ is not a camphor derivative or

heterocycle,
  (ii) —CF$_3$, —CF$_2$H, —OCF$_3$, or —OCF$_2$H, and
  (iii) halogen;
(g) R$_6$ is selected from the group consisting of
  (i) R$_1$, —OR$_1$, —NHR$_1$, —S(O)$_n$R$_1$, wherein R$_1$ is as defined above, with the proviso that R$_1$ is not a camphor derivative or

heterocycle,
  (ii) —CF$_3$, —CF$_2$H, —OCF$_3$, or —OCF$_2$H,
  (iii) halogen,
  (iv) alkyl of 1 to about 12 carbon atoms substituted with Z$_6$, wherein Z$_6$ is selected from the group consisting of hydrogen, hydroxy, halogen, —OR$_9$, —NHR$_9$, —C(O)OH, —C(O)OR$_9$, and —S(O)$_p$R$_9$, wherein R$_9$ is alkyl of 1 to about 12 carbon atoms, aryl of about 6 to about 10 carbon atoms, aralkyl of about 7 to about 12 carbon atoms, heteroaryl of about 5 to about 10 ring atoms having 1 to about 9 ring carbon atoms and the remainder of the ring atoms heteroatoms selected from oxygen, sulfur and nitrogen, which is optionally mono-, di- or tri-substituted in the ring carbons with Y$_1$, Y$_2$ and/or Y$_3$; or heteroaralkyl of about 5 to about 10 ring atoms having 1 to about 9 ring carbon atoms and the remainder of the ring atoms heteroatoms selected from oxygen, sulfur and nitrogen, and which is optionally mono-, di- or tri-substituted on the ring carbons with Y$_1$, Y$_2$ and/or Y$_3$;

(v) alkyl of 1 to about 3 carbon atoms substituted with cycloalkyl of about 3 to about 8 carbon atoms;

(vi) alkenyl of 2 to about 6 carbon atoms which is optionally substituted with cycloalkyl of about 3 to about 8 carbon atoms, aryl of about 5 to about 10 carbon atoms or heteroaryl of of about 5 to about 10 ring atoms having 1 to about 9 ring carbon atoms, (vii) aralkyl of about 7 to about 15 carbon atoms which is optionally substituted on the alkyl chain with hydroxy or halogen, and optionally mono-, di- or tri-substituted on the aryl ring with Y$_1$, Y$_2$ and/or Y$_3$, (viii) heteroaralkyl of about 5 to about 10 ring atoms having 1 to about 9 ring carbon atoms and the remainder of the ring atoms heteroatoms selected from oxygen, sulfur and nitrogen, which is optionally substituted on the alkyl chain with hydroxy or halogen, and optionally mono-, di- or tri-substituted on the ring carbons with Y$_1$, Y$_2$ and/or Y$_3$, (ix) aralkenyl of 6 to about 15 carbon atoms which is optionally mono-, di- or tri-substituted on the aryl ring with with Y$_1$, Y$_2$ and/or Y$_3$, and (x) heteroaralkenyl of about 5 to about 10 ring atoms having 1 to 9 ring carbon atoms and having the remainder of the ring atoms heteroatoms selected from oxygen, sulfur and nitrogen, which is optionally mono-, di- or tri-substituted on the ring carbons with Y$_1$, Y$_2$ and/or Y$_3$, as defined above; and (h) R$_7$ is selected from the group consisting of
(i) R$_1$, wherein R$_1$ is as defined above, with the proviso that R$_1$ is not a camphor derivative or

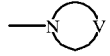

heterocycle,
(ii) —CF$_3$, or —CF$_2$H,
(iii) alkyl of 1 to about 10 carbon atoms, optionally substituted with —CH$_2$OR$_{10}$, —CO$_2$R$_{10}$, —SO$_2$R$_{10}$, or —CONR$_{10}$R$_{11}$,
(iv) alkenyl of about 3 to about 10 carbon atoms, optionally substituted with —CH$_2$OR$_{10}$, —CO$_2$R$_{10}$, —SO$_2$R$_{10}$, —CONR$_{10}$R$_{11}$,
(v) cycloalkyl of 3 to about 10 carbon atoms, optionally substituted with —CH$_2$OR$_{10}$, —CO$_2$R$_{10}$, —SO$_2$R$_{10}$, —CONR$_{10}$R$_{11}$,
(vi) heteroaryl of about 5 to about 10 ring atoms having about 1 to about 9 carbon atoms, optionally substituted with —CH$_2$OR$_{10}$, —CO$_2$R$_{10}$, —SO$_2$R$_{10}$, —CONR$_{10}$R$_{11}$, and
(vii) alkyl of 1 to about 3 carbon atoms substituted with heteroaryl of about 5 to about 10 ring atoms having about 1 to about 9 carbon atoms, optionally substituted with —CH$_2$OR$_{10}$, —CO$_2$R$_{10}$, —SO$_2$R$_{10}$, —CONR$_{10}$R$_{11}$, and wherein each of R$_{10}$ and R$_{11}$ is independently selected and is alkyl of 1 to about 4 carbon atoms or hydrogen; or pharmaceutically acceptable salts thereof.

Among other factors, the present invention is based on our finding that these novel compounds are active as selective inhibitors of thrombin in vivo and in vitro. Furthermore, certain of the preferred compounds of the present invention have been found to exhibit advantageous selectivity in that they are potent inhibitors of thrombin, but are much less active and much less potent in inhibiting plasmin and trypsin. Certain compounds of the present invention may also have broader serine protease inhibitory activity.

According to an alternate aspect of the present invention, also provided are compounds of formula (II) which have inhibitory activity towards proteases of the trypsin/chymotrypsin class. This aspect of the invention is directoward to compounds of formula (II):

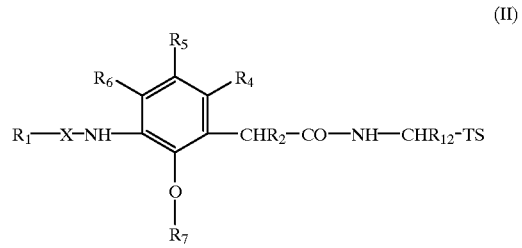

(II)

wherein a substituted phenol or phenyl ether is present in the compound in place of the amide bond of an inhibitor that makes hydrogen bonds to amino acid 216 in the trypsin/chymotrypsin class of serine proteases. Thus, according to this aspect of the present invention, provided are compounds of formula (II), wherein X, R$_1$, R$_2$, R$_4$, R$_5$, R$_6$, and R$_7$ are as defined hereinabove in connection with formula (I), and (a) R$_{12}$ is selected from the group consisting of
(i) alkyl of 1 to about 12 carbon atoms optionally substituted with amino, amidino, or guanidino,
(ii) aralkyl of 7 to about 15 carbon atoms which is optionally substituted on a ring carbon with amino, amidino or guanidino,
(iii) aryl of 6 to about 14 carbon atoms which is optionally substituted on a ring carbon with amino, amidino, or guanidino, and
(iv) heteroaralkyl of 5 to about 14 ring atoms having about 1 to about 13 ring carbon atoms and the remainder of the ring atoms heteroatoms selected from oxygen, nitrogen and sulfur which is optionally substituted on a ring carbon with amino, amidino or guanidino; and (b) TS is selected from the group consisting of
(i) —CHO,
(ii) —C(O)CF$_3$,
(iii) —C(O)CF$_2$CF$_3$,
(iv) —C(O)—C(O)—NHR$_{13}$,
(v) —C(O)—C(O)$_2$R$_{13}$,
(vi) —C(O)—C(O)—NR$_{13}$R$_{14}$,
(vii) —B(OR$_{13}$)(OR$_{14}$)
(viii) —C(O)CH$_2$Cl, and
(ix) —C(O)R$_{15}$;

wherein R$_{13}$ and R$_{14}$ are independently selected from hydrogen lower alkyl of 1 to about 6 carbon atoms, cycloalkyl of 3 to about 10 carbon atoms, aralkyl of 7 to about 15 carbon atoms, and heteroaralkyl of about 5 to about 10 ring atoms having about 2 to about 15 carbon atoms which include 1 to about 9 ring carbon atoms and the remainder of the ring atoms heteroatoms selected from oxygen, nitrogen and sulfur, and $R_{15}$ is selected from aryl of 6 to about 14 carbon atoms and heteroaryl of 5 to about 14 ring atoms having 1 to about 13 ring carbon atoms and the remainder of the ring atoms selected from oxygen, nitrogen and sulfur. In the case where TS is (vii), additionally —$OR_{13}$ and —$OR_{14}$ may be taken together to be —$O[C(Z_3)(Z_4)]_qO$— wherein $Z_3$, $Z_4$ and q are as defined in connection with formula(I). Also included are pharmaceutically acceptable salts of the compounds of formula (II).

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of formula (I) for the prevention of or treating of thrombosis in a mammal suspected of having a condition of abnormal thrombosis, which comprises administering to said mammal a therapeutically effective amount of a compound of the present invention or pharmaceutical composition comprising such a compound.

Definitions

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, phenethyl, and the like, all of which may be optionally substituted.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to natural amino acids, unnatural amino acids, and amino acid analogs, all in their D and L stereoisomers if their structure allow such stereoisomeric. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

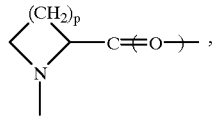

(2)

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to naphthyl, more preferably 1- or 2-naphthyl, substituted by $Y_1$, $Y_2$ and/or $Y_3$ as defined in connection with formula (I) hereinabove.

"Cycloalkenyl" refers to a cyclic alkenyl group. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to $CH_2$.

The term "halogen" refers to fluorine, chlorine, bromine and iodine.

"Heteroaralkenyl" refers to an alkenyl group substitued with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkenyl group has from 2 to about 6 carbon of atoms.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from 1 to about 6 carbon atoms.

"Heteroaryl" refers to aryl groups having from 1 to 9 ring carbon atoms and the remainder of the ring atoms heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, $S(O)_i$, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from 1 to about 6 carbon atoms.

The term "lower" referred to herein in connection with organic radicals or groups defines such radicals or groups with one and up to and including 5 carbon atoms, preferably up to and including 4 carbon atoms, and advantageously one or two carbon atoms. Such radicals or groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroaryl alkyl" refers an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "Arg-al" refers to the residue of L-argininal which has the formula:

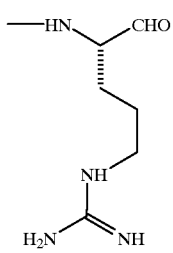

The term "Arg-ol" refers to the residue of L-argininol which has the formula:

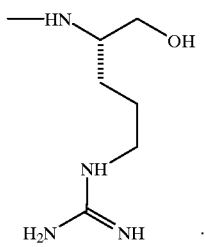

"(S)-N$^g$-nitroargininol hydrochloride" refers to the compound which has the formula:

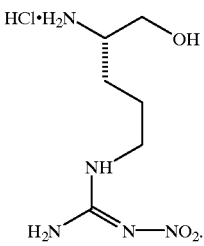

"N-alpha-t-butoxycarbonyl-N$^g$-nitro-L-arginine" refers to the compound which has the formula:

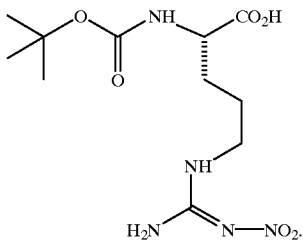

"Bn" refers to benzyl.
"Boc" refers to t-butoxycarbonyl.
"BzlSO$_2$" refers to benzylsulfonyl.
"Cbz" or "CBz" refers to benzyloxycarbonyl.
"DCA" refers to dichloroacetic acid.
"DCC" refers to N,N'-dicyclohexylcarbodiimide.
"DMF" refers to N, N-dimethylformamide.
"DMSO" refers to dimethyl sulfoxide.
"DMAP" refers to 4-N,N-dimethylaminopyridine.
"EDC" refers to 1-ethyl-3-(3-dimethylamino-propyl) carbodiimide hydrochloride salt.
"Et$_3$N" refers to triethylamine.
"EtOH" refers to ethanol.
"HBTU" refers to 2-(1H-benzotriazol-1-yl)-1,1,3,3-tetramethyluronium hexafluorophosphate.

"HCl" refers to hydrochloric acid.
"HOAc" refers to acetic acid.
"HPLC" refers to high pressure liquid chromatography.
"HOBt" refers to 1-hydroxybenzotriazole monohydrate.
"i-BuOCOCl" refers to isobutylchloroformate.
"LiAlH$_4$" refers to lithium aluminum hydride.
"LiAlH$_2$(OEt)$_2$" refers to lithium aluminum dihydride diethoxide.
"Me" refers to methyl.
"NMM" refers to N-methylmorpholine.
"PhB(OH)$_2$" refers to phenylboronic acid.
"THF" refers to tetrahydrofuran.
"TLC" refers to thin layer chromatography.

DETAILED DESCRIPTION OF THE INVENTION

1. Preferred Novel Compounds

Figure 1:
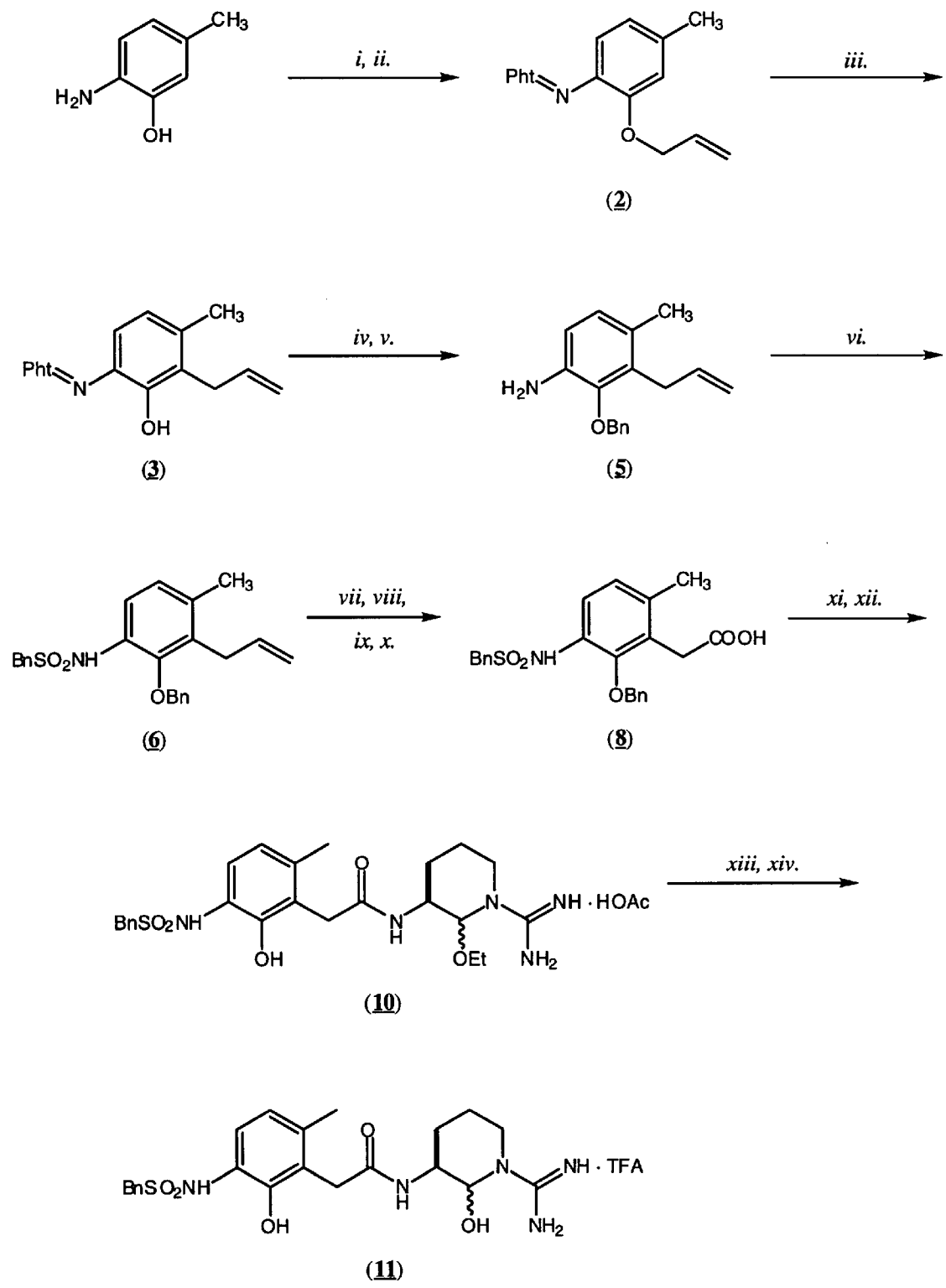
FIG. 1 provides a synthetic scheme for compound 11, which is further detailed in Examples 1 to 11. In this figure, the steps "i" through "xiv" are defined as follows: In the synthesis of (2) from 6-amino-m-cresol: i) phthalic anhydride, acetic acid, reflux to give a 95% yield of (1), N-(2-hydroxy-4-methylphenyl)phthalimide); and 2. ii) allyl bromide, K$_2$CO$_3$, acetonitrile, reflux to give 97% yield of (2). In the synthesis of (3) from (2): iii) N,N-dimethylaniline, 185° C., about two hours, to give a 95% yield of (3). In the synthesis of (5) from (3): iv) benzylbromide, K$_2$CO$_3$, acetonitrile, reflux to give an 81% yield of (4), the benzyl ether derivative of (3); and v) hydrazine, ethanol, reflux to give a 97% yield of (5). In the synthesis of (6) from (5): α-toluene sulfonyl chloride, 4-methylmorpholine, acetonitrile, temperature 0° C., then warming to room termperature to give 99% yield of (6). In the synthesis of (8) from (6): vii) ozone gas, methanol, −78° C.; viii) dimethylsulfide, −78° C., then warming to room temperature; ix) 1N HCl, acetone, room temperature then reflux to give an intermediate phenylacetaldehyde derivative (7); and x) Jones' oxidation, acetone, 0° C., then warming to room temperature to give approximately quantitative yield of (8). In the synthesis of (10) from (8): xi) hydrochloride salt of N$^g$-nitro-L-arginial ethyl cyclol, EDC, 1-hydroxybenzotriazole hydrate, N,N-diisopropylethylamine, acetonitrile, to give a 69% yield of (9); and xii) H$_2$, Pd/C catalyst, 55 PSI, ethanol, acetic acid, water to give a 89% yield of (10). In the synthesis of (11) from (10): xiii) 5N HClO$_4$, 0° C., 60 minutes; and xiv) HPLC, to give a 62% yield of (11).

Novel compounds of the present invention include compounds of the formula (I):

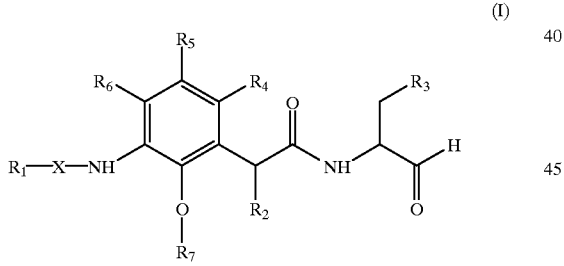

(I)

wherein
- (a) X is selected from the group consisting of —S(O)2—, —N(R')—S(O)$_2$—, —C(=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NHR', OR', R', or SR';
- (b) R$_1$ is selected from the group consisting of:
  - (1) alkyl of 1 to about 12 carbon atoms,
  - (2) alkyl of 1 to about 3 carbon atoms substituted with cycloalkyl of about 5 to about 8 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (3) cycloalkyl of 3 to about 15 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, and which is optionally substituted on the ring carbons with hydroxyl, amino, guanidino, amidino, C$_1$ to C$_3$ alkyl, C$_1$ to C$_3$ alkoxy, or —CO$_2$R',
  - (5) heterocyclo of 4 to about 10 ring atoms with the ring atoms selected from carbon and heteroatoms, wherein the heteroatoms are selected from the group consisting of oxygen, nitrogen, and S(O)$_i$ and which is optionally substituted on the ring carbons with hydroxyl, amino, guanidino, amidino, C$_1$ to C$_3$ alkyl or alkoxy, or —CO$_2$R',
  - (6) alkenyl of 2 to about 6 carbon atoms which is optionally substituted with cycloalkyl of about 5 to about 8 carbon atoms, which optionally is substituted on the ring carbons with hydroxyl, amino, guanidino, amidino, C$_1$ to C$_3$ alkyl, C$_1$ to C$_3$ alkoxy, or —CO$_2$R',
  - (7) aryl of about 6 to about 14 carbon atoms which is optionally mono-, di- or tri-substituted with Y$_1$, Y$_2$, and/or Y$_3$, respectively,
  - (8) heteroaryl of 5 to about 14 ring atoms with the ring atoms selected from carbon and heteroatoms, wherein the heteroatoms are selected from oxygen, nitrogen, and S(O)$_i$, and which is optionally mono-, di- or tri-substituted on the ring carbons with Y$_1$, Y$_2$, and/or Y$_3$,
  - (9) aralkyl of about 7 to about 15 carbon atoms having 6 to about 14 ring atoms which is optionally substituted on the alkyl chain with hydroxy or halogen and which is optionally mono-, di-, or tri-substituted on the aryl ring with Y$_1$, Y$_2$, and/or Y$_3$,
  - (10) heteroaralkyl of 5 to about 14 ring atoms with the ring atoms selected from carbon and heteroatoms, wherein the heteroatoms are selected from oxygen, nitrogen, and S(O)$_i$, which is optionally substituted on the alkyl chain with hydroxy or halogen and which is optionally mono-, di- or tri-substituted on the ring with Y$_1$, Y$_2$, and/or Y$_3$,
  - (11) aralkenyl of about 8 to about 16 carbon atoms having 6 to about 14 ring atoms which is optionally mono-, di-, or tri-substituted on the aryl ring with Y$_1$, Y$_2$, and/or Y$_3$,
  - (12) heteroaralkenyl of 5 to about 14 ring atoms with the ring atoms selected from carbon and heteroatoms, wherein the heteroatoms are selected from oxygen, nitrogen, and S(O)$_i$, and which is optionally mono-, di- or tri-substituted on the ring with Y$_1$, Y$_2$, and/or Y$_3$, (13)

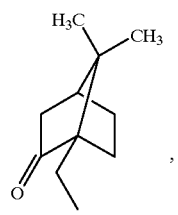

,

-continued

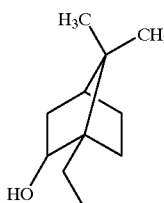
(14)

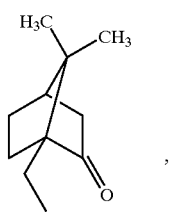
(15)

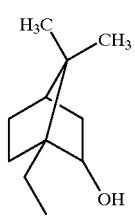
(16)

(17) perfluoroalkyl of 1 to about 12 carbon atoms,
(18) perfluoroaralkyl of about 6 to about 14 carbon atoms,
(19) perfluoroaralkyl of about 7 to about 15 carbon atoms,
(20) hydrogen, and
(21)

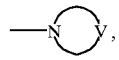

wherein

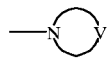

is a 5 to 7 membered heterocyclic ring having 3 to 6 ring carbon atoms, where V is —CH$_2$—, —O—, —S(=O)—, —S(O)$_2$— or —S—, and wherein Y$_1$, Y$_2$, and Y$_3$ are
(i) independently selected from the group consisting of hydrogen, halogen, cyano, nitro, tetrazolyl, amino, guanidino, amidino, methylamino, methylguanidino, —CF$_3$, —CF$_2$CF$_3$, —CF$_2$H, —CH(CF$_3$)$_2$, —C(OH)(CF$_3$)$_2$, —OCF$_3$, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NZ$_1$Z$_2$, —C(O)OH, —C(O)NH$_2$, —C(O)NHZ$_1$, —C(O)NZ$_1$Z$_2$, —C(O)OZ$_1$, —P(O)$_3$H, —P(O)$_3$H$_2$, —PH(O)OH, —P(O)$_3$(Z$_1$)$_2$, —S(O)$_3$H , —S(O)$_m$Z$_1$, —Z$_1$, —OZ$_1$, —OH, —NH$_2$, —NHZ$_1$, and —NZ$_1$Z$_2$, wherein m is 0, 1 or 2, and Z$_1$ and Z$_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) Y$_1$ and Y$_2$ are selected together to be —O[C(Z$_3$)(Z$^4$)]$_q$O—, wherein q is an integer from 1 to 4 and Z$_3$ and Z$_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms;
(c) R$_2$ is selected from the group consisting of hydrogen, alkyl of 1 to about 4 carbon atoms, and alkenyl of about 2 to about 4 carbon atoms;
(d) R$_3$ is selected from the group consisting of

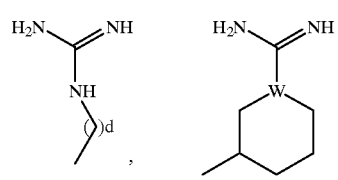

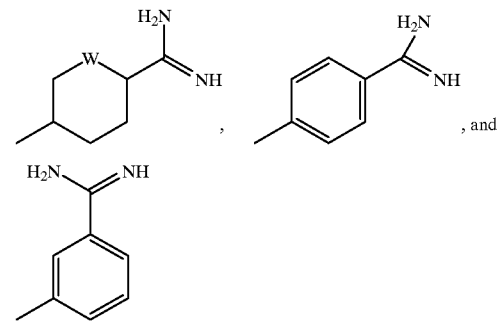

, and

where d is an integer from 0 to 5 and W is —N— or —CH—;
(e) R$_4$ is selected from the group consisting of
(i) —R$_1$, —OR$_1$, —NHR$_1$, —S(O)$_n$R$_1$, wherein n is 0, 1 or 2, and R$_1$ is as defined above, with the proviso that R$_1$ is not a camphor derivative or

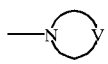

heterocycle,
(ii) —CF$_3$, —CF$_2$H, —OCF$_3$, —OCF$_2$H,
(iii) halogen,
(iv) alkyl of 1 to 6 carbon atoms substituted with Z$_5$, wherein Z$_5$ is selected from the group consisting of hydrogen, —OH, —OR$_8$, —CH$_3$, halogen, —C(O)OH, —C(O)OR$_8$ and —S(O)$_p$R$_8$, wherein R$_8$ is alkyl of 1 to about 6 carbon atoms, and p is 0, 1 or 2,
(v) alkyl of 1 to 3 carbon atoms substituted with cycloalkyl of 3 to 5 carbon atoms,
(vi) alkenyl of about 3 to about 6 carbon atoms,
(vii) cycloalkyl of about 3 to about 10 carbon atoms,
(viii) heteroaryl of about 5 to about 10 ring atoms having 1 to about 9 ring carbon atoms and the remainder of the ring atoms are heteroatoms selected from oxygen, sulfur and nitrogen, and
(ix) heteroaralkyl of about 5 to about 10 ring atoms having about 2 to about 15 carbon atoms which include 1 to about 9 ring carbon atoms and the remainder of the ring atoms heteroatoms selected from oxygen, sulfur and nitrogen;

(f) $R_5$ is selected from the group consisting of
(i) —$R_1$, —$OR_1$, —$NHR_1$, —$S(O)_nR_1$, $R_1$ is as defined above, with the proviso that $R_i$ is not a camphor derivative or

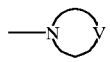

heterocycle,
(ii) —$CF_3$, —$CF_2H$, —$OCF_3$, or —$OCF_2H$, and
(iii) halogen;

(g) $R_6$ is selected from the group consisting of
(i) —$R_1$, —$OR_1$, —$NHR_1$, —$S(O)_nR_1$, wherein $R_1$ is as defined above, with the proviso that $R_1$ is not a camphor derivative or

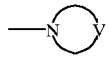

heterocycle,
(ii) —$CF_3$, —$CF_2H$, —$OCF_3$, or —$OCF_2H$,
(iii) halogen,
(iv) alkyl of 1 to about 12 carbon atoms substituted with $Z_6$, wherein $Z_6$ is selected from the group consisting of hydrogen, hydroxy, halogen, —$OR_9$, —$NHR_9$, —$C(O)OH$, —$C(O)OR_9$, and —$S(O)_pR_9$, wherein $R_9$ is alkyl of 1 to about 12 carbon atoms, aryl of about 6 to about 10 carbon atoms, aralkyl of about 7 to about 12 carbon atoms, heteroaryl of about 5 to about 10 ring atoms having 1 to about 9 ring carbon atoms and the remainder of the ring atoms heteroatoms selected from oxygen, sulfur and nitrogen, which is optionally mono-, di- or tri-substituted on the ring carbons with $Y_1$, $Y_2$ and/or $Y_3$; or heteroaralkyl of about 5 to about 10 ring atoms having about 2 to about 15 carbon atoms including 1 to about 9 ring carbon atoms and the remainder of the ring atoms heteroatoms selected from oxygen, sulfur and nitrogen, and which is optionally mono-, di- or tri-substituted on the ring carbons with $Y_1$, $Y_2$ and/or $Y_3$, and p is 0, 1 or 2;
(v) alkyl of 1 to about 3 carbon atoms substituted with cycloalkyl of about 3 to about 8 carbon atoms;
(vi) alkenyl of 2 to about 6 carbon atoms which is optionally substituted with cycloalkyl of about 3 to about 8 carbon atoms, aryl of about 6 to about 10 carbon atoms or heteroaryl of about 5 to about 10 ring atoms having about 2 to about 15 carbon atoms which include 1 to about 9 ring carbon atoms,
(vii) aralkyl of about 7 to about 15 carbon atoms which is optionally substituted on the alkyl chain with hydroxy or halogen, and optionally mono-, di- or tri-substituted on the ring carbons with $Y_1$, $Y_2$ and/or $Y_3$,
(viii) heteroaralkyl of about 5 to about 10 ring atoms having 1 to about 9 ring carbon atoms and the remainder of the ring atoms heteroatoms selected from oxygen, sulfur and nitrogen, which is optionally substituted on the alkyl chain with hydroxy or halogen, and optionally mono-, di- or tri-substituted on the ring carbons with $Y_1$, $Y_2$ and/or $Y_3$,
(ix) aralkenyl of 6 to about 15 carbon atoms which is optionally mono-, di- or tri-substituted on the aryl ring with $Y_1$, $Y_2$ and/or $Y_3$, and
(x) heteroaralkenyl of about 5 to about 10 ring atoms having 1 to 9 ring carbon atoms and the remainder of the ring atoms heteroatoms selected from oxygen, sulfur and nitrogen, which is optionally mono-, di- or tri-substituted on the ring carbons with $Y_1$, $Y_2$ and/or $Y_3$; and (h) $R_7$ is selected from the group consisting of
(i) $R_1$, wherein $R_1$ is as defined above with the proviso that $R_1$ is not a camphor derivative or

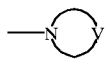

heterocycle,
(ii) —$CF_3$, or —$CF_2H$,
(iii) alkyl of 1 to about 10 carbon atoms, optionally substituted with —$CH_2OR_{10}$, —$CO_2R_{10}$, —$SO_2R_{10}$, —$CONR_{10}R_{11}$,
(iv) alkenyl of about 3 to about 10 carbon atoms, optionally substituted with —$CH_2OR_{10}$, —$CO_2R_{10}$, —$SO_2R_{10}$, —$CONR_{10}OR_{11}$,
(v) cycloalkyl of 3 to about 10 carbon atoms, optionally substituted with —$CH_2OR_{10}$, —$CO_2R_{10}$, —$SO_2R_{10}$, or —$CONR_{10}R_{11}$,
(vi) heteroaryl of about 5 to about 10 ring atoms having about 1 to about 9 carbon atoms, optionally substituted with —$CH_2OR_{10}$, —$CO_2R_{10}$, —$SO_2R_{10}$, or —$CONR_{10}R_{11}$, and
(vii) alkyl of 1 to about 3 carbon atoms substituted with heteroaryl of about 5 to about 10 ring atoms having about 1 to about 9 carbon atoms, optionally substituted with —$CH_2OR_{10}$, —$CO_2R_{10}$, —$SO_2R_{10}$, —$CONR_{10}R_{11}$, and wherein each $R_{10}$ and $R_{11}$ is independently selected and is alkyl of 1 to about 4 carbon atoms or hydrogen; or pharmaceutically acceptable salts thereof.

Preferred X groups include a direct link, —$SO_2$—, and —NH—$S(O)_2$—. An especially preferred X group is —$SO_2$—.

Preferred $R_1$ groups include alkyl, aralkyl, and aryl groups. Preferred aryl groups include substituted or unsubstituted phenyl and naphthyl, 2,3-methylenedioxyphenyl, and 3,4-methylenedioxyphenyl. Preferred substitutions include, methyl, methoxy, fluoro, chloro, trifluoromethyl, and —$OCF_3$. Meta and ortho ring substitutions are preferred. Meta and ortho di-substitutions on the ring are also preferred.

Particularly preferred $R_1$ groups include aralkyl groups. Especially preferred $R_1$ groups include substituted or unsubstituted benzyl and naphthylalkyl groups. Cyclohexyl and cyclohexylmethyl are also especially preferred $R_1$ groups.

A particularly preferred $R_2$ group is hydrogen.

Preferred $R_3$ groups include:

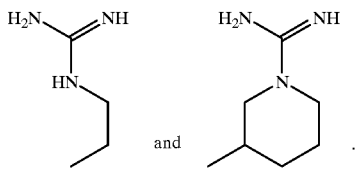

and

Preferred $R_4$ groups include:
(i) hydrogen,
(ii) alkyl of 1 to 6 carbon atoms substituted with $Z_5$, wherein $Z_5$ is selected from the group consisting of hydrogen, —OH, —$OR_8$, —$CH_3$, halogen, —C(O)OH, —C(O)$OR_8$ and —S(O)$_p R_8$;
(iii) alkyl of 1 to 3 carbon atoms substituted with cyclic alkyl of 3 to 5 carbon atoms,
(iv) alkenyl of about 3 to about 6 carbon atoms,
(v) cycloalkyl of about 3 to about 7 carbon atoms,
(vi) heteroaryl having 1 to about 4 ring carbon atoms and the remainder of the ring atoms are heteroatoms selected from oxygen, sulfur and nitrogen,
(vii) heteroaralkyl of 2 to about 6 carbon atoms having 1 to about 4 ring carbon atoms and the remainder of the ring atoms are heteroatoms selected from oxygen, sulfur and nitrogen, and
(viii) trifluoromethyl.

Preferred $R_4$ groups also include methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, S-3-hexyl, hydroxy, lower alkoxy of 1 to about 4 carbon atoms, phenyloxy, —$OCF_3$, and halogen.

Preferred $R_5$ groups include hydrogen, halogen, alkyl of 1 to about 5 carbon atoms, trifluoromethyl, and alkoxy of 1 to about 4 carbon atoms. Hydrogen is an especially preferred $R_5$ group.

Preferred $R_6$ groups include:
(i) hydrogen,
(ii) alkyl of 1 to about 12 carbon atoms substituted with $Z_6$, wherein $Z_6$ is as defined above,
(iii) alkyl of 1 to about 3 carbon atoms substituted with cycloalkyl of about 5 to about 8 carbon atoms,
(iv) alkenyl of about 2 to about 6 carbon atoms which is optionally substituted with cycloalkyl of about 3 to about 8 carbon atoms, aryl of about 6 to about 10 carbon atoms or heteroaryl of 1 to about 9 carbon atoms,
(v) aralkyl of about 7 to about 15 carbon atoms which is optionally substituted on the alkyl chain with hydroxy or halogen, and optionally mono-, di- or tri-substituted on the ring carbons with $Y_1$, $Y_2$ and/or $Y_3$,
(vi) heteroaralkyl of about 5 to about 10 ring atoms having 1 to about 9 ring carbon atoms and having the remainder of the ring atoms heteroatoms selected from oxygen, sulfur and nitrogen, which is optionally substituted on the alkyl chain with hydroxy or halogen, and optionally mono-, di- or tri-substituted on the ring carbons with $Y_1$, $Y_2$ and/or $Y_3$,
(vii) aralkenyl of about 6 to about 15 carbon atoms which is optionally mono-, di- or tri-substituted on the aryl ring with $Y_1$, $Y_2$ and/or $Y_3$, and
(viii) heteroaralkenyl of about 5 to about 10 ring atoms having 1 to 9 ring carbon atoms and having the remainder of the ring atoms heteroatoms selected from oxygen, sulfur and nitrogen which is optionally mono-, di- or tri-substituted on the ring carbons with $Y_1$, $Y_2$ and/or $Y_3$.

More preferred $R_6$ groups, when $R_4$ and $R_5$ are independently hydrogen or methyl, are selected from the group consisting of aralkyl of about 8 to about 13 carbon atoms, —O—$R_1$, —NH—$R_1$, and —S(O)$_p R_1$ wherein $R_1$ is preferably aralkyl of about 7 to about 12 carbon atoms. Preferred aryl components of the aralkyl groups include unsubstituted and substituted phenyl or naphthyl groups. Preferred substitutions on the aryl ring include methyl, methoxy, fluoro, chloro, trifluoromethyl, alkoxycarbonyl, methylenedioxy and amidocarbonyl. Phenylethyl, phenylpropyl, cyclohexylethyl and cyclohexylpropyl are especially preferred $R_6$ groups.

Especially preferred $R_7$ groups include hydrogen, methyl, difluoromethyl and trifluoromethyl. Hydrogen and methyl are especially preferred $R_7$ groups. Preferred $R_7$ groups also include those selected from the group consisting of:
(i) alkyl of 1 to about 10 carbon atoms, optionally substituted with —$CH_2 OR_{10}$, —$CO_2 R_{10}$, —$SO_2 R_{10}$, or —$CONR_{10} R_{11}$,
(ii) alkenyl of about 3 to about 10 carbon atoms, optionally substituted with —$CH_2 OR_{10}$, —$CO_2 R_{10}$, —$SO_2 R_{10}$, or -$CONR_{10} R_{11}$,
(iii) cycloalkyl of 3 to about 10 carbon atoms, optionally substituted with —$CH_2 OR_{10}$, —$CO_2 R_{10}$, —$SO_2 R_{10}$, or —$CONR_{10} R_{11}$,
(iv) aryl and heteroaryl of about 5 to about 10 ring atoms, optionally substituted with —$CH_2 OR_{10}$, —$CO_2 R_{10}$, —$SO_2 R_{10}$, or —$CONR_{10} R_{11}$, and
(v) alkyl of 1 to about 3 carbon atoms substituted with heteroaryl of about 5 to about 10 ring atoms having about 1 to about 9 carbon atoms, optionally substituted with —$CH_2 OR_{10}$, —$CO_2 R_{10}$, —$SO_2 R_{10}$, or —$CONR_{10} R_{11}$.

A particularly preferred embodiment is when $R_5$ and $R_6$ are independently selected to be hydrogen or methyl, and $R_4$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, and S-3-hexyl. A particularly preferred embodiment according to this aspect includes compounds where $R_4$ is hydrogen or methyl.

According to a particularly preferred aspect, provided are compounds of formula I wherein X is —S(O)$_2$—, $R_1$ is substituted or unsubstituted aralkyl, and $R_3$ is

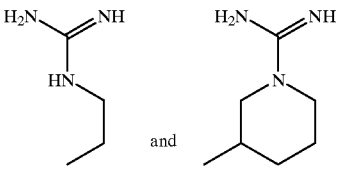

and

A very preferred aspect is directed to such compounds where $R_1$ is substituted or unsubstituted benzyl.

According to another preferred aspect, provided are compounds of formula I, wherein any two of $R_2$, $R_4$, $R_5$, and $R_6$ are hydrogen.

Particulary preferred compounds according to this invention include N-[2-hydroxy-3-(N-benzylsulfonylamino)-6-methylphenylacetyl]-L-argininal (Example 11) and N-[2-methoxy-3-(N-benzylsulfonylamino)-6-methylphenylacetyl]-L-argininal (Example 14).

According to another aspect, the present invention is directed to compounds having inhibitory activity toward proteases of the trypsin/chymotrypsin class. Crystal structures of serine protease inhibitors in complex with their cognate enzymes have been determined and are available from the Brookhaven National Laboratory Protein Data Bank. The three-dimensional crystal structures of proteases of the trypsin/chymotrypsin class are highly conserved within the class. The most potent inhibitors in the class make specific hydrogen bonds with structurally conserved backbone atoms of amino acid 216 of the protease (using the standard chymotrypsin numbering system). In most inhibitors, these hydrogen bonds are formed by atoms of peptide amide bonds or sulfonamide bonds. Thus, this aspect of the invention is directed to compounds of formula (II):

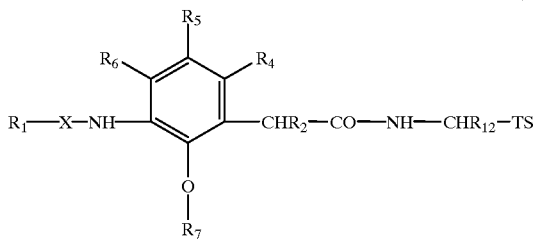

(II)

wherein a substituted phenol or phenyl ether is present in the compound in place of the amide bond of an inhibitor that makes hydrogen bonds to amino acid 216 in the trypsin/chymotrypsin class of serine proteases. Thus, according to this aspect of the present invention, provided are compounds of formula (II), wherein X, $R_1$, $R_2$, $R_4$, $R_5$, $R_6$, and $R_7$ are as defined hereinabove in connection with formula (I), and
(a) $R_{12}$ is selected from the group consisting of
 (i) alkyl of 1 to about 12 carbon atoms optionally substituted with amino, amidino, or guanidino,
 (ii) aralkyl of 7 to about 15 carbon atoms which is optionally substituted on a ring carbon with amino, amidino or guanidino,
 (iii) aryl of 6 to about 14 carbon atoms which is optionally substituted on a ring carbon with amino, amidino, or guanidino, and
 (iv) heteroaralkyl of 5 to about 14 ring atoms having about 1 to about 13 ring carbon atoms and the remainder of the ring atoms heteroatoms selected from oxygen, nitrogen and sulfur which is optionally substituted on a ring carbon with amino, amidino or guanidino; and
(b) TS is selected from the group consisting of
 (i) —CHO,
 (ii) —C(O)CF$_3$,
 (iii) —C(O)CF$_2$CF$_3$,
 (iv) —C(O)—C(O)—NHR$_{13}$,
 (v) —C(O)—C(O)$_2$R$_{13}$,
 (vi) —C(O)—C(O)—NR$_{13}$R$_{14}$,
 (vii) —B(OR$_{13}$)(OR$_{14}$),
 (viii) —C(O)CH$_2$Cl, and
 (ix) —C(O)R$_{15}$;
wherein $R_{13}$ and $R_{14}$ are independently selected from hydrogen lower alkyl of 1 to about 6 carbon atoms, cycloalkyl of 3 to about 10 carbon atoms, aralkyl of 7 to about 15 carbon atoms, and heteroaralkyl of about 5 to about 10 ring atoms having about 2 to about 15 carbon atoms which include 1 to about 9 ring carbon atoms and the remainder of the ring atoms heteroatoms selected from oxygen, nitrogen and sulfur, and $R_{15}$ is selected from aryl of 6 to about 14 carbon atoms and heteroaryl of 5 to about 14 ring atoms having 1 to about 13 ring carbon atoms and the remainder of the ring atoms selected from oxygen, nitrogen and sulfur. In the case where TS is (vii), additionally, —OR$_{13}$ and —OR$_{14}$ may be taken together to be —O[C(Z$_3$)(Z$_4$)]$_q$O— wherein Z$_3$, Z$_4$ and q are as defined in connection with formula (1). Also included are pharmaceutically acceptable salts of the compounds of formula (II).

According to a preferred aspect, inhibitors of elastase will have a small alkyl group, such as methyl, for $R_{12}$. Inhibitors of chymotrypsin preferably will have an aralkyl group, such as benzyl, for $R_{12}$ according to formula (II). Serine protease inhibitors that have a basic amino acid in the primary specificity site, such as inhibitors of trypsin, thrombin, factor Xa, factor VIIa, will have an amino, amidino, or guanidino substituted alkyl, aryl, or aralkyl group for $R_{12}$.

According to another aspect, the present invention includes within its scope salts of the compounds of formulas I and II. These salts include salts of the compounds of the present invention derived from the combination of such compounds and an organic or inorganic acid. In practice, the use of the salt form may amount to use of the (free) base form. The compounds of the present invention are useful in both free base and salt form, with both forms being considered as being within the scope of the present invention. These salts include acid addition salts, for example, salts of hydrochloric acid, hydrobromic acid, trifluoroacetic acid, acetic acid, benzene sulfonic acid and other suitable acid addition salts including maleate, fumarate and citrate salts.

2. Preparation of Preferred Compounds

Figure 2:
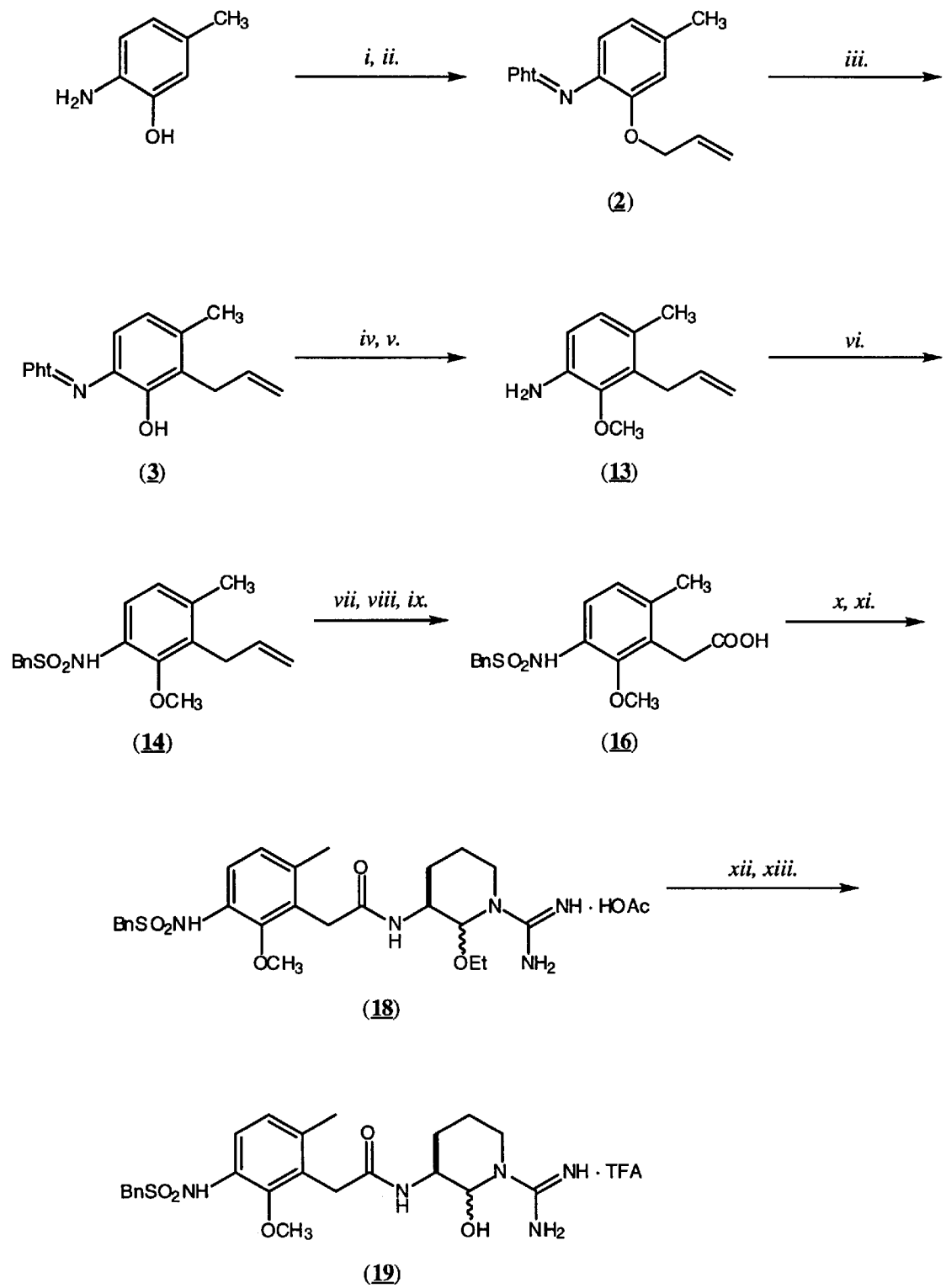
FIG. 2 provides a synthetic scheme for compound 19, which is further detailed in Examples 12 to 14. In this figure, the steps "i" through "xiii" are defined as follows. In the synthesis of (2) from 6-amino-M-cresol: i) phthalic anhydride, acetic acid, reflux, to give a 95% yield of (1); and ii) allyl bromide, K$_2$CO$_3$, acetonitrile, reflux to give a 97% yield of (2). In the synthesis of (3) from (2); iii) N,N-dimethylaniline, 185° C., about two hours, to give a 95% yield of (3). In the synthesis of (13) from (3): iv) iodomethane, K$_2$CO$_3$, acetonitrile, reflux, to give an 81% yield of (12); and v) hydrazine, ethanol, reflux, to give a 90% yield of (13). In the synthesis of (14) from (13): vi) α-toluene sulfonyl chloride, 4-methylmorpholine, acetonitrile, temperature 0° C., then warming to room temperature, to give approximately quantitative yield of (14). In the synthesis of (16) from (14): vii) ozone gas, methanol, −78° C.; viii) dimethylsulfide −78° C., then warming to room temperature, to give an intermediate phenylacetaldehyde (15); and ix) Jones' oxidation, acetone, 0° C., then warming to room temperature, to give a 46% overall yield of (16). In the synthesis of (18) from (16): 1. hydrochloride salt of N$^g$-nitro-L-argininal ethyl cyclol, EDC, HOBt, N,N-diisopropylethylamine acetonitrile, to give a 62% yield of (17); and xi) H$_2$, Pd/C catalyst, 55 PSI, ethanol, acetic acid, water, to give a 65% yield of (18). In the synthesis of (19) from (18): xii) 3N HCl, room temperature; and xiii) HPLC, to give a 74%, yield of (19).

FIGS. 1 and 2 depict synthetic schemes for two preferred compounds according to this invention. FIG. 1 outlines a sequence of reactions for the preparation of a preferred species of the present invention. Commercially available 6-amino-m-cresol is reacted with phthalic anhydride, optionally in the presence of an inert solvent like acetic acid, toluene, or xylene, at about 100–150° C. to afford the phthalimide intermediate 1. Reaction of 1 with allyl bromide in the presence of a suitable base such as anhydrous potassium carbonate in an inert solvent such as N,N-dimethylformamide, dioxane, tetrahydrofuran, or acetonitrile at a temperature in the range from about room temperature to about 110° C. provides the allyl ether derivative intermediate 2. Thermal Claisen rearrangement of 2, performed either neat or optionally in a suitable inert solvent such as N,N-dimethylaniline, at about 150–250° C. gives the allylphenol 3. Reaction of phenol derivative 3 with benzyl bromide in an inert solvent such as N,N-dimethylformamide, dioxane, tetrahydrofuran, or acetonitrile at about room temperature to about 110° C. provides the benzyl ether derivative 4. Cleavage of the phthalimido moiety of 4 is achieved selectively utilizing hydrazine in an alcoholic solvent such as ethanol at a temperature from about 20 to 80° C. and affords the aniline derivative 5. Coupling of 5 with a suitable sulfonyl chloride such as benzylsulfonyl chloride in an inert solvent such as N,N-dimethylformamide, dioxane, tetrahydrofuran, or acetonitrile at a temperature of about –10° C. to about 50° C. in the presence of a base such as pyridine, collidine, triethylamine, N,N-diisopropylethylamine, or N-methylmorpholine gives the benzylsulfonamide derivative 6. Treatment of a solution of 6 in solvent, preferably methanol, ethanol, ethyl acetate, acetone or methylene chloride, or mixtures of the preceding solvents, with a stream of ozone gas at a temperature of about −80° C. to about 0° C., followed by reductive decomposition of the ozonide in situ with reagents such as dimethyl sulfide, triethyl phosphite, triphenylphosphine, triethylamine, or zinc metal generates an aldehyde intermediate 7. When alcoholic solvents such as methanol are utilized, the reaction affords a mixture of the desired aldehyde along with varying amounts of the corresponding dimethyl acetal derivative. These mixtures are dissolved in a inert solvent such as acetone and hydrolyzed with dilute mineral acids such as 1 N hydrochloric acid at about room temperature to about reflux temperature which quantitatively affords the desired aldehyde 7. Oxidation of aldehyde substrate 7 with reagents such as pyridinium dichromate in N,N-dimethylformamide or chromic acid in acetone at a temperature of about 0° C. to 30° C. gives the carboxylic acid derivative 8. Compound 8 is coupled to $N^g$-nitro-L-argininal ethyl cyclol using 1-hydroxybenzotriazole monohydrate, 1-ethyl-3-(3-dimethylaminopropyl)carbodiimide hydrochloride salt, and then N,N-diisopropylamine to give 9. The $N^g$-nitro group of 9 is removed by treatment with hydrogen gas and palladium on carbon in ethanol, water, and acetic acid at about 20 to 60 psi. This reaction produces acetate acid salt 10. The ethyl cyclol group of 10 is hydrolyzed by treatment with a suitable acid catalyst such as dilute hydrochloric acid, sulfuric acid, methanesulfonic acid, perchloric acid or hexafluorophoshoric acid followed by HPLC purification with 0.1% trifluoroacetic acid in acetonitrile and water to produce the product 11.

The reaction scheme of FIG. 2 depicts the preparation of another very preferred compound. It differs from the synthetic scheme of FIG. 1 in that intermediate 3 is first reacted with methyl iodide in the presence of a suitable base such as anhydrous potassium carbonate in an inert solvent such as N,N-dimethylformamide, dioxane, tetrahydrofuran, or acetonitrile at a temperature of about room temperature to about 110° C., to provide the methyl ether derivative 12. Intermediate 12 is processed through an analogous set of reactions to those outlined in FIG. 1 to produce the target argininal derivative 19.

The preferred means of chemically coupling (as for example, intermediate 8 to argininal ethyl cyclol to give intermediate 9 as depicted in FIG. 1) include formation of a peptide bond using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling include DCC with HOBt, EDC with HOBt, BOP, HBTU or TBTU. In two-step coupling, an activated ester or anhydride of the C-terminal carboxy group of one coupling partner is formed prior to its coupling to the other coupling partner.

For compounds of the present invention containing alkenyl or aryl moieties substituted with halogen, cyano, nitro, or —S—$Z_1$, it is preferred to avoid the use of hydrogen gas with palladium on carbon for cleaving the $N^g$-nitro protecting group on the arginine side chain. Instead, it is preferred to use boron tris(trifluoroacetate), $B(OCOCF_3)_3$, to cleave the $N^g$-nitro of the arginine group. This reagent may be prepared by the reaction of $BBr_3$ and $CF_3COOH$ in dichloromethane at 0° C. Alternatively, the reagent is also commercially available. Generally, the $N^g$-nitro compound is treated with boron tris(trifluoroacetate) in trifluoroacetic acid at 0° C. See, e.g., Fieser, M. and Fieser, L. F., *Reagents for Organic Synthesis*, p. 46, John Wiley & Sons, New York (1974); and Pless, J., and Bauer, W. *Angew. Chem., Internat. Ed.*, 12, 147 (1973).

Another preferred reagent for selective nitro group cleavage is titanium trichloride. This reagent is commercially available. The $N^g$-nitro compound is treated with titanium trichloride in aqueous methanol containing an ammonium acetate buffer followed by exposure of the reaction mixture to air or dimethyl sulfoxide. See, e.g., Freidinger, R. M., Hirschmann, R., and Veber, D. F., *J. Org. Chem.*, 43, 4800 (1978).

Another preferred method for synthesizing these compounds having an L-argininal moiety is to use the di-N-t-butoxycarbonyl protecting group for the L-argininal moiety for groups incompatible with hydrogenation with palladium on carbon. For example, alpha-N-benzyloxycarbonyl-omega, omega'-di-N-t-butoxycarbonylarginine is dissolved in acetonitrile and treated with hydroxybenzotriazole and 1-ethyl-3-(3-dimethylamino-propyl)carbodiimide HCl salt to form alpha-N-benzyloxycarbonyl-omega, omega'-di-N-t-butoxycarbonyl-L-arginine lactam. The lactam is reduced by treatment with LiAlH$_4$ in THF at −70° C. to provide alpha-N-benzyloxycarbonyl-omega, omega'-di-N-t-butoxycarbonyl-L-argininal. This aldehyde is protected as the diethyl acetal by treatment with ethanol and HCl. The N-benzyloxycarbonyl protecting group is removed by treatment with hydrogen gas and palladium on carbon to give omega, omega'-di-N-t-butoxycarbonyl-L-argininal diethyl acetal, HCl salt. This protected L-argininal moiety can then be coupled to a desired carboxylic acid by treatment with N-hydroxybenzotriazole and 1-ethyl-3-(3-dimethylamino-propyl)carbodiimide HCl salt. The diethyl acetal and the di-Boc protecting groups are removed by treatment with hexafluorophosphoric acid in acetonitrile at 0° C. The reaction mixture is quenched by addition of 2.5 M aqueous sodium acetate until pH 4 is reached. The mixture is filtered through a 2 micron filter. Preparative HPLC using 0.1% CF$_3$COOH in 10–40% aqueous acetonitrile provides the trifluoroacetate salt of the desired substituted L-argininal compound.

Figure 3:
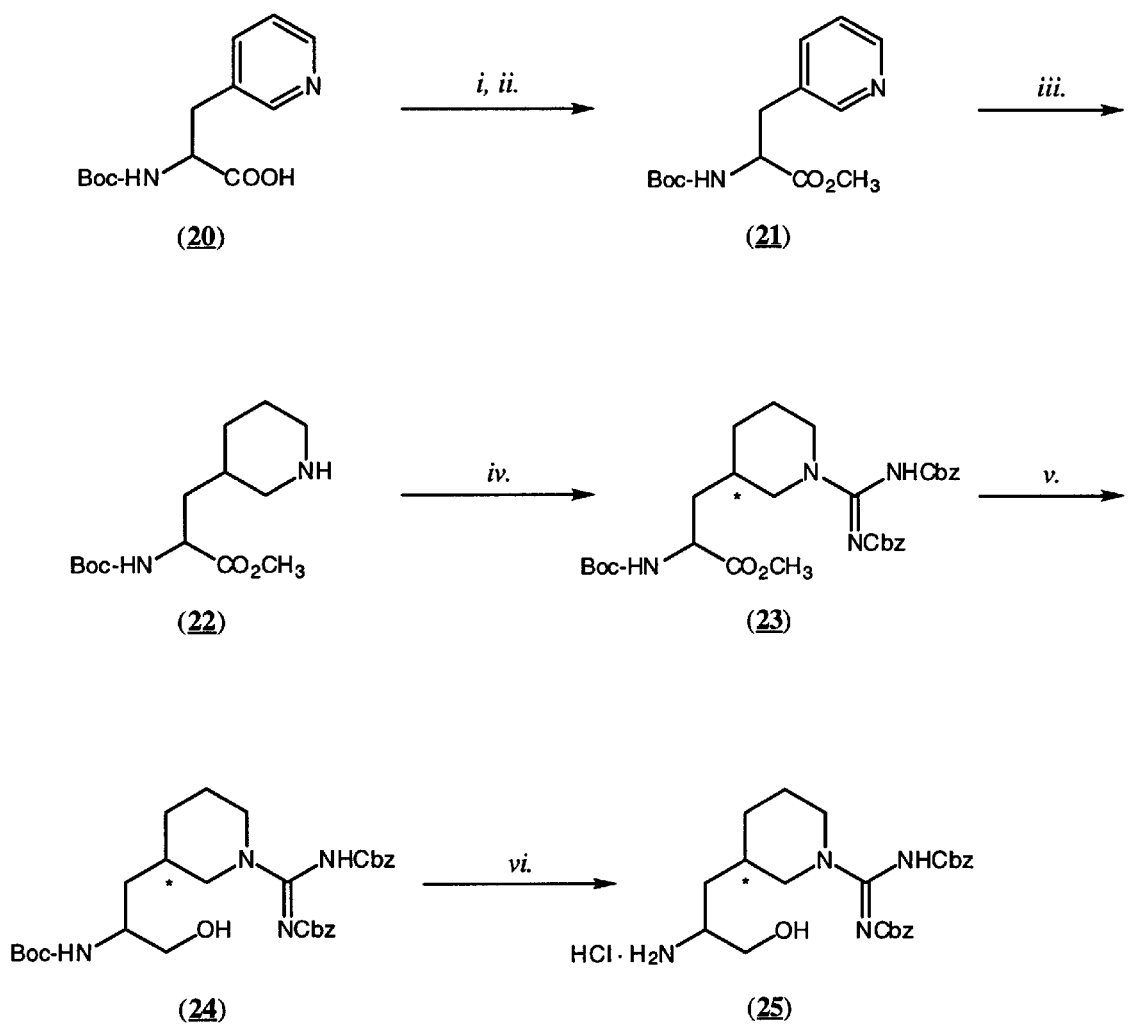
FIG. 3 depicts a reaction scheme for preparation of an intermediate used for the synthesis of compounds of the present invention. In this figure, "i" through "vi" are defined as: i) thionyl chloride, methanol; ii) di-tert-butyl dicarbonate, pH 7–8; iii) hydrogen gas, platinum oxide in ethanol, water and acetic acid; iv) bis-benzyloxycarbonyl S-methylisothiourea, base, tetrahydrofuran; v) calcium chloride, sodium borohydride in tetrahydrofuran and ethanol; vi) HCl (anhydrous). "*" indicates the position of an asymmetric carbon atom.
Figure 4:
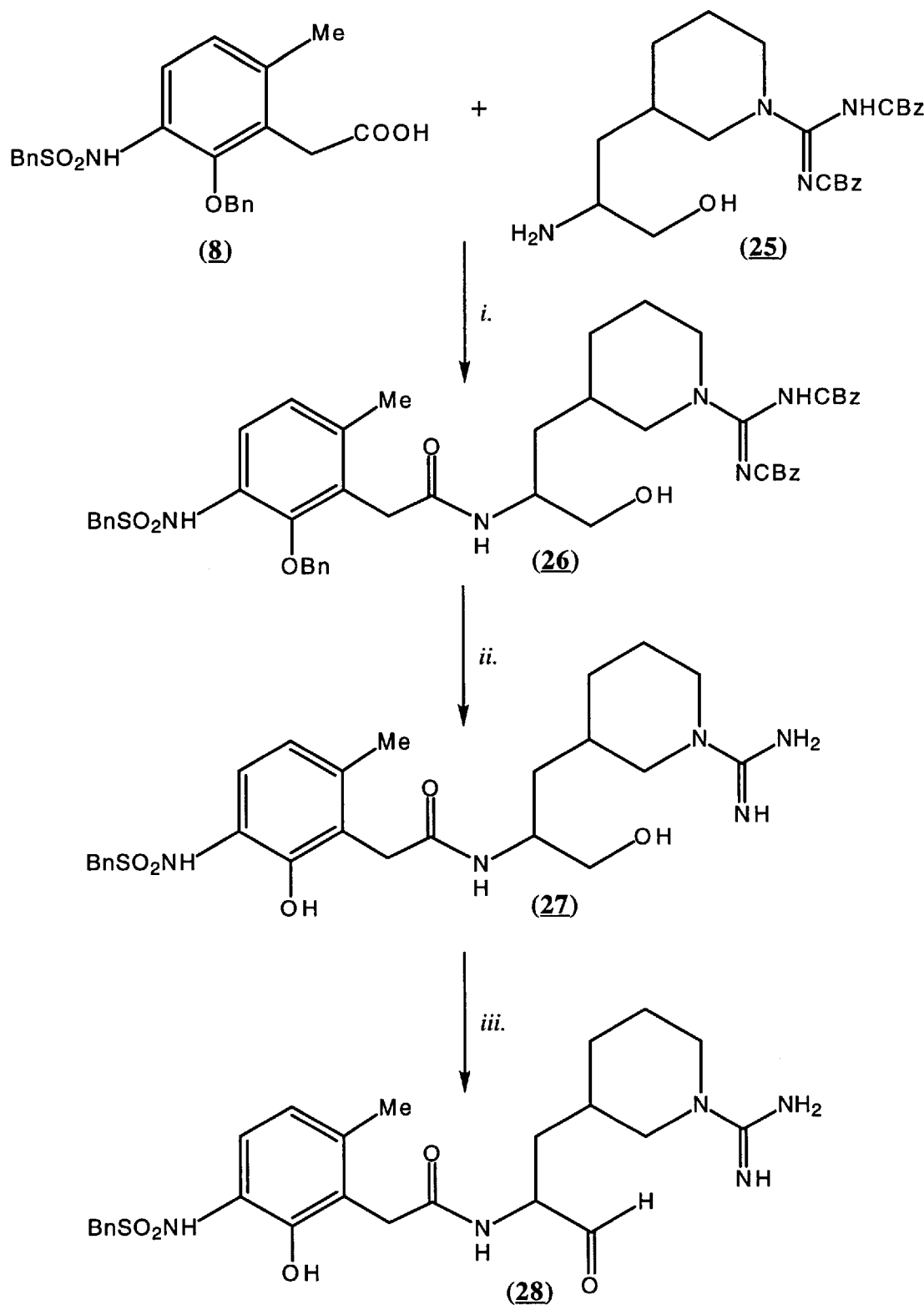
FIGS. 4 and 5 depict preferred reaction schemes for synthesis of certain compounds of the present invention. In these figures, "i" through "iii" are defined as: i) HOBt, EDC, dimethylaminopyridine, triethylamine; ii) hydrogen gas, 10% palladium on charcoal and iii) dimethylsulfoxide, toluene, dichloroacetic acid and EDC.
Figure 5:
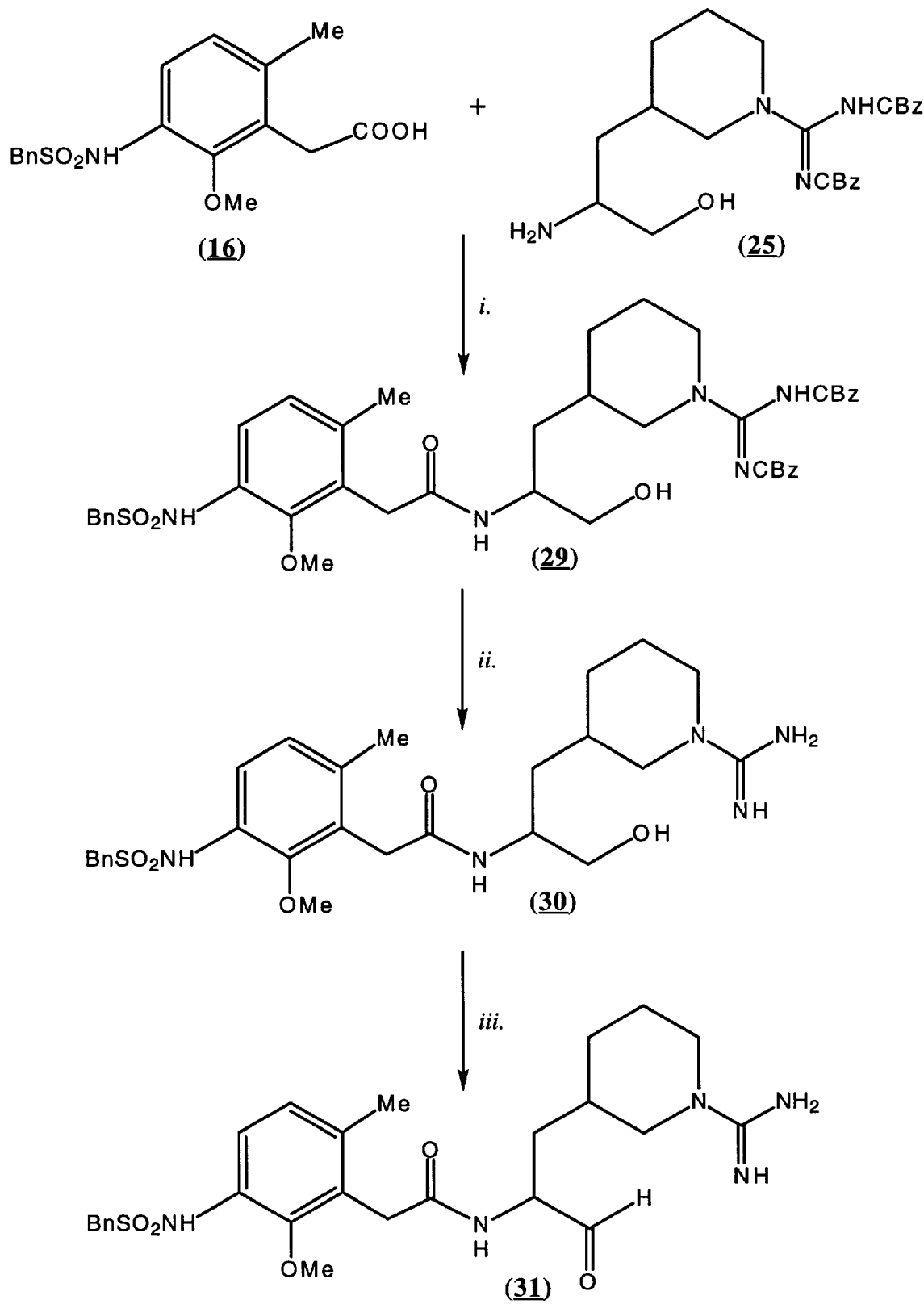

FIG. 3 depicts a reaction scheme for the preparation of intermediate 25 which is used in the synthesis of compounds of formula (I) according to reaction schemes depicted in FIGS. 4 and 5. Examples 15 to 19 describe preparation of 25 in further detail.

FIGS. 4 and 5 depict reaction schemes for the preparation of certain compounds of formula (I) wherein $R_3$ is a 3-piperidinyl-(N-guanidino) group. Preparation of compound 28 is described in further detail in Examples 20 to 22. Compound 31 is prepared using the appropriate reagents according to procedures similar to those described in Examples 20 to 22.

Figure 6:
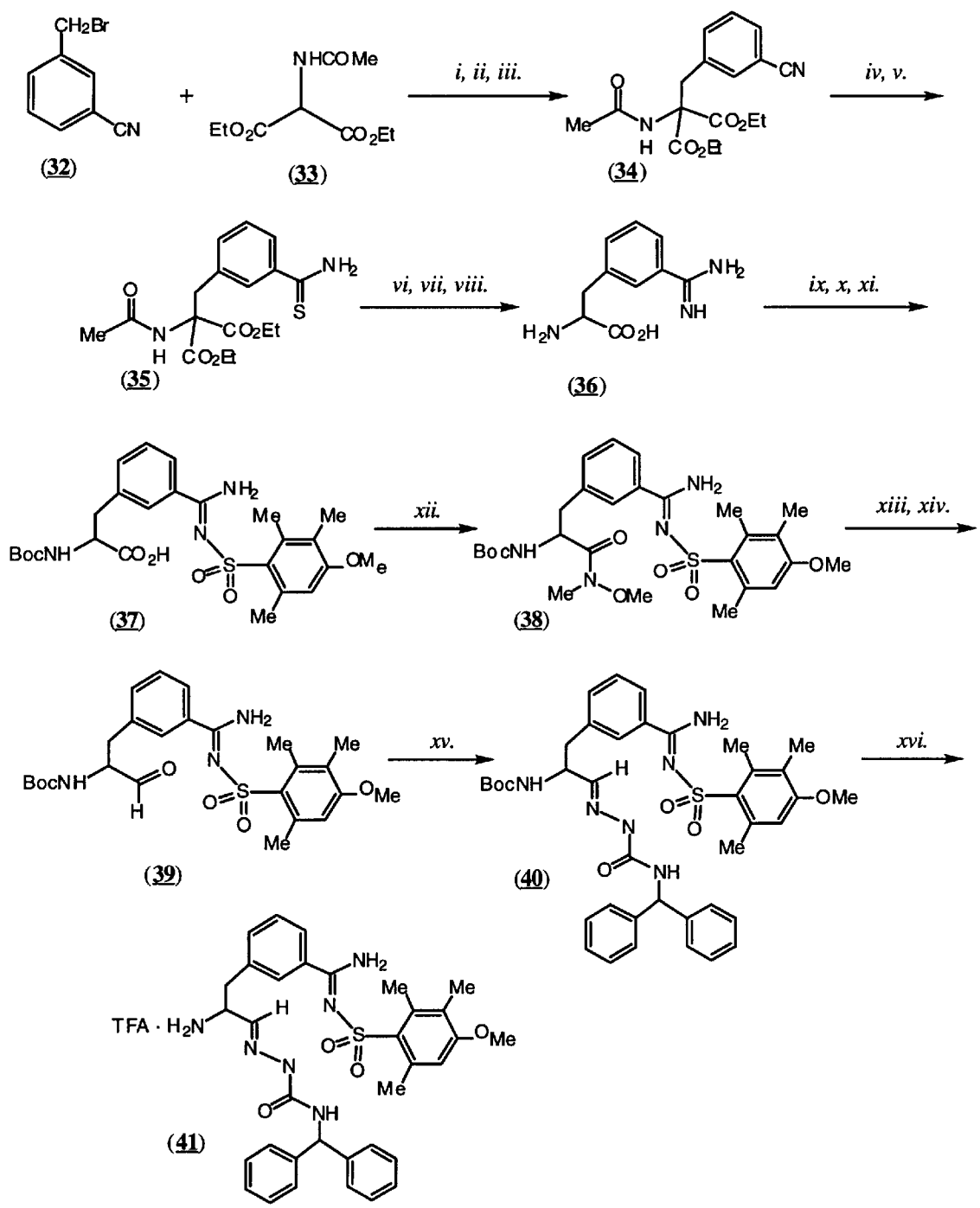
FIG. 6 depicts a reaction scheme for preparation of an intermediate used for the synthesis of compounds of the present invention. In this figure, "i" through "xvi" are defined as: (i) potassium iodide, dioxane; (ii) 2.5 M sodium ethoxide in ethanol, argon atmosphere; reflux 6 hours; (iii) yield after workup 60%; (iv) pyridine, triethylamine; (v) H$_2$S(g), stirred at room temperature 16 hours; yield after workup 98%; (vi) acetone, iodomethane, reflux 30 minutes, filtration, methanol; (vii) ammonium acetate, reflux 1 hour, filter and dry; (viii) concentrated HCl, reflux 3 hours, yield after workup 30%; (ix) dioxane, sodium bicarbonate, di-t-butyl dicarbonate, stir 18 hours at room temperature; (x) 4° C., 4.0 N NaOH to pH 12; 4-methoxy-2,3,6-trimethylbenzenesulfonyl chloride in dioxane; (xi) 1.0 N HCl to pH 7–8, water, yield after workup 68%; (xii) O,N-dimethyl hydroxylamine hydrochloride, hydroxybenzotriazole hydrate, 4-methylmorpholine, THF, stir 2 hours, yield after workup 69%; (xiii) LiAlH$_4$, THF, dry ice/acetone bath; (xiv) aqueous potassium bisulfate, yield after workup 86%; (xv) 4-Benzhydrylsemicarbizide trifluoroacetate salt (the compound of Example 23), sodium acetate trihydrate in ethanol, reflux, yield after workup 89%; and (xvi) 50% TFA/DCM, add to ether, yield after workup 79%.
Figure 7:
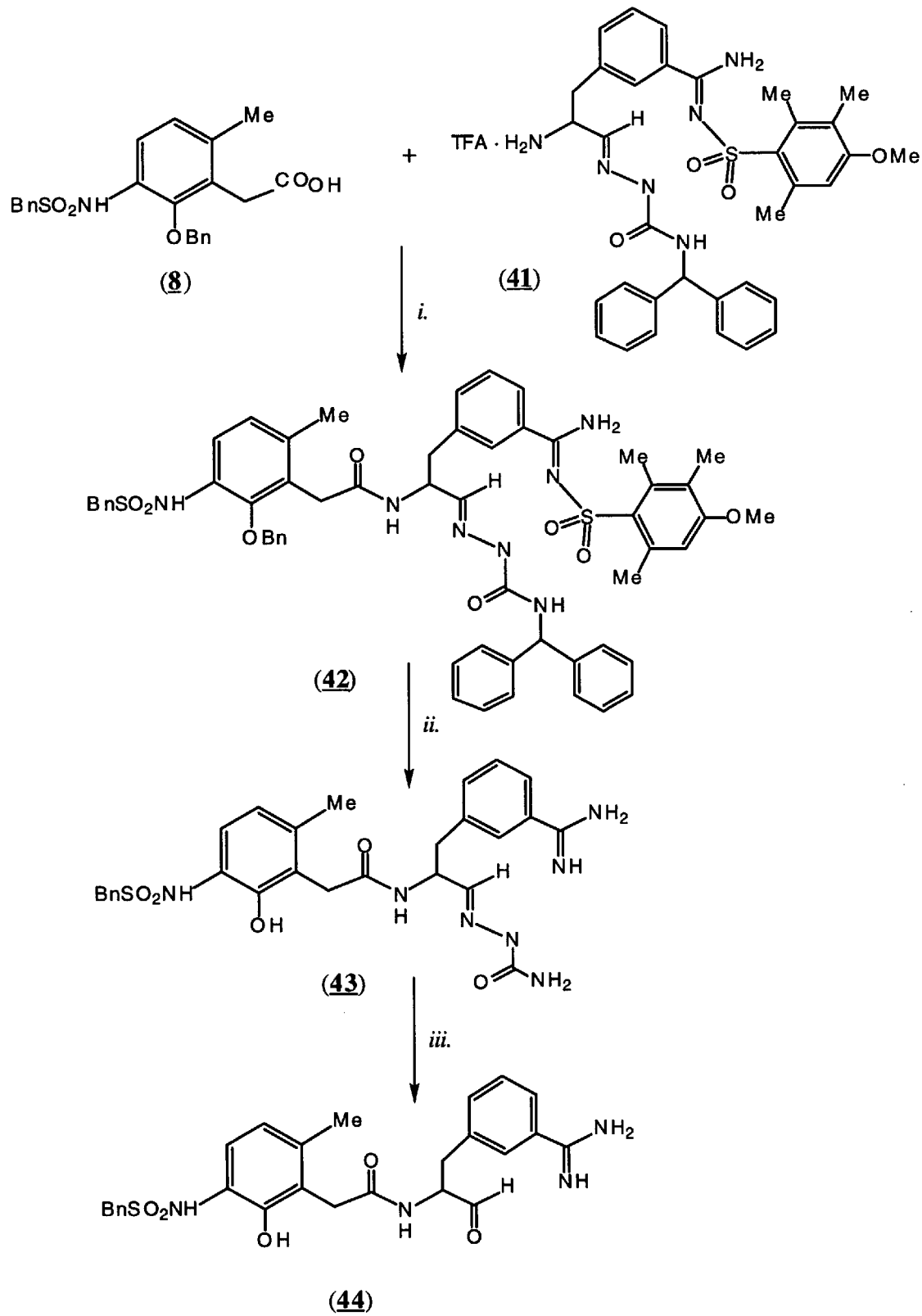
FIG. 7 depicts a preferred reaction scheme for synthesis of certain compounds of the present invention. In this figure, "i" through "iii" are defined as: (i) EDC, hydroxybenzotriazole, 4-methyl-morpholine in DMF; (ii) HF/anisole (9:1), aqueous acetic acid; and (iii) methanol, 1% HF(aqueous), formalin.

FIG. 6 depicts a reaction scheme for preparation of intermediate 41 which is used in the synthesis of compounds of formula (I) according to the reaction scheme depicted in FIG. 7. Examples 24 to 30 describe the preparation of 41 in further detail.

Intermediates used in the preparation of compounds of formula (I) having a 4-amidinophenylalaninal group at P1 may be prepared according to the reaction scheme depicted in FIG. 6 and described in Examples 24 to 30, using the appropriate alpha-bromo-para tolunitrile starting material.

FIG. 7 depicts a reaction scheme for preparation of a compound of formula (I) wherein $R_3$ is 3-amidinophenyl. Preparation of 44 is more fully described in Examples 31 to 33.

Figure 12:
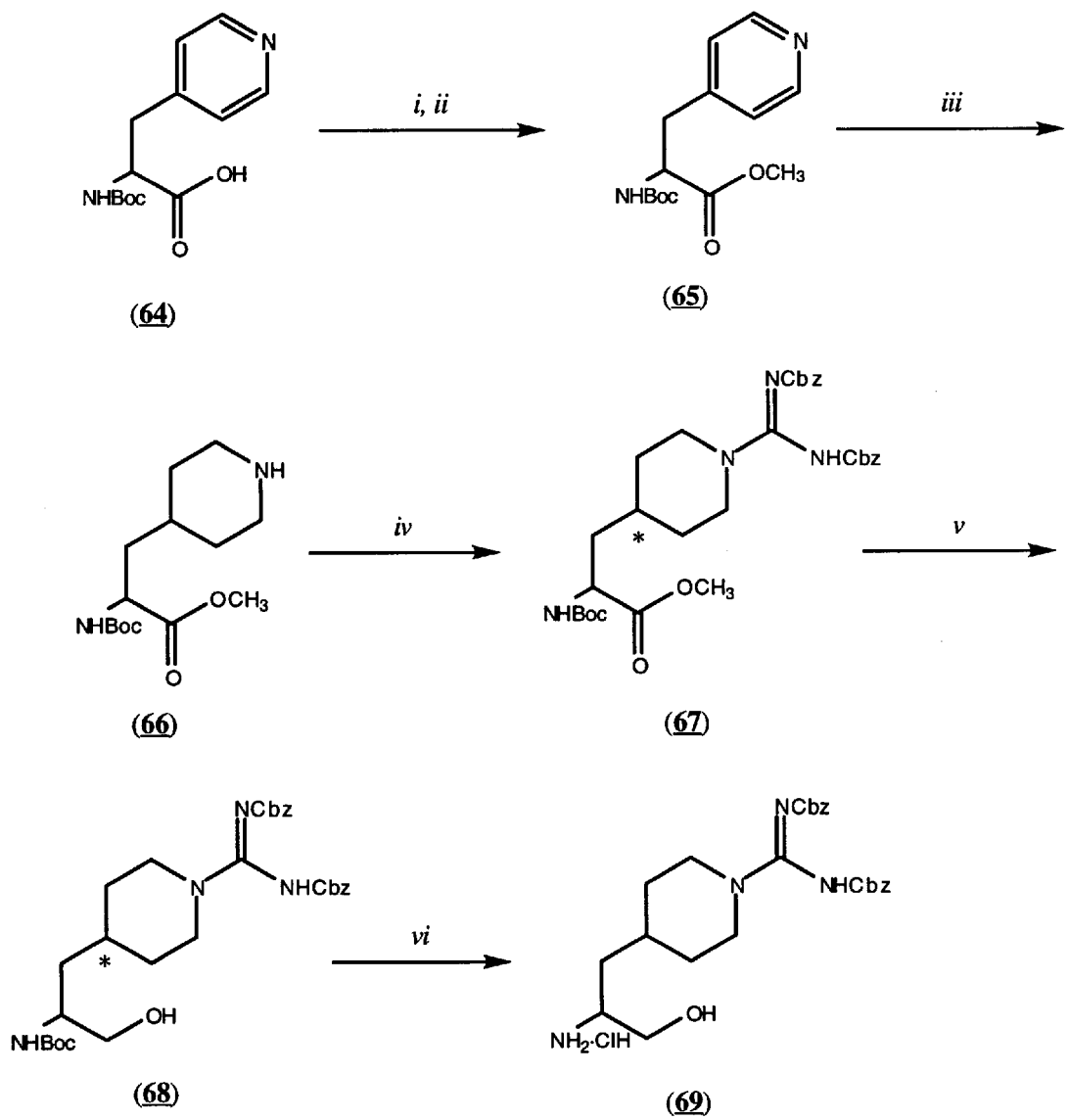
FIG. 12 depicts the reaction scheme for preparation of intermediate 69, which is used for the synthesis of certain compounds of the present invention. In this figure "i" through "vi" are defined as: i) thionyl chloride, methanol; ii) di-tert-butyl carbonate, pH 7–8; iii) hydrogen gas, platinum oxide in ethanol, water and acetic acid; iv) bis-benzyloxycarbonyl 5-methylisothiourea, base, tetrahydrofuran; v) calcium chloride, sodium borohydride in tetrahydrofuran and ethanol; vi) HCl (anhydrous). "*" indicates the position of an assymetric carbon atom.

FIG. 12 depicts a reaction scheme for the preparation of intermediate 69 which is used in the synthesis of compounds of formula (I). Intermediate 69 is prepared by procedures similar to those described in Examples 15 to 19 using the appropriate starting materials. Intermediate 69 may be coupled to intermediates such as 8 and 16 according to reaction schemes analogous to those depicted in FIGS. 4 and 5.

Figure 8:
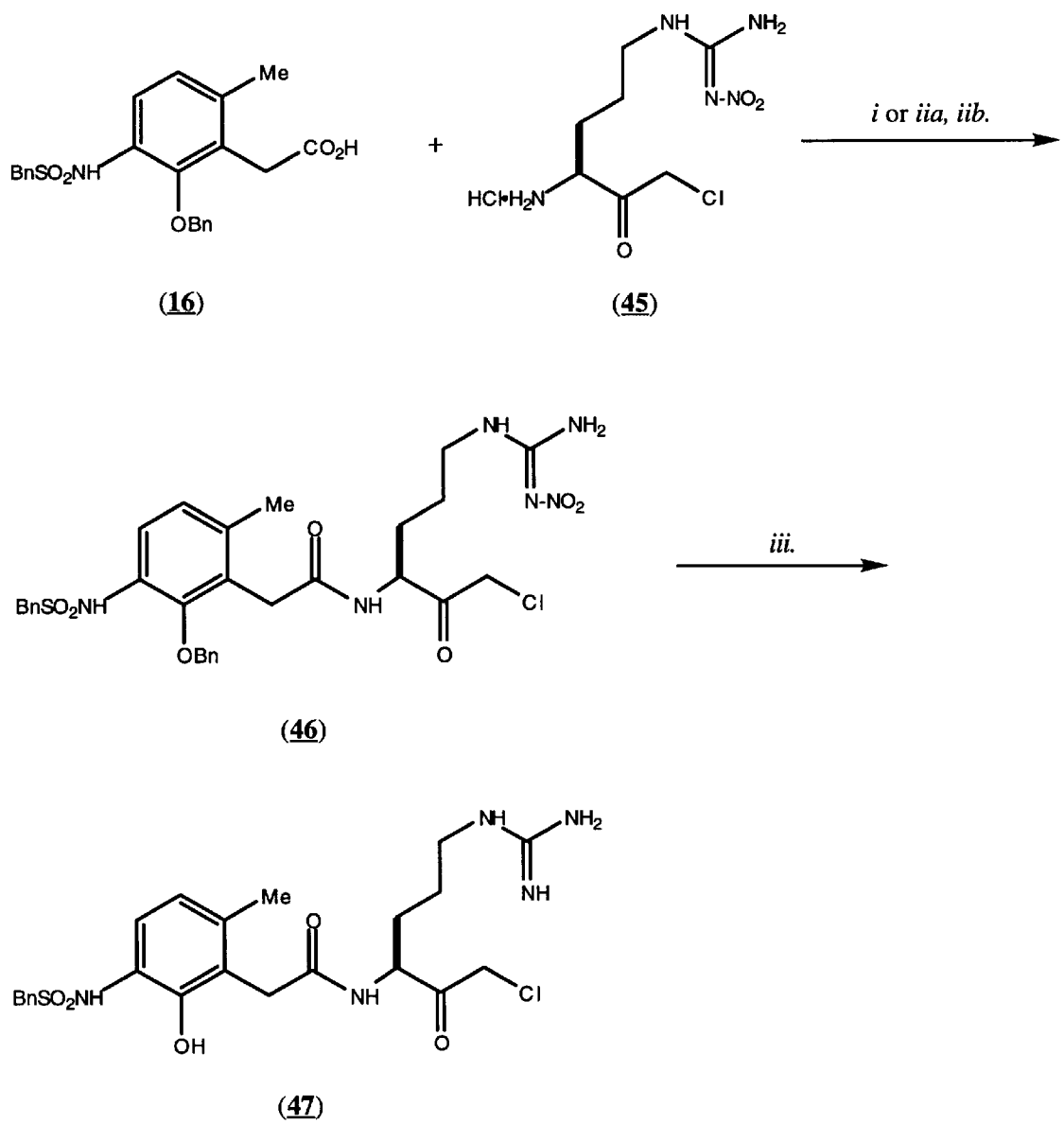
FIG. 8 depicts a reaction scheme for the preparation of a compound of formula (II) which incorporates an arginine chloromethylketone moiety at P1. In this figure, "i" through "iii" are defined as: (i) EDC, HOBt, NMM, CH$_3$CN, room temperature; (iia) i-BuOCOCl, NMM, DMF at −20° C.; (iib) add 45, DMF, Et$_3$N, allow temperature to increase from −20° to room temperature; and (iii) HF, anisole.

Compounds of formula (II) may be prepared by methods such as those described hereinbelow:

FIG. 8 outlines a synthetic sequence for the preparation of a preferred compound of the invention which incorporates a P1-arginine chloromethylketone moiety. Coupling of carboxylic acid derivative 16 with the known arginine chloromethylketone precursor 45 (Kettner, C. and Shaw, E., Biochemistry, 17: 4778 (1978); Kettner, C. and Shaw, E., Biochim. Biophys. Acta, 569: 31 (1979)) under standard carbodiimide conditions of EDC, HOBt, and NMM at about 0° C. to room temperature or under standard mixed anhydride conditions of isobutyl chloroformate and NMM at about −30° C. to room temperature affords intermediate 46. Suitable solvents for either reaction include THF, acetonitrile or DMF. Double deprotection of intermediate 46 with anhydrous hydrogen fluoride optionally in the presence of anisole at a temperature in the range of about −78° C. to about room temperature gives the desired product 47.

Figure 9:
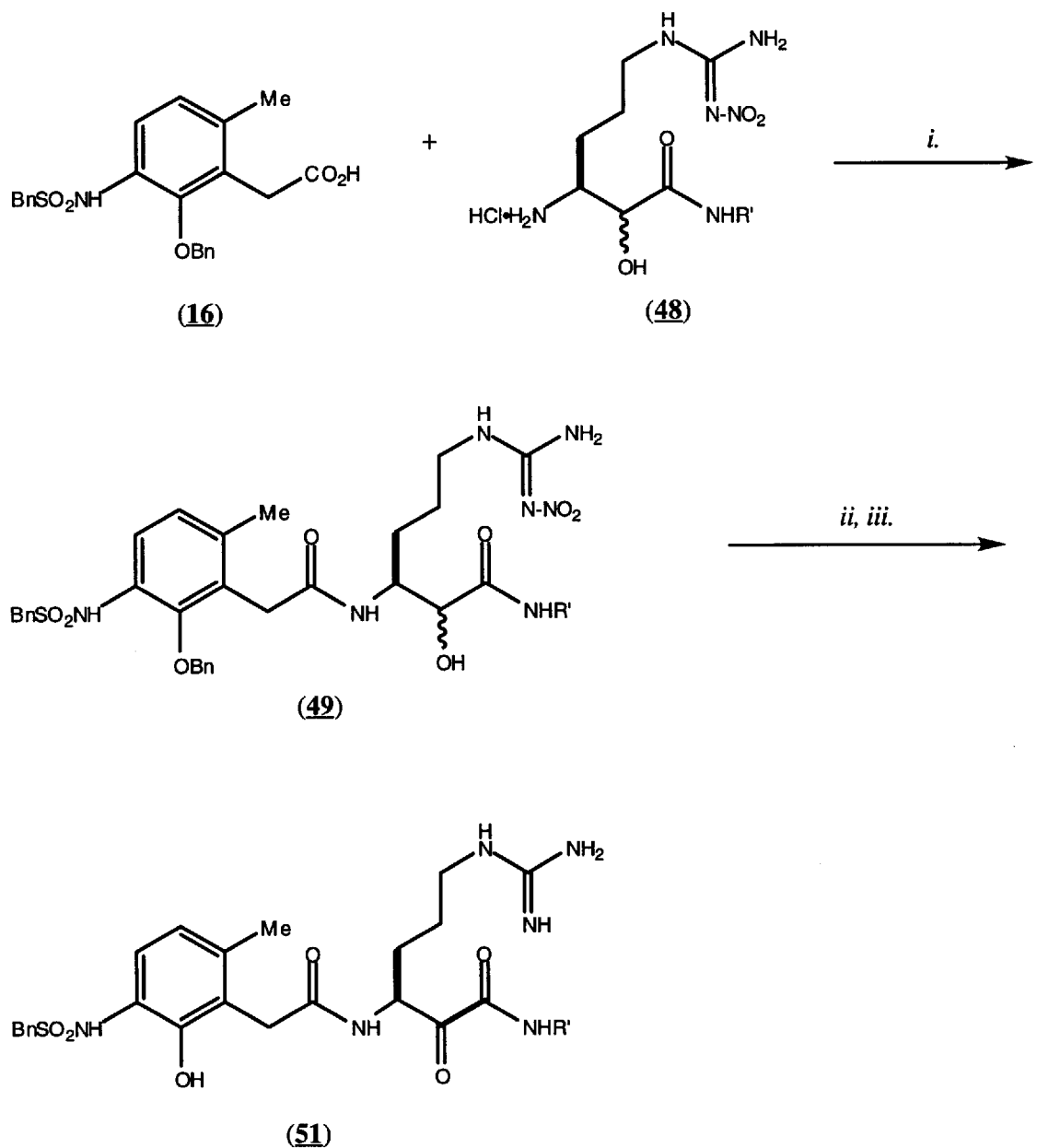
FIG. 9 depicts a reaction scheme for the preparation of a compound of formula (II) which incorporates an argimine ketoamide moiety at P1. In this figure, "i" through "iii" are defined as: (i) EDC, HOBt, NMM, CH$_3$CN, room temperature; (ii) H$_2$, palladium on carbon, EtOH, H$_2$O, HOAc to give intermediate 50; and (iii) EDC, DMSO, DCAA, toluene, temperature is allowed to increase from 0° to room temperature.

FIG. 9 outlines a synthetic sequence for the preparation of a preferred compound of the invention which incorporates a P1-ketoargininamide moiety. Coupling of carboxylic acid derivative 16 with the known hydroxyargininamide precursor 48 (see, e.g. commonly assigned U.S. Pat. Nos. 5,371,072 and 5,597,804) under standard carbodiimide conditions of EDC, HOBt, and NMM at about 0° C. to room temperature or under standard mixed anhydride conditions of isobutyl chloroformate, and NMM at about −30° C. to room temperature affords intermediate 49. Suitable solvents for either reaction include THF, acetonitrile or DMF. Deprotection of intermediate 49 with anhydrous hydrogen fluoride optionally in the presence of anisole at about −78° C. to about room temperature, or by catalytic hydrogenation using a suitable catalyst such as Pd/C or Pd(OH)$_2$/C in a solvent composed of ethanol, water and/or acetic acid gives the intermediate 50. Finally, oxidation of intermediate 50 under the standard Moffatt conditions with EDC, DMSO and dichloroacetic acid in a suitable solvent such as toluene at about −10° C. to room temperature produces the desired product 51.

Figure 10:
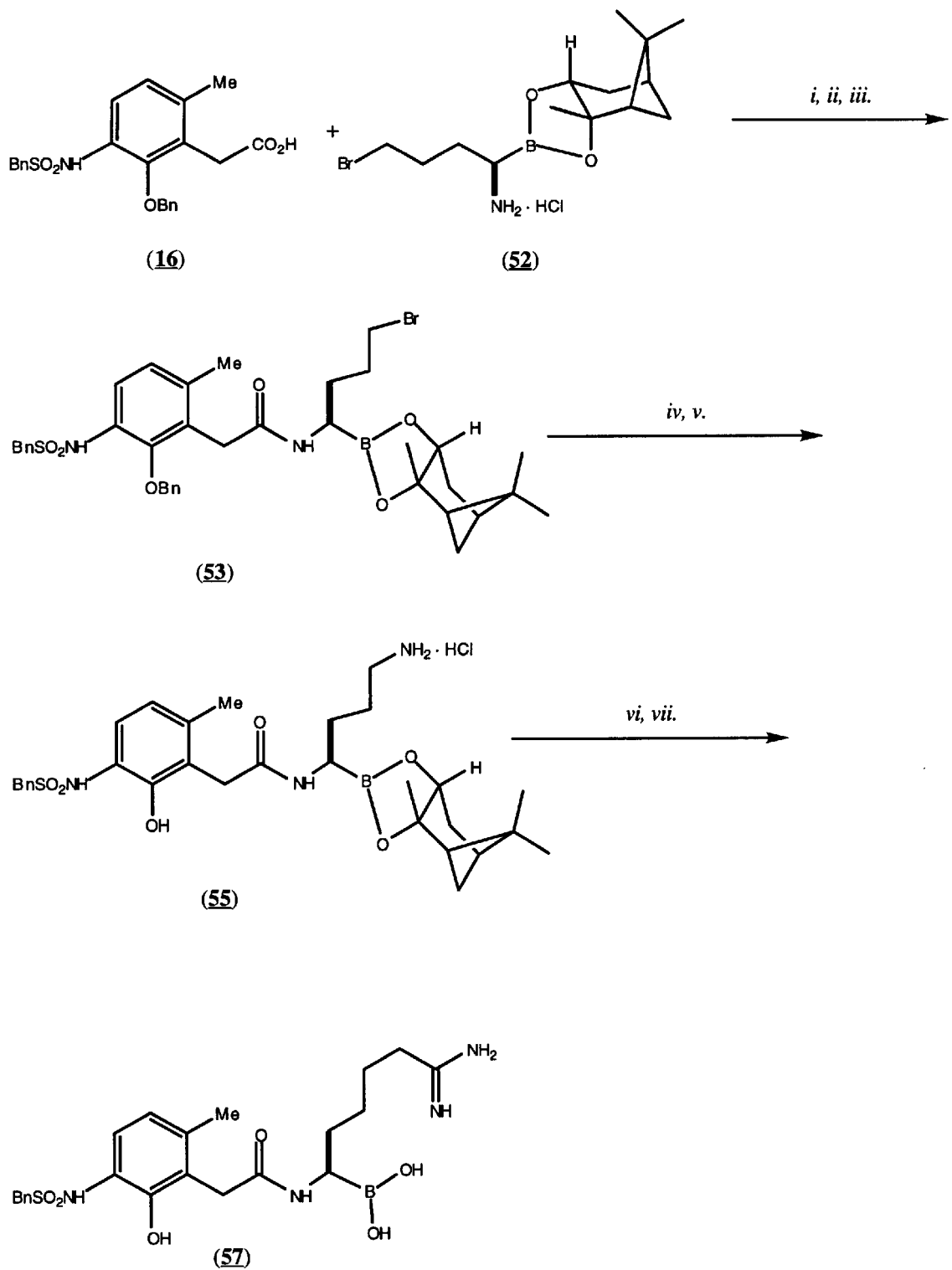
FIG. 10 depicts a reaction scheme for the preparation of a compound of formula (II) having a boronic acid moiety at P1. In this figure, "i" through "vii" are defined as: (i) treatment of 16 with iBuCOCl, NMM, THF, at −20° C; (ii) addition of 52, CHCl$_3$; (iii) Et$_3$N, at −20° C; (iv) NaN$_3$, DMF, at temperature of 80 to 100° C. to give intermediate azide 54; (v) H$_2$, Pd(OH$_2$)/carbon, methanol, HCl; (vi) formamidine sulfonic acid (H$_2$NCl=NH) SO$_3$H, DMAP, EtOH, reflux, to give intermediate 56; and (vii) PhB(OH)$_2$, Et$_2$O, H$_2$O.

FIG. 10 outlines a synthetic sequence for the preparation of a preferred compound of the invention which incorporates a P1-boronic acid moiety. Coupling of carboxylic acid derivative 16 with the known protected boroarginine ester precursor 52 (See, e.g., Wityak, J. et. al., *J. Org. Chem.*, 60: 3717 (1995) and references cited therein) under standard carbodiimide conditions of EDC, HOBt, and NMM at about 0° C. to room temperature or under standard mixed anhydride conditions of isobutyl chloroformate, NMM and then in situ added Et$_3$N at about −30° C. to room temperature affords intermediate 53. Suitable solvents for either reaction include THF, acetonitrile, dichloromethane, chloroform, DMF, or mixtures thereof. Reaction of intermediate 53 with sodium azide in a suitable inert solvent such as DMF, N,N-dimethylacetamide, DMSO or 1-methyl-2-pyrrolidinone at about room temperature to about 100° C. affords the azide 54. Catalytic hydrogenation of intermediate azide 54 in an alcoholic solvent such as methanol preferably in the presence of hydrogen chloride gives the intermediate amine salt 55. Reaction of intermediate 55 with formamidine sulfonic acid in an alcoholic solvent such as ethanol preferably in the presence of a tertiary amine, especially DMAP, at about room temperature to 100° C. produces intermediate 56. Deprotection of intermediate 56 by an exchange reaction preferably with phenylboronic acid in a two-phase solvent system such as ether and water then gives the desired boronic acid product 57.

Figure 11:
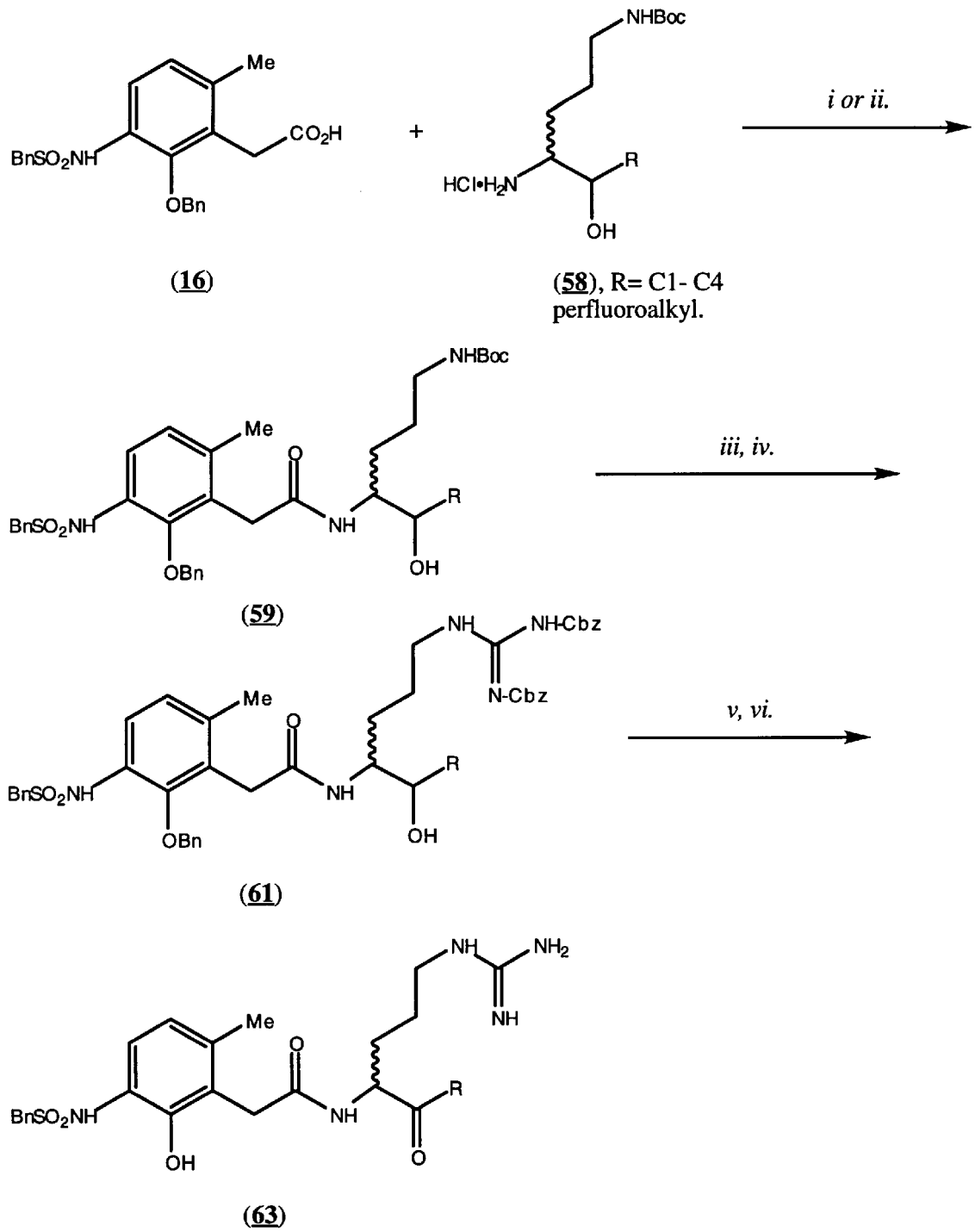
FIG. 11 depicts a reaction scheme for the preparation of a compound of formula (II) having a C$_1$ to C$_4$ perfluoroalkylargininyl ketone moiety at P1. In this figure, "i" to "vi" are defined as: (i) EDC, HOBt, NMM, CH$_3$CN, at room temperature; (ii) i-BuOCOCl, NMM, DMF, temperature about −30° C. to −15° C. to room temperature; (iii) TFA, CH$_2$Cl$_2$, temperature about 0° C. to room temperature to give intermediate 60; (iv) bis-Cbz-S-methyl isothiourea (CbzNHC(=NCbz)SMe), THF, Et$_3$N; (v) Swern oxidation with mixture of oxalylchloride, DMSO, Et$_3$N, CH$_2$Cl$_3$, temperature at about −78° C. to room temperature, to give ketone intermediate 62; and (vi) HF, anisole, temperature at about −78° C. to room temperature.

FIG. 11 outlines a synthetic sequence for the preparation of a preferred compound of the invention which incorporates a P1-C1 to C4 perfluoroalkylargininyl ketone moiety. Coupling of carboxylic acid derivative 16 with the known perfluoroargininol precursor 58 (see, e.g., Schacht, A. L., Shuman, R. T., and Wiley, M. R., UK Patent Application GB 2287027 A, Sep. 6, 1995 and references cited therein; for the application of the Dakin-West protocol to arginine and related substrates, see also Ueda, T., Kam, C. M., and Powers, J. C., *Biochem. J.*, 265: 539 (1990); Buchanan, G. L., *Chem. Soc. Rev.*, 17: 91 (1988)) under standard carbodiimide conditions of EDC, HOBt, and NMM at about 0° C. to room temperature or under standard mixed anhydride conditions of isobutyl chloroformate, and NMM at about −30° C. to room temperature affords intermediate 59. Suitable solvents for either reaction include THF, acetonitrile, dichloromethane, chloroform, DMF or mixtures thereof. Removal of the Boc protecting group is accomplished by treatment of 59 with an acid catalyst such as TFA, or hydrogen chloride in a suitable insert solvent such as dichloromethane, ethanol or ethyl acetate and produces intermediate 60. Reaction of 60 with a suitable optionally protected guanylating reagent such as bis-Cbz-S-methyl isothiourea in an inert solvent such as DMF or THF in the presence of a base such as triethylamine provides the protected intermediate 61. Swern oxidation of 61 with a mixture of oxalyl chloride, DMSO, triethylamine in dichloromethane at about −78° C. to room temperature gives the ketone intermediate 62. Finally, deprotection of 62 with anhydrous hydrogen fluoride optionally in the presence of anisole at about −78° C. to room temperature produces the desired perfluoroalkylargininyl ketone 63.

3. Selection of Preferred Compounds

The compounds of the present invention are screened for their ability to inhibit thrombin, plasmin, tissue plasminogen activator (t-PA), activated protein C (aPC), chymotrypsin, and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and/or trypsin for a given compound is greater than or equal to its $IC_{50}$ (or $K_i$, respectively) for thrombin.

With respect to compounds within the present invention that inhibit members within the trypsin/chymotrypsin family, including trypsin, chymotrypsin, elastase, and serine proteases involved in the coagulation cascade, "not specifically inhibiting" means the $IC_{50}$ or $K_i$ for the target enzyme is less than or equal to the $IC_{50}$ or $K_i$ for non-target enzymes contacted with the inhibitor.

For screening compounds using these assays, the compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is the concentration of test compound which gives 50% inhibition of the rate of substrate turnover. Likewise, the $K_i$ of a compound of the present invention is determined from the rate of substrate turnover caused by the specific enzyme being measured at various enzyme concentrations. Examples A, B and C provide an exemplars of in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the highest concentration of compound tested is considered to be the reported $IC_{50}$.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which, as noted, those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remington's Pharmeceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutcial compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility.

Certain compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. See, e.g., Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of blood clotting enzymes, such as factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

Certain of the compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

Certain compounds of the present invention have utility as inhibitors of proteases within the trypsin/chymotrypsin class of enzymes. Members of that class include, but are not limited to, elastase, chymotrypsin, and the serine proteases trypsin, thrombin, factor Xa, and factor VIIa. With respect to the inhibitors within the present invention directed at serine proteases acting within the coagulation cascade, e.g. inhibitors of thrombin, factor Xa and factor VIIa, such have in vitro and in vivo utilities as provided hereinabove for thrombin inhibitors.

Elastase has been implicated in a variety of conditions, including pulmonary hypertension (Rabinovitch, M., Acta Paediatr. Jpn 37:657–666 (1995)), idiopathic pulmonary fibrosis, rheumatoid arthritis, adult respiratory distress syndrome, cystic fibrosis, and other inflammatory diseases and conditions (Doring, G., Am. J. Respir. Crit. Care Med. 150: S114–S117 (1994)). Inhibition of elastase was shown to prevent or retard progression of pulmonary hypertension (Rabinovitch). Thus, inhibitors of the present invention directed toward elastase are useful as pharmaceutical compositions for the inhibition of elastase in conditions where elastase activity is associated with a pathological condition.

Elevated levels of chymotrypsin and trypsin are associated with the pathological effects resulting from pancreatitis (see U.S. Pat. No. 5,534,498). Animal studies of chemically-induced pancreatitis suggest that the disorder is rooted in the inability of pancreatic acinar cells to excrete digestive proenzymes, resulting in activation of trypsinogen to trypsin by lysosomal hydrolases within the cell. The amount of trypsin produced exceeds protective levels of protease inhibitor normally available.

The elevated levels of trypsin then cause activation of the other digestive enzymes co-localized with trypsin in the lysosome, such as chymotrypsin. The net effect of the enzyme activation is pancreatitis, which is characterized by damage to the pancreas and surrounding tissues from auto-digestion of the cells by the various digestive enzymes. These activated digestive enzymes also cause edema, interstitial hemorrhage, vascular damage, coagulation necrosis, fat necrosis and parenchymal cell necrosis.

Inhibitors of the present invention directed toward either trypsin or chymotrypsin, or ther members of the trypsin/chymotrypsin family that contribute to the deleterious effects of pancreatitis, are useful for the prevention and treatment of pancreatitis in mammals.

In addition to the in vivo utilities, inhibitors of the present invention also find utility in vitro. Inhibitors of enzymes within the coagulation cascade are useful inhibitors of blood coagulation in vitro, as described hereinabove. Inhibitors of other enzymes within the trypsin/chymotrypsin family, including trypsin, chymotrypsin, and elastase, are useful reagents in in vitro assays designed to measure the activity of such enzymes.

For instance, to determine or confirm the presence of active trypsin, chymotrypsin, or elastase in a sample, the activity of the enzyme in the sample is determined in the presence and absence of the specific inhibitor (which may be labeled using a radioactive or other detectable label). Lower activity measured in the presence of inhibitor as compared to in the absence of inhibitor demonstrates inhibition of the enzyme and, thus, its presence in the sample.

Similarly, the level of activity of an enzyme present in a sample is determined by adding inhibitor to the sample in a range of titrating doses, and calculating activity of the enzyme at each escalating dose of inhibitor. The concentration of inhibitor that completely inhibits the enzyme in the assay, along with knowledge of the assay parameters and characteristic of enzyme inhibition, allows one to calculate the activity of the enzyme in the sample.

The level of chymotrypsin measured in stool samples in vitro is used as an indicator of pancreatitis (Riedel, L. et al. Gut 32:321–324 (1991); Chari, S., Trop. Gastroenterol. 11:144–147 (1990)). Chymotrypsin inhibitors of the present invention are useful in such assays to evaluate the level of active chymotrypsin in such a sample, according to protocols such as those outlined hereinabove.

An additional use of the inhibitors of the present invention is their use to quench enzymatic reactions effected by the target enzyme. Thus, to control or prevent digestion of a sample with trypsin or chymotrypsin, an inhibitor of trypsin or chymoptrypsin, respectively, is added in inhibit the target enzyme and, thus, control or prevent digestion by that enzyme.

Certain compounds of the present invention can also be useful inhibitors of elastase, and are therefore useful pharmaceutical agents for the control of inflammation.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

Examples 1 to 11 describe preparation of compound 11 of FIG. 1.

Examples 12 to 14 describe preparation of compound 19 of FIG. 2.

Examples 15 to 19 describe preparation of intermediate 25 of FIG. 3.

Examples 20 to 22 describe preparation of compound 28 of FIG. 4.

Examples 24 to 30 describe preparation of compound 41 of FIG. 6.

Examples 31 to 33 describe preparation of compound 44 of FIG. 7.

EXAMPLES

Example 1

Preparation of N-(2-Hydroxy-4-methylphenyl)phthalimide (1)

A solution of phthalic anhydride (14.81 g, 0.10 mole) and 6-amino-m-cresol (12.32 g, 0.10 mole) in 200 mL of acetic acid was stirred at ambient temperature for 30 minutes and then refluxed for 6 hours. The solution was cooled and poured into 500 mL ice-water with rapid stirring and the resultant solid was collected by suction filtration, washed with ice-cold water several times and air dried overnight to afford 24.1 g (95% yield) of product 1 as a light brown solid, mp 251–254° C. TLC (silica ; EtOAc), Rf=0.68.

Example 2

Preparation of N-(2-Allyloxy-4-methylphenyl)phthalimide (2)

To a mixture of 1 (23.78 g, 0.0939 mole; see Example 1) and anhydrous $K_2CO_3$ (15.62 g, 0.113 mole) in 190 mL of anhydrous acetonitrile was added allyl bromide (17.04 g, 0.141 mole, 12.2 mL). The mixture was stirred under $N_2$ at room temperature for 15 minutes and then refluxed for 5 hours. The mixture was cooled, the solids were filtered and then washed with fresh acetonitrile/ethyl acetate, and the filtrate was evaporated. The residue was dissolved in 500 mL of ethyl acetate, extracted with 50 mL portions of saturated $NaHCO_3$ solution (2×), water, brine and dried over anhydrous $MgSO_4$. Filtration and removal of solvent afforded 26.76 g (97% yield) of product 2 as a light brown solid, mp 122–124°, judged pure by TLC (silica; $CH_2Cl_2$), Rf=0.45.

Example 3

Preparation of N-(2-Hydroxy-3-allyl-4-methylphenyl) phthalimide (3)

A solution of 2 (2.93 g, 0.010 mole; see Example 2) in 6 mL of N,N-dimethylaniline under $N_2$ was heated in an oil bath to 185° C. (pot temperature) for 1.5 hours and then cooled. The reaction mixture was poured onto a flash silica gel column and eluted directly with a hexane, $CH_2Cl_2$:2,1 to $CH_2Cl_2$ gradient solvent system to afford 2.79 g (95% yield) of product 3 as a colorless solid, mp 178–180° C. TLC (silica; $CH_2Cl_2$), Rf=0.25. Scale-up to 23.7 g and a reaction time of 2.5 hours afforded the product in 91% yield, identical in all respects with the above material.

Example 4

Preparation of N-(2-Benzyloxy-3-allyl-4-methyl-henyl) phthalimide (4)

To a mixture of 3 (6.60 g, 0.0225 mole; see Example 3) and anhydrous K2CO3 (3.73 g, 0.027 mole) in 45 mL of anhydrous acetonitrile was added benzyl bromide (5.00 g, 0.0293 mole, 3.49 mL). The mixture was stirred under $N_2$ at room temperature for 15 minutes and then refluxed for 19 hours. The mixture was cooled and filtered; the collected solids were washed with fresh acetonitrile and the filtrate was evaporated. The residue was dissolved in 300 mL of ethyl acetate and extracted with 50 mL portions of saturated $NaHCO_3$(2×), water, brine and dried over anhydrous $MgSO_4$. Filtration, solvent removal and recrystallization from 1-chlorobutane afforded product as a solid. The filtrate residue was flash chromatographed on silica gel, eluting with a hexane, $CH_2Cl_2$:2,1 to $CH_2Cl_2$ gradient to afford a total of 6.99 g (81% yield) 4 as a colorless solid, mp 107–109° C. TLC (silica; $CH_2Cl_2$, Hexane: 2,1), Rf=0.30.

Example 5

Preparation of 2-Benzyloxy-3-allyl-4-methylaniline (5)

To a solution of 4 (7.67 g, 0.020 mole; see Example 4) in 100 mL of ethanol was added hydrazine monohydrate (1.22 g, 0.024 mole, 1.18 mL). The reaction was stirred at room temperature under $N_2$ for 15 minutes, refluxed for 27 hours, cooled and filtered, and then the filtrate was evaporated. The residue was purified by flash chromatography on silica gel, using a hexane, ethyl acetate: 9,1 to 4,1 gradient and afforded 5.03 g (99% yield) of product 5 as a viscous light red-brown oil. TLC (silica; hexane, ethyl acetate: 2,1), Rf=0.45.

Example 6

Preparation of N-Benzylsulfonanilide, 2-benzyloxy-3-allyl-4-methyl- (6)

To a solution of 5 (7.54 g, 0.0298 mole; see Example 5) and 4-methylmorpholine (9.04 g, 0.0894 mole, 9.83 mL) in 300 mL of anhydrous acetonitrile at 0° C. under N2 was added α-toluene-sulfonyl chloride (11.36 g, 0.0596 mole) in one portion. The solution was stirred at 0° C. for 1 hour and allowed to warm to and stir at ambient temperature for 19 hours. The solution was filtered and evaporated. The crude residue was purified by flash chromatography on silica gel using a hexane, $CH_2Cl_2$: 4,1 to $CH_2Cl2$ gradient system and afforded 12.05 g (99% yield) of product 6 as waxy reddish solid, mp 62–63° C. TLC (silica; $CH_2Cl_2$), Rf=0.45.

Example 7

Preparation of 2-Benzyloxy-3-(N-benzylsulfonylamino)-6-methylphenylacetaldehyde (7)

A stream of ozone gas was introduced into a solution of 6 (10.71 g, 0.0263 mole; see Example 6) dissolved in 260 mL of methanol at −78° C. until a pale blue color persisted.

After 3 minutes, a stream of dry $N_2$ was bubbled through the solution to discharge excess ozone. Dimethyl sulfide (3.27 g, 0.0526 mole, 3.86 mL) was added, the solution was stirred at −78° C. for 5 minutes, and was allowed to warm to and then stir at ambient temperature for 14 hours. The solvent was evaporated to afford a residue which was dissolved in 350 mL of diethyl ether, extracted with 50 mL portions of water (2×), brine, dried over anhydrous $MgSO_4$, filtered and evaporated to afford 11.73 g of a viscous oil. This oil was dissolved in 245 mL acetone and 75 mL of 1N HCl was added. The solution was stirred at room temperature for 14 hours, refluxed for 30 minutes, cooled and evaporated. The residue was dissolved in 600 mL of diethyl ether and extracted with 50 mL portions of saturated $NaHCO_3$, water (2×), brine, and dried over $MgSO_4$. Filtration and solvent removal afforded 9.71 g (98% yield) of product 7 as a viscous yellow oil. TLC (silica; hexane, ethyl acetate: 2,1), Rf=0.25.

Example 8
Preparation of 2-Benzyloxy-3-(N-benzylsulfonylamino)-6-methylphenylacetic acid (8)

To a solution of 7 (9.70 g, 0.0237 mole; see Example 7) in 250 mL of acetone at 0° C. was added Jones' reagent rapidly dropwise over a 30 minute period until a brown color persisted. The ice bath was removed and the mixture was allowed warm to room temperature. 2-Propanol (15 mL) was added and the mixture was stirred for 10 minutes. The mixture was diluted with 500 mL of ethyl acetate and filtered with suction through a pad composed of a homogeneous 1:1 mixture of celite and flash-grade silica gel. Elution with an additional 1 liter portion of acetone, ethyl acetate 1,1, followed by solvent removal afforded 10.30 g (~Quantitative crude yield) of product 8 as a sticky yellow foam, judged nearly pure by TLC (silica; $CH_2Cl_2$, EtOH: 9,1), Rf=0.53. A portion recrystallized from diethyl ether and hexane afforded a colorless solid, mp 132–134° C.

Example 9
Preparation of N-2-Benzyloxy-3-(N-benzylsulfonylamino)-6-methylphenylacetyll-$N^g$-nitro-L-arpininal Ethyl Cyclol (9)

To a solution of 8 (9.16 g, 0.02153 mole; see Example 8) in 215 mL of anhydrous acetonitrile at room temperature under $N_2$ was added $N^g$-nitro-L-argininal ethyl cyclol (6.92 g, 0.0258 mole), 1-hydroxybenzotriazole hydrate (3.30 g, 0.0215 mole) and 1-ethyl-3-(3-dimethylaminopropyl) carbodiimide hydrochloride (6.19 g, 0.0323 mole). After stirring the mixture for 15 minutes, N,N-diisopropylethylamine (11.13 g, 0.0861 mole, 15.0 mL) was added and the resultant clear light brown solution was stirred at room temperature for 22 hours. The solvent was evaporated, the residue was slowly dissolved in 700 mL of ethyl acetate and was extracted with 50 mL portions of 1N HCl (3×), saturated $NaHCO_3$ (2×), water (2×), brine(2×), dried over $MgSO_4$, filtered and evaporated. The crude product was purified by flash chromatography on silica gel using a $CH_2Cl_2$, EtOH: 99,1 to 95,5 gradient system to afford 9.49 g (69% yield) of product 9 as a light yellow foam. TLC (silica; ethyl acetate), Rf=0.50.

Example 10
Preparation of N-[2-Hydroxy-3-(N-benzylsulfonylamino)-6-methylphenylacetyl]-L-araininal Ethyl Cyclol Acetate Salt (10)

To a solution of 9 (9.27 g, 0.0145 mole; see Example 9) in 370 mL of ethanol, acetic acid, water: 4,1,1 was added 10% Pd/C (9.3 g). The mixture was hydrogenated at 60 PSI on a Parr shaker apparatus for 20 hours. The mixture was filtered and the solvents were evaporated. The residue was dissolved in ethanol, acetonitile 1,1, reevaporated, and pumped at <1 mm Hg on a vacuum pump for 24 hours to afford 7.23 g (89% yield) of product 10 as a yellow foam. TLC (silica; $CH_2Cl_2$, methanol, conc $NH_{40}H$: 20, 10, 2), Rf=0.50.

Example 11
Preparation of N-[2-Hydroxy-3-(N-benzylsulfonylamino)-6-methylphenylacetyl]-L-araininal Trifluoroacetate Salt (11)

Compound 10 (1.01 g, 1.78 mmole; see Example 10) was added to a solution of 35 mL of 9.4 M $HClO_4$ at 0° C. The starting material slowly dissolved over 30 minutes and the reaction mixture was then frozen by immersion in a dry-ice acetone slurry. After warming to −15° C., the reaction mixture was adjusted to pH 5 by using a 10 M NaOH solution followed by a saturated NaOAc solution. During the neutralization process, the temperature was maintained at <10° C. The solution was stored at 4° C. for one hour, then the solids were filtered. The filtrate was purified by reverse phase HPLC on a 50×300 mm C18 column using a 0 to 28% gradient of acetonitrile/water (containing 0.1% trifluoroacetic acid) over one hour to afford 0.66 g (63% yield) of product 11 as a colorless, amorphous solid. RP/HPLC analysis showed three peaks for the product. Mass spectrometry confirmed the theoretical molecular weight of 475.

Example 12
Preparation of N-(2-Methoxy-3-allyl-4-methylphenyl)-phthalimide (12)

To a mixture of 3 (6.00 g, 0.0205 mole; see Example 3) and anhydrous $K_2CO_3$ (3.39 g, 0.025 mole) in 41 mL of anhydrous acetonitrile was added iodomethane (5.81 g, 0.0409 mole, 2.54 mL). The mixture was stirred under $N_2$ at room temperatrure for 15 minutes and then refluxed for 17 hours. The mixture was cooled and filtered, the collected solids were washed with fresh acetonitrile and the filtrate was evaporated to afford 5.08 g (81% yield) of pure 12 as a colorless solid. TLC (silica; Hexane, ethyl acetate:1,1), Rf=0.50.

Example 13
Preparation of N-[2-Methoxy-3-(N-benzylsulfonylamino)-6-methylphenylacetul]-L-argininal Ethyl Cyclol Acetate Salt (18)

Compound 18 was prepared from compound 12 by following an analogous six-step protocol outlined above for the preparation of compound 10 from compound 4 (hydrazinolysis, benzylsulfonation, ozonolysis, oxidation, coupling and hydrogenation; see Examples 5 to 10).

Example 14
Preparation of N-[2-Methoxy-3-(N-benzylsulfonylamino)-6-methylphenylacetyl]-L-argininal Trifluoroacetate Salt (19)

Compound 18 (1.00 g, 1.73 mmole) was added to a solution of 72 mL of 3N HCl and 5 mL of acetonitrile. The mixture was stirred at room temperature for 2 hours, 10.0 mL of 6N HCl was added, and reaction was continued for a further 3.5 hours. The solution was filtered and purified by reverse phase HPLC on a 50×300 mm C18 column using a 5 to 30% gradient of acetonitrile/water (containing 0.1% trifluoroacetic acid) over one hour and afforded 0.77 g (74% yield) of product 19 as a colorless, amorphous solid. RP/HPLC analysis showed three peaks for the product. Mass spectrometry confirmed the theoretical molecular weight of 489.

Example 15
Preparation of N-(t-butoxycarbonyl)-3-(3-pyridyl)-L-alanine methyl ester (21)

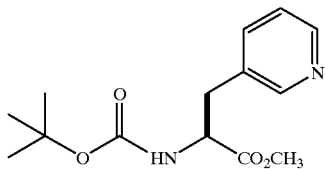

To a solution of N-(t-butoxycarbonyl)-3-( 3-pyridyl) alanine (20) (5.0 g, 18.8 mmole) in methanol (100 mL) was added thionyl chloride (2M solution in dichloromethane, 66 mL, 132 mmole). The resulting solution was stirred overnight at ambient temperature. The methanol was removed under reduced pressure to a minimum volume and ethyl acetate (100 mL) was added. The resulting white precipitate was collected in a fritted funnel. To a solution of the collected precipitate in a mixture of tetrahydrofuran/water (40 mL each) was added di-tert-butyl dicarbonate (4.8 g, 21.99 mmole) and sodium carbonate (1.95 g, 18.4 mmole). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This product was subjected to flash column chromatography on silica gel (230–400 mesh) using a 8×52 cm column and eluting with a 10:90 mixture of ethyl acetate/hexane followed by a 60:40 mixture of ethyl acetate/hexane. 4 g (74%) of the title compound was obtained as an oil. Thin-layer chromatography (silica gel; ethyl acetate), $R_f$=0.68.

Example 16
Preparation of N-(t-butoxycarbonyl)-3-([R,S]-3-piperidyl)-L-alanine methyl ester, acetate salt (22)

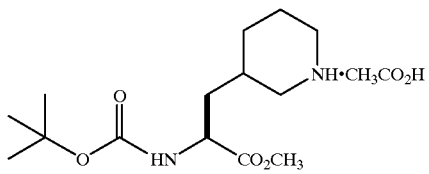

A solution of the compound of Example 15 (5 g, 17.8 mmole) in ethanol (24 mL), acetic acid (6 mL) and water (6 mL) was hydrogenated over platinum oxide (500 mg) at 45 psi for three hours. The catalyst was filtered off and the filtrate concentrated under vacuum to an oily residue (6.89 g) which was used in the next step (Example 17) without further purification. Thin-layer chromatography yielded two spots corresponding to two diastereomers with $R_f$ values of 0.16 and 0.26, respectively (silica gel; 4:1:1 n-butanol/acetic acid/water).

Example 17

Preparation of N-(t-butoxycarbonyl)-3-[(R,S)-3-piperidyl-(N-guanidino (bis-benzyloxycarbonyl))]-L-alanine methyl ester (23)

To a solution of the compound of Example 16 (6.89 g, 19.9 mmole) in tetrahydrofuran (80 mL) was added S-methylisothiourea bis-benzyloxycarbonyl (7.13 g, 19.9 mmole) followed by N-methylmorpholine (4.37 mL), and the reaction mixture was stirred at ambient temperature for 18 hours. The reaction mixture then was concentrated under vacuum and the resulting residue was dissolved in ethyl acetate (100 mL) and washed with 1N sodium bisulfate and saturated sodium chloride (50 mL each). After drying over anhydrous sodium sulfate, the solvents were removed under vacuum; the crude title compound was subjected to flash column chromatography on silica gel (230–400 mesh) using a 8×52 cm column and eluting with 1:9 ethyl acetate/hexanes (two column volumes) followed by 1:1 ethyl acetate/hexanes. 2.75 g the title compound was obtained as a mixture of two diastereomers. Thin-layer chromatography gave two spots with $R_f$ values of 0.57 and 0.62, respectively (silica gel; 1:1 ethyl acetate/hexanes).

Example 18
Preparation of N-(t-butoxycarbonyl)-3-[(R,S)-3-piperidyl-(N-auanidino (bis-benzyloxycarbonyl))]1-L-alaninol (24)

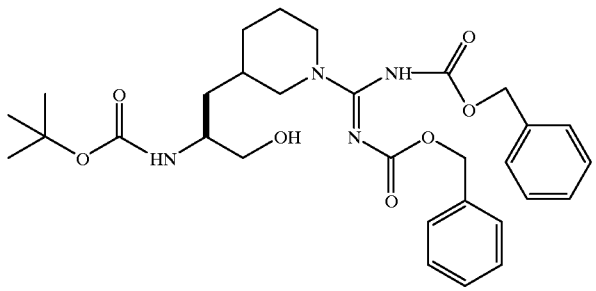

To a stirred solution of the compound of Example 17 (2.23 g, 3.7 mmole) in absolute ethanol (8 mL) and anhydrous tetrahydrofuran (4 mL) was added calcium chloride (844 mg, 7.6 mmole) and sodium borohydride (575 mg, 15.2 mmole). After stirring 12 hours at ambient temperature, the reaction mixture was concentrated under vacuum and the resulting residue was partitioned between ethyl acetate and 1N sodium bisulfate (10 mL each). The two layers were separated; organic layer was washed twice more with 1N sodium bisulfate, dried over anhydrous sodium sulfate and concentrated under vacuum gave a residue. Flash column chromatography of the residue on silica gel (230–400 mesh) using a 5.5×45 cm column and eluting with ethyl acetate gave 1.3 g of the title compound as a white foam. Thin layer chromatography yielded two spots corresponding to two diastereomers with Rf values of 0.18 and 0.27, respectively (silica gel; 1:1 ethyl acetate/hexanes).

Example 19
Preparation of 3-[(R,S)-3-piperidyl-(N-gruanidino(bis-benzyloxycarbonyl))]-L-alaninol, hydrochloride salt (25)

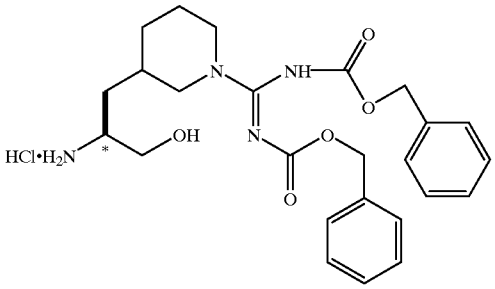

The compound of Example 18 (290 mg, 0.57 mmole) was treated with 2.5 N anhydrous hydrochloric acid in ethyl acetate (2.0 mL) at ambient temperature for one hour. The solvent was removed under vacuum to a sticky-white solid (260 mg). This solid was used in the next step (Example 9) without further purification. $^1$H NMR spectrum taken in $CD_3OD$ showed no t-butoxycarbonyl protons at 1.4 ppm.

Example 20
Preparation of N-[2-Hydroxy-3-(N-benzylsulfonylamino)-6-methylphenyl-acetyl]-3-[(R,S)-3-piperidyl-(N-guanidino (bis-benzyloxycarbonyl))]-L-alaninol (26)

To a suspension of the Compound of Example 19 (25) (2.06 g, 4.08 mmole) in acetonitrile (22 mL) is added successively the compound of Example 8 (8) (2.36 g, 5.56 mmole), EDC (1.12 g, 5.84 mmole), 1-hydroxybenzotriazole hydrate (979 mg, 6.39 mmole), and N-methylmorpholine (3 mL, 27.80 mmole). The solution is stirred at ambient temperature for about twenty hours. The solvent is removed under vacuum and the resulting residue is dissolved in a 9:1 mixture of dichloromethane/isopropanol (40 mL) and washed two times each with 15 mL portions of 1N sodium bisulfate, saturated sodium bicarbonate and saturated sodium chloride. The organic layer is dried over anhydrous sodium sulfate and concentrated under vacuum to give the title compound. The product is a mix of diastereomers at P1 and has a calculated molecular weight of 875.05.

Example 21
Preparation of N-[2-Hydroxy-3-(N-benzylsulfonylamino)-6-methylphenyl-acetyl]-3-[(R,S)-3-piperidinyl-(N-guanidino)]-L-alaninol (27)

The compound of Example 20 (26) (1.97 g, 2.25 mmole) is subjected to catalytic hydrogenation in methanol (100 mL) and acetic acid (10 mL in the presence of 10% palladium on carbon (185 mg) at 30 psi for about 2.5 hours. The catalyst is filtered. The filtrate after concentration under vacuum yields the title compound as two diastereomers with a calculated molecular weight of 577.7.

Example 22
Preparation of N-[2-Hydroxy-3-(N-benzylsulfonylamino)-6-methylphenyl-acetyl]-3-[3-piperidinyl-(N-guanidino)-L-alaninal and separation of diasteromers (28a and 28b)

To a chilled solution of the compound of Example 21 (27) (0.81 g, 1.4 mmole) in dimethylsulfoxide and toluene (15 mL each) is added dichloroacetic acid (567 μL, 6.9 mmole), followed by EDC (2.68 g, 14 mmole) at one minute later. The reaction mixtue is stirred for about 5 minutes at 0° C., then about 85 minutes at ambient temperature, and then is quenched with 60 mL water. The water layer is extracted twice with diethyl ether (10 mL portions) and subjected to HPLC using a 47×300 mm reverse phase column continuing a C-18 resin comprised of 10 micron-size gel particles with a 300 angstrom pore size. The column is eluted with a gradient ranging from 15% to 30% acetonitrile in water (containing 0.1% trifluoroacetic acid). The HPLC fractions will yield fast moving and slow moving peaks containing the two diastereomers of the title compound. The fractions containing each diastereomer when pooled, then lyophilized, will give the two diastereomers of the title compound, (28a and 28b).

Example 23
Preparation semicarbazid-4-yl diphenylmethane, trifluoroacetate salt

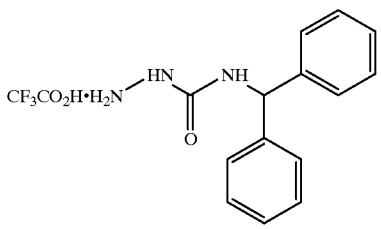

Step 1:

A solution of carbonyldiimidazole (16.2 g, 0.10 mole) in 225 mL of dimethylformamide was prepared at room temperature and allowed to stir under nitrogen. A solution of t-butyl carbazate (13.2 g, 0.100 moles) in 225 mL dimethylformamide was then added dropwise over a 30 minute period. Next, diphenylmethylamine (18.3 g, 0.10 moles) was added over a 30 minute period. The reaction was allowed to stir at room temperature under nitrogen for one hour. Water (10 mL) was added and this mixture was concentrated to about 150 mL under vacuum. This solution was poured into 500 mL water and extracted with 400 mL of ethyl acetate. The ethyl acetate phase was extracted two times each with 75 mL 1N HCl, water, saturated sodium bicarbonate and brine, and then was dried with anhydrous magnesium sulfate. The mixture was filtered and the solution was concentrated to give 29.5 g (85% yield) of 1-t-butoxycarbonyl-semicarbazid-4-yl diphenylmethane as a white foam. This material may be purified by recrystallization from ethyl acetate/hexane, but was pure enough to use directly in step 2: mp 142–1430C. $^1$H NMR (CDCl$_3$) delta 1.45 (s, 9H), 6.10 (dd, 2H), 6.42 (s, 1H), 6.67 (bs, 1H), 7.21–7.31 (m, 10H). Analysis calculated for C$_{19}$H$_{23}$N$_3$O$_3$: C, 66.84; H, 6.79; N, 12.31. Found: C, 66.46; H, 6.75; N; 12.90.

Step 2:

A solution of 3.43 g (10 mmole) of 1-t-butoxycarbonyl-semicarbazid-4-yl diphenylmethane in 12.5 mL of dichloromethane was treated with 12.5 mL of trifluoroacetic acid at 0° C. The reaction mixture was allowed to stir for 30 minutes at this temperature. The reaction mixture was then added dropwise to 75 mL of diethyl ether to give a precipitate. The resulting precipitate was filtered off and washed with diethyl ether to give 2.7 g (80% yield) of the title compound; mp 182–184° C.

Example 24
Preparation of 3-thioamidobenzyl-N-acetylaminomalonic acid diethyl ester (35)

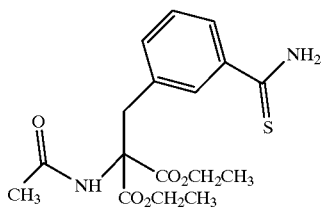

To a stirred solution of alpha-bromo-meta-tolunitrile (32) (45.0 g, 0.24 mole), diethyl acetamidomalonate (33) (48.0 g, 0.22 mole) and potassium iodide (3.0 g, 0.018 mole) in dioxane (500 mL) was added 2.5M sodium ethoxide in ethanol (100 mL) dropwise under an argon atmosphere. After the addition was complete, the solution was refluxed for 6 hours. The reaction mixture was allowed to stand overnight at room temperature, then diluted with brine (250 mL) and water (250 mL), and extracted with ethyl acetate four times (1.0 L total). The combined extracts were washed with water (100 mL), 10% citric acid (100 mL), water (100 mL) and brine (2×50 mL), then dried over anhydrous magnesium sulfate and filtered; the solvent was removed under vacuum. The crude residue was recrystallized from ethyl acetate and diethyl ether in two crops to yield 43.51 g (60%) of the 3-cyanobenzyl-N-acetylaminomalonic acid diethyl ester (34) as yellow crystals.

H$_2$S(g) was bubbled into a rapidly stirring solution of 3-cyanobenzyl-N-acetylaminomalonic acid diethyl ester (44.3 g, 0.13 mmole) in pyridine (300 mL) and triethylamine (100 mL) for 40 minutes. The reaction mixture was stirred at room temperature for 16 hours, then poured into 3.0 L of water. A yellow precipitate formed immediately. The solution was allowed to stand at 4° C. for 4 hours, then was filtered. The crude title compound was recrystallized from ethyl acetate and hexanes to yield 48.1 g (98%) of the title compound as yellow crystals, m.p. 183–186° C. $^1$H NMR (CDCl$_3$): delta 1.31 (t, J=7.1 Hz, 6H), 2.06 (s, 3H), 3.70 (s, 2H), 4.29 (q, J=7.1 Hz, 4H), 4.80–4.87 (m, 1H), 6.60 (s, 1H), 7.10–7.20 (m, 1H), 7.27–7.35 (m, 2H), 7.60–7.70 (m, 2H). Analysis calculated for C$_{17}$H$_{22}$N$_2$O$_5$S: C, 55.72; H, 6.05; N, 7.64. Found: C, 55.55; H, 5.96; N, 7.76.

Example 25
Preparation of 3-amidino-D,L-phenylalanine, dihydrochloride salt (36)

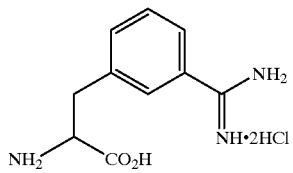

The compound of Example 24 (35) (48.1 g, 0.13 mmole) was dissolved in acetone (800 mL). Iodomethane (18.3 mL, 0.19 mole, 1.5 equivalents) was added, and the solution was refluxed for 30 minutes. The solution was cooled to room temperature, and the intermediate thioimidate was filtered, dried and dissolved in methanol (500 mL). Ammonium acetate (14.8 g, 0.19 mole, 1.5 equivalents) was added. The reaction mixture was refluxed for 1 hour, then cooled to room temperature, and poured into ether (1.2 L). The solution was allowed to stand at 4° C. for 72 hours. The crude 3-amidinobenzyl-N-acetylaminomalonic acid diethyl ester was filtered, washed with ether, air dried, and then refluxed in concentrated HCl (250 mL) for 3 hours. The reaction mixture was concentrated under vacuum, diluted with water (0.5 L), and concentrated under vacuum again. These steps were repeated. The crude title compound was purified by cation-exchange (Sephadex SP-C25) using a gradient of 0–1.0N HCl as eluent to yield 10.8g (30%) of the title compound as an off-white solid. $^1$H NMR (D$_2$O): delta 3.14–3.29 (2H, m), 4.17 (dd, J=7.4, 6.2 Hz, 1H), 7.42–7.69 (4H, m). Analysis calculated for C$_{10}$H$_{13}$N$_3$O$_2$·2HCl·1.9H$_2$O: C, 38.20; H, 6.03; N, 13.36. Found: C, 38.51; H, 5.64; N, 12.89.

Example 26
Preparation of N-alpha-Boc-N-ω-4-methoxy-2,3,6-trimethylbenzenesulfonyl-3-amidino-D,L-Dhenylalanine (37)

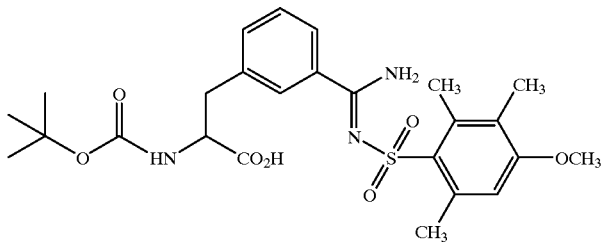

3-amidino-D,L-phenylalanine (the compound of Example 25, (36)) (4.00 g, 13 mmole) was dissolved in 50% aqueous dioxane (20 mL). Sodium bicarbonate (3.38 g, 40 mmole) was added, followed by di-t-butyl dicarbonate (2.93 g, 13 mmole) in dioxane (4 mL). The reaction mixture was stirred for 18 hours at room temperature. The solution was cooled in an ice bath, and 4.0 N sodium hydroxide was added dropwise until the solution was pH 12. 4-methoxy-2,3,6-trimethylbenzenesulfonyl chloride (8.01 g, 32 mmole) in dioxane (10 mL) was added dropwise. 4.0 N sodium hydroxide was added as needed to keep the pH at 12. The ice bath was removed. After 1 hour, 1.0 N HCl was added to bring the solution to pH 7–8. The solution was diluted with an additional 50 mL of water and then was washed with ethyl acetate two times (20 mL each). The aqueous layer was acidified to pH 1.0 with 1.0 N HCl and extracted with ethyl acetate three times (100 mL total). The combined organic layers were washed with water (20 mL) and brine twice (10 mL each). The organic layer was dried over anhydrous magnesium sulfate and the solvent was removed under vacuum. The residue was dissolved in a minimum amount of dichloromethane, then added dropwise to ether (25 mL). Solid impurities were removed by filtering and the solvent removed from the filtrate under vacuum to give 4.90 g (68% crude yield) of the title compound as an off-white foam. A 30 mg sample of the title compound was further purified by preparative thin-layer chromatograph developing with 1% acetic acid/5% isopropanol/dichloromethane to give 9 mg of the title compound in a purer form. Rf=0.16 (1% acetic acid/5% isopropanol/dichloromethane). $^1$H NMR (CD$_3$OD): delta 1.32 (s, 9H), 2.14 (s, 3H), 2.63 (s, 3H), 2.71 (s, 3H), 2.93 (dd, J=13.7, 9.3 Hz, 1H), 3.22 (dd, J=13.7, 4.3 Hz, 1H), 3.85 (s, 3H), 4.34–4.37 (m, 1H), 6.72 (s, 1H), 7.35–7.47 (2H, m), 7.69–7.75 (m, 2H).

Example 27
Preparation of N-alpha-Boc-N-ω-4-methoxy-2,3,6-trimethylbenzenesulfonyl-3-amidino-D,L-phenylalanine-N-methyl-O-methyl-carboxamide (38)

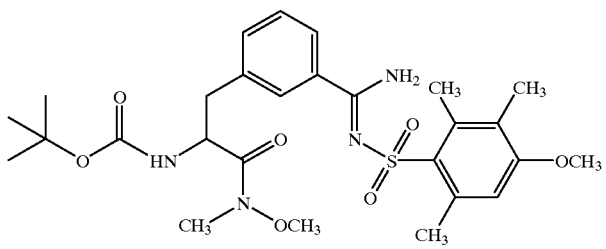

To a stirred solution of compound of Example 26 (37) (1.00 g, 1.92 mmole), O,N-dimethyl hydroxylamine hydrochloride (375 mg, 3.85 mmole), hydroxybenzotriazole hydrate (294 mg, 1.92 mmole) and 4-methylmorpholine (1.06 mL, 9.62 mmole) in tetrahydrofuran (4 mL), cooled in an ice bath, was added EDC (406 mg, 2.12 mmole). The ice bath was removed, and the reaction mixture was stirred for 2 hours at room temperature. The reaction mixture was diluted with ethyl acetate (75 mL), washed with water, 10% citric acid, water, saturated sodium bicarbonate, and brine. The organic layer was dried over anhydrous magnesium sulfate and the solvent was removed under vacuum. 750 mg (69%) of the title compound was isolated. $^1$H NMR (CDCl$_3$): delta 1.33 (s, 9H), 2.14 (s, 3H), 2.66 (s, 3H), 2.75 (s, 3H), 2.80–2.88 (m, 1H), 3.06–3.20 (m, 4H), 3.70 (s, 3H), 3.84 (s, 3H), 4.98–5.06 (m, 1H), 5.21 (d, J=8.7 Hz, 1H), 6.48 (bs, 1H), 6.58 (s, 1H), 7.30–7.34 (m, 2H) 7.60–7.68 (m, 2H), 8.11 (bs, 1H). Analysis calculated for C$_{27}$H$_{38}$N$_4$O$_7$S.0.5H$_2$O: C, 56.73; H, 6.88; N, 9.80. Found: C, 56.97; H. 6.66; N, 9.43.

Example 28

Preparation of N-alpha-Boc-N-ω-4-methoxy-2,3,6-trimethylbenzenesulfonyl-D,L-3-amidinophenylalaninal (39)

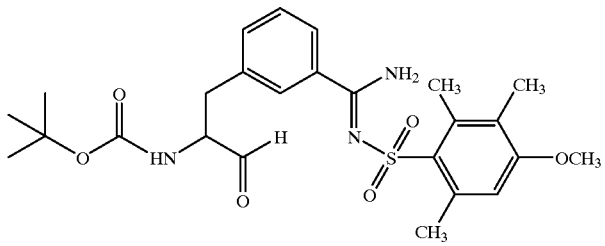

To a stirred solution of LiAlH$_4$ (2.00 mL of a 1.0 M solution in tetrahydrofuran, 1.24 mmole) in tetrahydrofuran (8 mL), cooled in a dry ice/acetone bath, the compound of Example 27 (38) (0.75 g, 1.9 mmole in tetrahydrofuran (5 mL)) was added dropwise. The cooling bath was removed and the reaction mixture was allowed to warm to 5° C. The reaction mixture was re-cooled in the dry ice acetone bath and quenched with 3.0 mL of a 1:2.7 wt./wt. solution of potassium bisulfate in water. The reaction mixture was allowed to warm to room temperature, stirred for 3 hours, filtered and concentrated under vacuum. The residue was dissolved in ethyl acetate (20 mL), and washed with 10% citric acid (2 mL), water (2 mL), saturated sodium bicarbonate (2 mL) and brine (2 mL). The organic layer was dried over anydrous magnesium sulfate and the solvent was removed under vacuum to yield 580 mg (86%) of the title compound. $^1$H NMR (CDCl$_3$): delta 1.31 (s, 9H), 2.07 (s, 3H), 2.57 (s, 3H), 2.67 (s, 3H),2.90–3.17 (2H, m), 3.77 (s, 3H), 4.33–4.40 (1H, m), 5.02–5.08 (1H, m), 6.48 (1H, s), 7.23–7.31 (2H, m), 7.50–7.62 (2H, m), 7.94, (1H, bs), 8.05 (1H, bs), 9.55 (1H, s). Analysis calculated for C$_{25}$H$_{33}$N$_3$O$_6$S.0.5H2O: C, 58.58; H, 6.69; N,8.20. Found: C, 58.57; H, 6.72; N, 7.98.

Example 29

Preparation of N-alpha-Boc-N-ω-4-methoxy-2,3,6-trimethylbenzenesulfonyl-D,L-3-amidinophenylalaninal-semicarbazonyl-4-N-diphenylmethane (40)

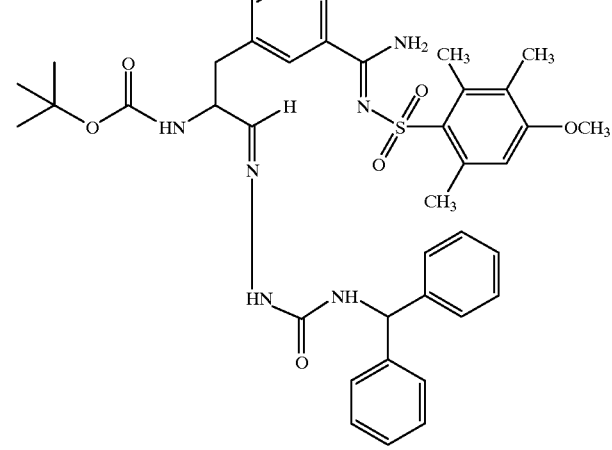

The compound of Example 28 (39) (0.58 g, 1.9 mmole), the compound of Example 23 (410 mg, 1.15 mmole) and sodium acetate trihydrate (188 mg, 1.38 mmole) were refluxed in 75% aqueous ethanol (10 mL) for 1 hour. After the reaction mixture was cooled to room temperature, it was diluted with ethyl acetate (50 mL), washed with 1.0N HCl (5 mL), water (5 mL), saturated sodium bicarbonate (5 mL) and brine (2×5 mL), and dried over anhydrous magnesium sulfate. The solvent was removed under vacuum to yield 750 mg (89% yield) of the title compound as an off-white foam. Analysis calculated for C$_{39}$H$_{46}$N$_6$O$_6$S.1.0 H$_2$O: C, 62.88; H, 6.49; N, 11.28. Found: C, 63.14; H, 6.35 N, 11.10. Calculated molecular weight was 726.90.

Example 30
Preparation of N-ω-4-methoxv-2,3,6-trimethylbenzene sulfonyl-D,L-3-amidino-henylalaninal-semicarbazonyl-4-N-dithenylmethane, trifluoroacetate salt (41)

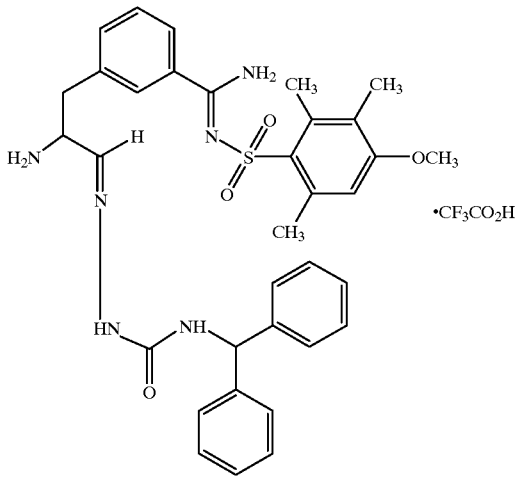

The compound of Example 29 (40) (750 mg, 1.9 mmole) was treated with 50% trifluoroacetic acid/dichloromethane (3 mL) for 30 minutes at room temperature. The reaction mixture was added dropwise to ether (50 mL). The solution was allowed to stand at 4° C. for 18 hours. The product was filtered, and dried under vacuum to yield 600 mg (79% yield) of the title compound as an off-white solid. Analysis calculated for $C_{34}H_{38}N_6O_4S \cdot 1.3CF_3CO_2H$: C, 56.72; H, 5.11; N, 10.84. Found: C, 56.34; H, 5.47; N, 11.49. The salt had a calculated molecular weight of 740.8.

Example 31
Preparation of N-[2-Benzyloxy-3-(N-benzylsulfonylamino)-6-methylphenyl-acetyl]-D,L-N-ω-4-methoxy-2,3,6-trimethylbenzenesulfonyl-D,L-3-amidinoihenylalaninal-semicarbazonyl-4-N-diphenylmethane (42)

EDC (180.1 mg, 0.94 mmole) is added in one portion to a stirred solution of the compound of Example 8 (8) (209 mg, 0.49 mmole), hydroxybenzotriazole (75 mg, 0.49 mmole), and 4-methylmorpholine (0.24 mL, 2.2 mmole) in dimethylformamide (5 mL) with cooling in an ice bath. After 30 minutes, the compound of Example 30 (41) (363 mg, 0.49 mmole) is added. After an additional 22 hours, the reaction mixture is diluted with water (25 mL) and brine (25 mL). The product is filtered and dissolved in ethyl acetate (125 mL). The solution is washed with 10% citric acid, water, saturated sodium bicarbonate and brine, and is dried over anhydrous magnesium sulfate. The solvent is removed under vacuum. The resulting residue is chromatographed by flash chromatography on silica gel to give the title compound.

Example 32
Preparation of N-[2-Hydroxy-3-(N-benzyl-sulfonylamino)-6-methyl-phenyl-acetyl-D,L-3-amidinophenylalaninal semicarbazone (43)

The compound of Example 31 (42) (100 mg) is treated with hydrofluoric acid/anisole (9:1) for 30 minutes at −20° C. and 0° C. for 30 minutes. After removal of the hydrofluoric acid, the resulting residue is dissolved in 20% aqueous acetic acid and washed with diethyl ether. The aqueous layer is lyophilized to a powder, then is purified by preparative HPLC (C-18, eluting with 10–40% acetonitrile-water gradient containing 0.1% trifluoroacetic acid) to give the title compound.

Example 33
Preparation of N-[2-Hydroxy-3-(N-benzylsulfonylamino)-6-methylphenylacetyl]-D,L-3-amidinophenylalaninal (44)

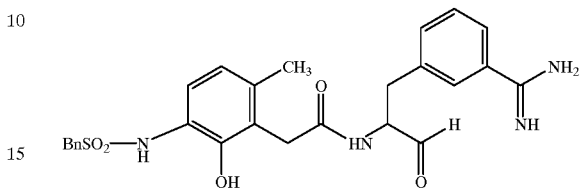

The compound of Example 32 (43) (50 mg, 32 micromoles) is dissolved in methanol (1 mL) and 1% aqueous trifluoroacetic acid (5 mL), then formalin (0.23 mL) is added. After 40 minutes, the solution is filtered through a 2 micron filter, diluted to a volume of 15 mL with water, and then is purified by preparative HPLC (C-18, eluting with 10–40% acetonitrile-water gradient containing 0.1% trifluoroacetic acid). The fractions containing the title compound are pooled and lyophilized to give the title compound.

Example A
Kinetic Analysis of Compounds in an in vitro Thrombin Inhibition Assay The ability of the compounds of Example 11 and 14 to act as an inhibitor of thrombin catalytic activity was assessed by determining the compounds, inhibition constant, Ki.

Enzyme activity was determined using the chromogenic substrate Pefachrome t-PA ($CH_3SO_2$-D-hexahydrotyrosine-glycyl-L-arginine-p-Nitroanilide), obtained from Pentapharm Ltd. The substrate was reconstituted in deionized water prior to use. Purified human alpha-thrombin (3000U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for Ki determinations was conducted by combining in appropriate wells of a Corning microtiter plate, 100 microliters of HBSA or the test compound at a specified concentration diluted in HBSA (or HBSA alone for $V_O$ (uninhibited velocity) measurement), and 100 microliters of the chromogenic substrate (750 μM, 5× Km). At time zero, 50 microliters of alpha-thrombin diluted in HBSA were added to the wells, yielding a final concentration of 0.2 nM in a total volume of 250 microliters. Velocities of chromogenic substrate hydrolysis which occurred over 60 minutes were measured by the change in absorbance at 405 nm using a Thermo Max® Kinetic Microplate Reader. Ki values were determined for test compounds using the relationships developed by Williams and Morrison, Methods in Enzymology, 63: 437 (1979) using steady state velocities ($V_s$) measured over 60 minutes. The extent of substrate hydrolysis was less than 5% over the course of this assay.

Table 1 below gives the Ki values for the compounds of Examples 11 and 14. The data show the utility of these compounds as potent in vitro inhibitors of human alpha-thrombin.

TABLE 1

| Compound | Ki (nM) |
| --- | --- |
| Compound of Example 11 | 0.79 |
| Compound of Example 14 | 1.0 |

Example B
In vitro Enzyme Assays for Specificity Determination

The ability of compounds of this invention to act as a selective inhibitor of thrombin catalytic activity was assessed by determining the concentration of test compound which inhibited the activity of this enzyme by 50%, ($IC_{50}$), and comparing this value to that determined for some or all of the following related serine proteases: recombinant tissue plasminogen activator (rt-PA), plasmin, activated protein C (aPC), chymotrypsin and trypsin.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_o$ (uninhibited velocity) measurement), and 50 microliters of the enzyme diluted in HBSA. Following a 30-minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

1. Thrombin (fIIa) Assay

Enzyme activity was determined using the chromogenic substrate, Pefachrome t-PA ($CH_3SO_2$-D-hexahydrotyrosine-glycyl-L-Arginine-p-nitroanilide, obtained from Pentapharm Ltd.). The substrate was reconstituted in deionized water prior to use. Purified human a-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range) were combined in appropriate wells and incubated for 30 minutes at room temperature prior to the addition of substrate Pefachrome-t-PA (50 gl) (the final substrate concentration is 250 μM, about 5 times Km. The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

2. Recombinant Tissue Plasminogen Activator (rt-PA)

rt-PA catalytic activity was determined using the substrate, Pefachrome t-PA ($CH_3SO_2$-D-hexahydrotyrosine-glycyl-L-arginine-p-nitroanilide), obtained from Pentapharm Ltd.). The substrate was made up in deionized water followed by dilution in HBSA prior to the assay in which the final concentration was 500 micromolar (about 3-times Km).

Human rt-PA (Activase®) was obtained from Genentech Inc. The enzyme was reconstituted in deionized water and diluted into HBSA prior to the assay in which the final concentration was 1.0 nM.

3. Plasmin Assay

Plasmin catalytic activity was determined using the chromogenic substrate, S-2366 (L-pyro-Glu-Pro-Arg-pNa.HCl), which was obtained from DiaPharma Group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

4. Activated Protein C (aPC)

aPC catalytic activity was determined using the chromogenic substrate, Pefachrome PC (delta-carbobenzloxy-D-lysine-L-prolyl-L-arginine-p-nitroanilide), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

5. Chymotrypsin

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic a-chymotrypsin was obtained from Worthington Biochemical Corp. The enzyme was reconstituted in deionized water and diluted into HBSA prior to assay in which the final concentration was 0.5 nM.

6. Trypsin

Trypsin catalytic activity was determined using the chromogenic substrate, S-2222 (benzoyl-L-isoleucine-L-glutamic acid-(gamma-methyl ester)-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

7. Factor Xa

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)]. The enzyme was diluted into HBSA prior to assay, in which the final concentration was 0.25 nM.

Table 2 lists the determined $IC_{50}$ values for the compounds of Examples 11 and 14 as inhibitors of some of the enzymes listed above and demonstrates the high degree of specificity for the inhibition of alpha-thrombin compared to these related serine proteases.

TABLE 2

IC$_{50}$ values for the inhibition of human alpha thrombin amidolytic activity compared to selected serine proteases for compounds of Example 11 and 14

| Enzyme | Compound of Example 11 IC$_{50}$ (nM) | Compound of Example 14 IC$_{50}$ (nM) |
| --- | --- | --- |
| alpha-thrombin | 3.19 | 1.44 |
| rt-PA | NI* | NI* |
| Plasmin | NI* | NI* |
| aPC | NI* | NI* |
| Chymotrypsin | NI* | NI* |
| Trypsin | 1145 | 1810 |

*-No inhibition observed at the maximal concentration of inhibitor assayed-2500 nM.

Example C
Ex Vivo Anticoagulant Effects of Compounds in Rat and Human Plasma

The ex vivo anticoagulant effects of compounds of the present invention are determined by measuring the prolongation of the activated partial thromboplastin time (APTT) over a broad concentration range of the added inhibitor, using pooled normal human and rat plasma.

Fresh frozen citrated pooled normal human plasma is obtained from George King Biomedical, Overland Park, Kans. Pooled normal rat plasma is prepared from citrated whole blood collected from anesthetized rats using standard procedures. The plasma is flash frozen and stored at −80° C until use.

Measurements of APTT are made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay is conducted by making a series of dilutions of the test compounds into 100 µl rapidly thawed plasma followed by adding 200 microliters of APTT reagent and calcium chloride to the wells of the assay carousel. Compounds that prolong the APTT in a dose-dependent manner are considered to demonstrate an anticoagulant effect.

Example D
Evaluation of the Antithrombotic Potential of Compounds in an Experimental Rat Model of Thrombosis The antithrombotic (prevention of thrombus formation) properties of compounds of the present invention are evaluated using the following established experimental model of acute vascular thrombosis which is a rat model of FeCl$_3$-induced platelet-dependent arterial thrombosis.

This is a well characterized model of platelet dependent, arterial thrombosis which has been used in the evaluation potential antithrombotic compounds such as direct thrombin inhibitors. See, Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of FeCl$_3$ absorbed to a piece of filter paper. The FeCl$_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl$_3$ is monitored by ultrasonic flowtometry and is used as the primary end point. The use of flowtometry to measure carotid artery blood flow, is a modification of the original procedure in which thermal detection of clot formation was employed. See, Kurz, K. D., Main, B. W., and Sandusky, G. E., Thromb. Res., 60: 269–280 (1990).

Male Harlan Sprague Dawley rats (420–450 g) are acclimated at least 72 hours prior to use and fasted for 12 hours prior to surgery with free access to water. The animals are prepared, anesthetized with Nembutal followed by the insertion of catheters for blood pressure monitoring, drug and anesthesia delivery. The left carotid artery is isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals are randomized in either a control (saline) or treatment group with test compound, with at least 6 animals per group per dose. The test compound is administered as a single intravenous bolus at doses of about 0.3 to 5.0 mg/kg after placement of the flow probe and 5 minutes prior to the thrombogenic stimulus. At t=0, a 3 mm diameter piece of filter paper (Whatman #3) soaked with 10 microliters of a 35% solution of fresh FeCl$_3$ (made up in water) is applied the segment of isolated carotid artery distal to the flow probe. Blood pressure, blood flow, heart rate, and respiration are monitored for 60 minutes.

The incidence of occlusion (defined as the attainment of zero blood flow) is recorded as the primary end point. The efficacy of test compounds as an antithrombotic agent in preventing thrombus formation in this in vivo model is demonstrated by the reduction in the incidence of thrombotic occlusion. The effective dose which prevents 50% of thrombotic occlusions in this model (ED$_{50}$) can be determined from the above data by plotting the incidence of occlusion versus the dose administered. This allows a direct comparison of the antithrombotic efficacy of test compounds with other antithrombotic agents which have also been evaluated in this model as . Table 3 lists the ED$_{50}$ values for several well known anticoagulant agents in this model (Heparin-Hirsh, J. N. Engl. J. Med., 324:1565–1574 (1992), Cairns, J. A. et. al. Chest, 102:456S–481S (1992); Argatroban-Gold, H. K. et.al., J. Am. Coll. Cardiol., 21:1039–1047 (1993); and Hirulog™-Sharma, G. V. R. K. et.al., Am. J. Cardiol., 72:1357–1360 (1993) and Lidón, R. M. et.al., Circulation, 88:1495–1501 (1993)).

TABLE 3

Efficacy of known antithrombotic agents based on ED$_{50}$ for thrombus prevention in the FeCl$_3$ model of arterial thrombosis

| Compound | ED$_{50}$[a] |
| --- | --- |
| Standard Heparin | 200 U/kg |
| Argatroban | 3.8 mg/kg |
| Hirulog ™ | 3.0 mg/kg |

[a]ED$_{50}$ is defined as the dose that prevents the incidence of complete thrombotic occlusion in 50% of animals tested.

The in vivo comparison of compounds of the present invention with the clinically effective antithrombotic agents Standard Heparin, Argatroban, and Hirulog™ in the same rodent model of experimental thrombosis coupled with demonstrated anticoagulant effects of the present compounds in both rat and human plasma described above in Example C would lead one skilled in the art to conclude that this compound will be an effective antithrombotic agent in humans.

Example E

Elastase Assay

Elastase catalytic activity was determined using the chromogenic substrate Elastase Substrate I (MeOSuc-Ala-Ala-Pro-Val-p-nitroanaline, obtianed from Calbiochem). The substreate was reconstituted with 10% DMSO and assay buffer. Hueman Neutrophil Elastase was obtained from Calbiochem and diluted in the assay buffer prior to use. The assay buffer was HBS (10 mM HEPES, 150 mM sodium chloride, pH 7.5) with 0.1% Tween 80 and 10% DMSO. The DMSO is necessary to keep the substrate from precipitation during the course of the assay.

$IC_{50}$ determinations were conducted by combining in appropriate wells of a Corning microtiter plate, 50 microliters of the test compound at a specified concentration (covering a broad concentration range) diluted in buffer (or buffer alone for $V_o$ (uninhibited velocity) measurement), and 50 microliters of the enzyme diluted in buffer, yielding an enzyme concentration of 1 nM. Following a 30 minute incubation at ambient temperature, 100 microliters of the substrate were added to the wells, yielding a final volume of 200 microliters, and a substrate concentration of 750 µM (about 6 times Km).

The initial velocity of subtrate hydrolysis was measured by the change of absorbance at 405 nM using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

We claim:

1. A compound of the formula:

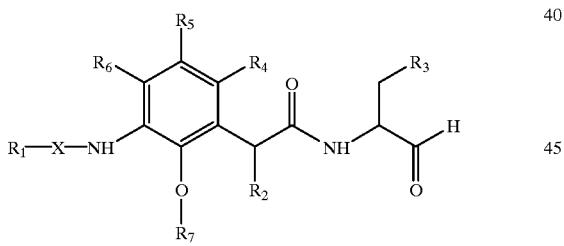

wherein (a) X is selected from the group consisting of —S(O)$_2$—, —N(R')—S(O)$_2$—, —C(=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is —NHR', —OR', —R', or —SR';

(b) R$_1$ is selected from the group consisting of:
(1) alkyl of 1 to about 12 carbon atoms,
(2) alkyl of 1 to about 3 carbon atoms substituted with cycloalkyl of about 5 to about 8 carbon atoms, which optionally is substituted on the ring carbons with hydroxyl, amino, guanidino, amidino, $C_1$ to $C_3$ alkyl, $C_1$ to $C_3$ alkoxy, or —CO$_2$R',
(3) cycloalkyl of 3 to about 15 carbon atoms, which optionally is substituted on the ring carbons with hydroxyl, amino, guanidino, amidino, $C_1$ to $C_3$ alkyl, $C_1$ to $C_3$ alkoxy, or —CO$_2$R',
(4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, and which is optionally substituted on the ring carbons with hydroxyl, amino, guanidino, amidino, $C_1$ to $C_3$ alkyl, $C_1$ to $C_3$ alkoxy, or —CO$_2$R',
(5) heterocyclo of 4 to about 10 ring atoms with the ring atoms selected from carbon and heteroatoms, wherein the heteroatoms are selected from the group consisting of oxygen, nitrogen, and $S(O)_i$, and which is optionally substituted on the ring carbons with hydroxyl, amino, guanidino, amidino, $C_1$ to $C_3$ alkyl, $C_1$ to $C_3$ alkoxy, or —CO$_2$R',
(6) alkenyl of 2 to about 6 carbon atoms which is optionally substituted with cycloalkyl of about 3 to about 8 carbon atoms, which optionally is substituted on the ring carbons with hydroxyl, amino, guanidino, amidino, $C_1$ to $C_3$ alkyl, $C_1$ to $C_3$ alkoxy, or —CO$_2$R',
(7) aryl of about 6 to about 14 carbon atoms which is optionally mono-, di- or tri-substituted with $Y_1$, $Y_2$, and/or $Y_3$,
(8) heteroaryl of 5 to 14 ring atoms with the ring atoms selected from carbon and heteroatoms, wherein the heteroatoms are selected from oxygen, nitrogen, and $S(O)_i$, and which is optionally mono-, di- or tri-substituted on the ring carbons with $Y_1$, $Y_2$, and/or $Y_3$,
(9) aralkyl of about 7 to about 15 carbon atoms which is optionally substituted on the alkyl chain with hydroxy or halogen and which is optionally mono-, di-, or tri-substituted on the aryl ring with $Y_1$, $Y_2$, and/or $Y_3$,
(10) heteroaralkyl of 5 to 14 ring atoms with the ring atoms selected from carbon and heteroatoms, wherein the heteroatoms are selected from oxygen, nitrogen, and $S(O)_i$, which is optionally substituted on the alkyl chain with hydroxy or halogen and which is optionally mono-, di- or tri-substituted on the ring carbons with $Y_1$, $Y_2$, and/or $Y_3$,
(11) aralkenyl of about 8 to about 16 carbon atoms having 6 to about 14 ring atoms which is optionally mono-, di-, or tri-substituted on the aryl ring with $Y_1$, $Y_2$, and/or $Y_3$,
(12) heteroaralkenyl of 5 to 14 ring atoms with the ring atoms selected from carbon and heteroatoms, wherein the heteroatoms are selected from oxygen, nitrogen, and $S(O)_i$, and which is optionally mono-, di- or tri-substituted on the ring carbons with $Y_1$, $Y_2$, and/or $Y_3$, (13)

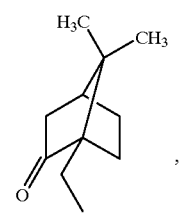

-continued

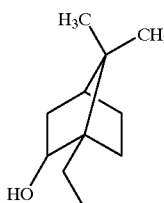
(14)

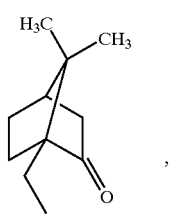
(15)

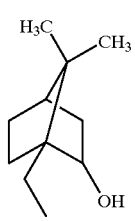
(16)

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and
(21)

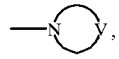

wherein

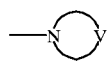

is a 5 to 7 membered heterocyclic ring having 3 to 6 ring carbon atoms, where V is —CH$_2$—, —O—, —S(=O)—, —S(O)$_2$— or —S—, and wherein Y$_1$, Y$_2$, and Y$_3$ are
(i) independently selected from the group consisting of hydrogen, halogen, cyano, nitro, tetrazolyl, amino, guanidino, amidino, methylamino, methylguanidino, —CF$_3$, —CF$_2$CF$_3$, —CF$_2$H, —CH(CF$_3$)$_2$, —C(OH)(CF$_3$)$_2$, —OCF$_3$, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NZ$_1$Z$_2$, —C(O)OH, —C(O)NH$_2$, —C(O)NHZ$_1$, —C(O)NZ$_1$Z$_2$, —C(O)OZ$_1$, —P(O)$_3$H, —P(O)$_3$H$_2$, —PH(O)OH, —P(O)$_3$(Z$_1$)$_2$, —S(O)$_3$H, —S(O)$_m$Z$_1$, —Z$_1$, —OZ$_1$, —OH, —NH$_2$, —NHZ$_1$, and —NZ$_1$Z$_2$, wherein m is 0, 1 or 2, and Z$_1$ and Z$_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) Y$_1$ and Y$_2$ are selected together to be —OC[(Z$_3$)(Z$_4$)]$_q$O—, wherein q is an integer from 1 to 4 and Z$_3$ and Z$_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms,
(c) R$_2$ is selected from the group consisting of hydrogen, alkyl of 1 to about 4 carbon atoms, and alkenyl of about 2 to about 4 carbon atoms,
(d) R$_3$ is selected from the group consisting of

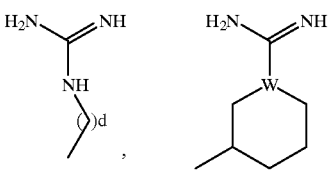

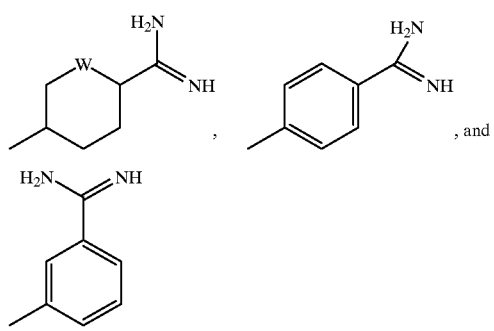

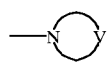

where d is an integer from 0 to 5 and W is —N— or —CH—;
(e) R$_4$ is selected from the group consisting of
(i) —R$_1$, —OR1, —NHR$_1$, —S(O)$_n$R$_1$, wherein n is 0, 1 or 2, and R$_1$ is a defined above, with the proviso that R$_1$ is not a camphor derivative or

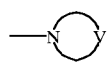

heterocycle,
(ii) —CF$_3$, —CF$_2$H, —OCF$_3$, or —OCF$_2$H,
(iii) halogen,
(iv) alkyl of 1 to 6 carbon atoms substituted with Z$_5$, wherein Z$_5$ is selected from the group consisting of hydrogen, —OH, —OR$_8$, —CH$_3$, halogen, —C(O)OH, —C(O)OR$_8$ and —S(O)$_p$R$_8$, wherein R$_8$ is alkyl of 1 to about 6 carbon atoms, and p is 0, 1 or 2,
(v) alkyl of 1 to 3 carbon atoms substituted with cycloalkyl of 3 to 5 carbon atoms,
(vi) alkenyl of about 3 to about 6 carbon atoms,
(vii) cycloalkyl of about 3 to about 10 carbon atoms,
(viii) heteroaryl of about 5 to about 10 ring atoms having 1 to about 9 ring carbon atoms and the remainder of the ring atoms heteroatoms selected from oxygen, sulfur and nitrogen, and (xi) heteroaralkyl of about 5 to about 10 ring atoms having 2 to about 15 carbon atoms which include 1 to about 9 ring carbon atoms and the remainder of the ring atoms heteroatoms selected from oxygen, sulfur and nitrogen;

(f) $R_5$ is selected from the group consisting of
  (i) $-R_1$, $-OR_1$, $-NHR_1$, $-S(O)_nR_1$, wherein $R_1$ is as defined above, with the proviso that RI is not a camphor derivative or

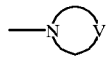

heterocycle,
  (ii) $-CF_3$, $-CF_2H$, $-OCF_3$, or $OCF_2H$, and
  (iii) halogen;

(g) $R_6$ is selected from the group consisting of
  (i) $-R_1$, $-OR_1$, $-NHR_1$, or $-S(O)_nR_1$, wherein $R_1$ is as defined above, with the proviso that $R_1$ is not a camphor derivative or

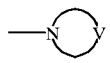

heterocycle,
  (ii) $-CF_3$, $-CF_2H$, $-OCF_3$, or $-OCF_2H$,
  (iii) halogen,
  (iv) alkyl of 1 to about 12 carbon atoms substituted with $Z_6$, wherein $Z_6$ is selected from the group consisting of hydrogen, hydroxy, halogen, $-OR_9$, $-NHR_9$, $-C(O)OH$, $-C(O)OR_9$, and $-S(O)_pR_9$, wherein $R_9$ is alkyl of 1 to about 12 carbon atoms, aryl of about 6 to about 10 carbon atoms, aralkyl of about 7 to about 12 carbon atoms, heteroaryl of about 5 to about 10 ring atoms having 1 to about 9 ring carbon atoms and the remainder of the ring atoms heteroatoms selected from oxygen, sulfur and nitrogen, which is optionally mono-, di- or tri-substituted on the ring with $Y_1$, $Y_2$ and/or $Y_3$, or heteroaralkyl of about 5 to about 10 ring atoms having about 2 to about 15 carbon atoms which include 1 to about 9 ring carbon atoms and the remainder of the ring atoms heteroatoms selected from oxygen, sulfur and nitrogen, which is optionally mono-, di- or tri-substituted on the ring with $Y_1$, $Y_2$ and/or $Y_3$,
  (v) alkyl of 1 to about 3 carbon atoms substituted with cycloalkyl of about 3 to about 8 carbon atoms,
  (vi) alkenyl of 2 to about 6 carbon atoms which is optionally substituted with cycloalkyl of about 3 to about 8 carbon atoms, aryl of about 6 to about 10 carbon atoms or heteroaryl of about 5 to about 10 ring atoms having 1 to about 9 ring carbon atoms,
  (vii) aralkyl of about 7 to about 15 carbon atoms which is optionally substituted on the alkyl chain with hydroxy or halogen, and optionally mono-, di- or tri-substituted on the aryl ring with $Y_1$, $Y_2$ and/or $Y_3$,
  (viii) heteroaralkyl of about 5 to about 10 ring atoms having 1 to about 9 ring carbon atoms and the remainder of the ring atoms heteroatoms selected from oxygen, sulfur and nitrogen, which is optionally substituted on the alkyl chain with hydroxy or halogen, and optionally mono-, di- or tri-substituted on the ring carbons with $Y_1$, $Y_2$ and/or $Y_3$,
  (ix) aralkenyl of about 6 to 15 carbon atoms which is optionally mono-, di- or tri-substituted on the aryl ring with $Y_1$, $Y_2$ and/or $Y_3$, and
  (x) heteroaralkenyl of about 5 to about 10 ring atoms having 1 to 9 ring carbon atoms and the remainder of the ring atoms heteroatoms selected from oxygen, sulfur and nitrogen, which is optionally mono-, di- or tri-substituted on the ring carbons with $Y_1$, $Y_2$ and/or $Y_3$; and (h) $R_7$ is selected from the group consisting of
  (i) $R_1$, wherein $R_1$ is as defined above with the proviso that $R_1$ is not an camphor derivative or

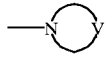

heterocycle,
  (ii) $-CF_3$ or $CF_2H$,
  (iii) alkyl of 1 to about 10 carbon atoms, optionally substituted with $-CH_2OR_{10}$, $-CO_2R_{10}$, $-SO_2R_{10}$, or $-CONR_{10}R_{11}$, wherein each of $R_{10}$ and $R_{11}$ is independnetly selected and is alkyl of 1 to about 4 carbon atoms or hydrogen,
  (iv) alkenyl of about 3 to about 10 carbon atoms, optionally substituted with $-CH_2OR_{10}$, $-CO_2R_{10}$, $-SO_2R_{10}$, or $-CONR_{10}R_{11}$,
  (v) cycloalkyl of 3 to about 10 carbon atoms, optionally substituted with $-CH_2OR_{10}$, $-CO_2R_{10}$, $-SO_2R_{10}$, or $-CONR_{10}R_{11}$,
  (vi) heteroaryl of about 5 to about 10 ring atoms having about 1 to about 9 ring carbon atoms, optionally substituted with $-CH_2OR_{10}$, $-CO_2R_{10}$, $-SO_2R_{10}$, or $-CONR_{10}R_{11}$, and
  (vii) alkyl of 1 to about 3 carbon atoms substituted with heteroaryl of about 5 to about 10 ring atoms having about 1 to about 9 carbon atoms, optionally substituted with $-CH_2OR_{10}$, $-CO_2R_{10}$, $-SO_2R_{10}$, or $-CONR_{10}R_{11}$, or pharmaceutically acceptable salts thereof.

2. A compound according to claim 1, wherein X is selected from the group consisting of a direct link, $-SO_2-$, and $-NH-S(O)_2-$.

3. A compound according to claim 2, wherein X is $-SO_2-$.

4. A compound according to claim 1, wherein $R_1$ is selected from the group consisting of alkyl, aralkyl, and aryl.

5. A compound according to claim 4, wherein $R_1$ is aralkyl selected from substituted benzyl and unsubstituted benzyl, or is aryl selected from substituted phenyl, unsubstituted phenyl, substituted naphthyl and unsubstituted naphthyl.

6. A compound according to claim 5, wherein $R_1$ is aryl substituted with a group selected from the group consisting of methyl, methoxy, fluoro, chloro, trifluoromethyl, and $-OCF_3$.

7. A compound according to claim 5, wherein $R_1$ is cyclohexyl or cyclohexylmethyl.

8. A compound according to claim 4, wherein $R_1$ is aralkyl.

9. A compound according to claim 1, wherein $R_2$ is hydrogen.

10. A compound according to claim 1, wherein $R_3$ is

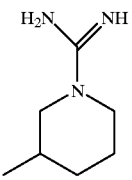

11. A compound according to claim 1, wherein $R_4$ is selected from the group consisting of:
(a) hydrogen,
(b) alkyl of 1 to 6 carbon atoms substituted with $Z_5$, wherein $Z_5$ is selected from the group consisting of hydrogen, —OH, —$OR_8$, —$CH_3$, halogen, —C(O)OH, —C(O)$OR_8$, —S(O)$_3$OH and —S(O)$_p R_8$,
(c) alkyl of 1 to 3 carbon atoms substituted with cyclic alkyl of 3 to 5 carbon atoms,
(d) alkenyl,
(e) cycloalkyl,
(f) heteroaryl,
(g) heteroaralkyl, and
(h) trifluoromethyl.

12. A compound according to claim 11, wherein $R_4$ is selected from the group consisting of methyl, ethyl, propenyl, allyl, propyl, isopropyl, butyl, (R)-sec-butyl, (S)-sec-butyl, isobutyl, 1-pentyl, (R)-2-pentyl, (S)-2-pentyl, 3-pentyl, (S)-1-(2-methyl)-butyl, (R)-2-(3-methyl)-butyl, 1-(3-methyl)-butyl, (R)-1-(2-methyl)-butyl, cyclopentyl, 2-pyrrolyl, 3-pyrrolyl, 1-hexyl, (S)-2-hexyl, (R)-2-hexyl, (R)-3-hexyl, (S)-3-hexyl, hydroxy, —$OR_8$, wherein $R_8$ is alkyl of 1 to about 4 carbon atoms, phenyloxy, —$OCF_3$, and halogen.

13. A compound according to claim 1, wherein $R_5$ is selected from the group consisting of hydrogen, halogen, alkyl of 1 to about 5 carbon atoms, trifluoromethyl, alkoxy of 1 to about 4 carbon atoms.

14. A compound according to claim 13, wherein $R_5$ is hydrogen.

15. A compound according to claim 1, wherein $R_6$ is selected from the group consisting of:
(a) hydrogen,
(b) alkyl of 1 to about 12 carbon atoms substituted with $Z_6$,
(c) alkyl of 1 to about 3 carbon atoms substituted with cycloalkyl,
(d) alkenyl of about 2 to about 6 carbon atoms which is optionally substituted with cycloalkyl,
(e) aralkyl of about 7 to about 15 carbon atoms which is optionally substituted on the alkyl chain with hydroxy or halogen, and optionally mono-, di- or tri-substituted with $Y_1$, $Y_2$ and/or $Y_3$,
(f) heteroaralkyl ring of about 5 to about 10 ring atoms having 1 to about 9 ring carbon atoms and the remainder of the ring atoms heteroatoms selected from oxygen, sulfur and nitrogen, which is optionally substituted on the alkyl chain with hydroxy or halogen, and optionally mono-, di- or tri-substituted with $Y_1$, $Y_2$ and/or $Y_3$,
(g) aralkenyl of about 6 to 15 carbon atoms which is optionally mono-, di- or tri-substituted on the aryl ring with $Y_1$, $Y_2$ and/or $Y_3$, and,
(h) heteroaralkenyl of about 5 to about 10 ring atoms having 1 to 9 ring carbon atoms and the remainder of the ring atoms heteroatoms selected from oxygen, sulfur and nitrogen, which is optionally mono-, di- or tri-substituted with $Y_1$, $Y_2$ and/or $Y_3$.

16. A compound according to claim 1, wherein $R_4$ and $R_5$ are independently selected from the group consisting of hydrogen and methyl and $R_6$ is selected from the group consisting of aralkyl of about 8 to about 13 carbon atoms, —O—-aralkyl, —NH-aralkyl, and —S(O)$_p$-aralkyl of about 7 to about 12 carbon atoms.

17. A compound according to claim 16, wherein said aralkyl group has an aryl group selected from unsubstituted phenyl, substituted phenyl, substituted naphthyl and unsubstituted naphthyl.

18. A compound according to claim 17, wherein said aryl group is substituted with a substituent selected from the group consisting of methyl, methoxy, fluoro, chloro and trifluoromethyl.

19. A compound according to claim 15, wherein $R_6$ is selected from the group consisting of phenylethyl, phenylpropyl, cyclohexylethyl and cyclohexylpropyl.

20. A compound according to claim 1, wherein $R_7$ is selected from the group consisting of hydrogen, methyl, difluoromethyl and trifluoromethyl.

21. A compound according to claim 20, wherein $R_7$ is hydrogen or methyl.

22. A compound according to claim 1, wherein $R_7$ is selected from the group consisting of:
(a) alkyl of 1 to about 10 carbon atoms, optionally substituted with —$CH_2 OR_{10}$, —$CO_2 R_{10}$, —$SO_2 R_{10}$, or —$CONR_{10} R_{11}$,
(b) alkenyl of about 3 to about 10 carbon atoms, optionally substituted with —$CH_2 OR_{10}$, —$CO_2 R_{10}$, —$SO_2 R_{10}$, or —$CONR_{10} R_{11}$,
(c) cycloalkyl of 3 to about 10 carbon atoms, optionally substituted with —$CH_2 OR_{10}$, —$CO_2 R_{10}$, —$SO_2 R_{10}$, or —$CONR_{10} R_{11}$,
(d) heteroaryl of about 5 to about 10 ring atoms having about 1 to about 9 ring carbon atoms, optionally substituted with —$CH_2 OR_{10}$, —$CO_2 R_{10}$, —$SO_2 R_{10}$, or —$CONR_{10} R_{11}$, and
(e) alkyl of 1 to about 3 carbon atoms substituted with heteroaryl of about 5 to about 10 ring atoms having about 1 to about 9 carbon atoms, optionally substituted with —$CH_2 OR_{10}$, —$CO_2 R_{10}$, —$SO_2 R_{10}$, and —$CONR_{10} R_{11}$.

23. A compound according to claim 1, wherein $R_5$ and $R_6$ are independently selected from hydrogen and methyl, and $R_4$ is selected from the group consisting of hydrogen, methyl, ethyl, propenyl, allyl, propyl, isopropyl, butyl, (R)-sec-butyl, (S)-sec-butyl, isobutyl, 1-pentyl, (R)-2-pentyl, (S)-2-pentyl, 3-pentyl, (S)-1-(2-methyl)-butyl, (R)-2-(3-methyl)-butyl, 1-(3-methyl)-butyl, (R)-1-(2-methyl)-butyl, cyclopentyl, 1-hexyl, (S)-2-hexyl, (R)-2-hexyl, (R)-3-hexyl, and (S)-3-hexyl.

24. A compound according to claim 1, wherein $R_4$, $R_5$, and $R_6$, are independently selected from hydrogen and methyl.

25. A compound according to claim 1, wherein any two of $R_2$, $R_4$, $R_5$, and $R_6$ are hydrogen.

26. A compound according to claim 1, wherein X is —S(O)$_2$—, $R_1$ is substituted or unsubstituted aralkyl, and $R_3$ is

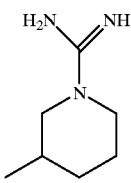

27. A compound according to claim 26, wherein $R_1$ is substituted or unsubstituted benzyl.

28. A compound of the formula:

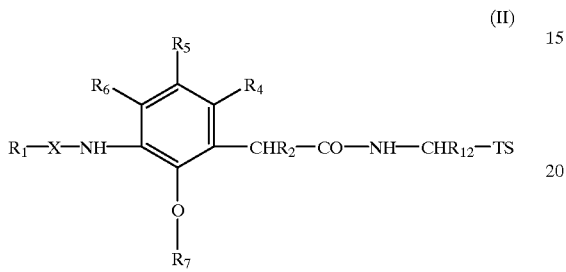

(II)

wherein,
(a) X is selected from the group consisting of —S(O)$_2$—, —N(R')—S(O)$_2$—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is —NR', —OR', —R', or —SR';
(b) $R_1$ is selected from the group consisting of:
(1) alkyl of 1 to about 12 carbon atoms,
(2) alkyl of 1 to about 3 carbon atoms substituted with cycloalkyl of about 5 to about 8 carbon atoms, which optionally is substituted in the ring carbons with hydroxyl, amino, guanidino, amidino, $C_1$ to $C_3$ alkyl, $C_1$ to $C_3$ alkoxy, or $CO_2R'$,
(3) cycloalkyl of 3 to about 15 carbon atoms, which optionally is substituted in the ring carbons with hydroxyl, amino, guanidino, amidino, $C_1$ to $C_3$ alkyl, $C_1$ to $C_3$ alkoxy, or $CO_2R'$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, and which is optionally substituted on the ring carbons with hydroxyl, amino, guanidino, amidino, $C_1$ to $C_3$ alkyl, $C_1$ to $C_3$ alkoxy, or $CO_2R'$,
(5) heterocyclo of 4 to about 10 ring atoms with the ring atoms selected from carbon and heteroatoms, wherein the heteroatoms are selected from the group consisting of oxygen, nitrogen, and S(O)$_i$, and which is optionally substituted on the ring carbons with hydroxyl, amino, guanidino, amidino, $C_1$ to $C_3$ alkyl, $C_1$ to $C_3$ alkoxy, or $CO_2R'$,
(6) alkenyl of about 2 to about 6 carbon atoms which is optionally substituted with cycloalkyl of about 3 to about 8 carbon atoms, which optionally is substituted on the ring carbons with hydroxyl, amino, guanidino, amidino, $C_1$ to $C_3$ alkyl, $C_1$ to $C_3$ alkoxy, or $CO_2R'$,
(7) aryl of about 6 to about 14 carbon atoms which is optionally mono-, di- or tri-substituted with $Y_1$, $Y_2$, and/or $Y_3$,
(8) heteroaryl of 5 to 14 ring atoms with the ring atoms selected from carbon and heteroatoms, wherein the heteroatoms are selected from oxygen, nitrogen, and S(O)$_i$, and which is optionally mono-, di- or tri-substituted on the ring carbons with $Y_1$, $Y_2$, and/or $Y_3$,
(9) aralkyl of about 7 to about 15 carbon atoms which is optionally substituted on the alkyl chain with hydroxy or halogen and which is optionally mono-, di-, or tri-substituted on the aryl ring with $Y_1$, $Y_2$, and/or $Y_3$,
(10) heteroaralkyl of 5 to 14 ring atoms with the ring atoms selected from carbon and heteroatoms, wherein the heteroatoms are selected from oxygen, nitrogen, and S(O)$_i$, which is optionally substituted on the alkyl chain with hydroxy or halogen and which is optionally mono-, di- or tri-substituted on the ring carbons with $Y_1$, $Y_2$, and/or $Y_3$, respectively,
(11) aralkenyl of about 8 to about 16 carbon atoms having 6 to about 14 ring atoms which is optionally mono-, di-, or tri-substituted on the aryl ring with $Y_1$, $Y_2$, and/or $Y_3$, respectively,
(12) heteroaralkenyl of 5 to 14 ring atoms with the ring atoms selected from carbon and heteroatoms, wherein the heteroatoms are selected from oxygen, nitrogen, and S(O)$_i$, and which is optionally mono-, di- or tri-substituted on the ring carbons with $Y_1$, $Y_2$, and/or $Y_3$, respectively,

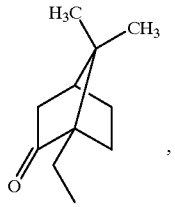

(13)

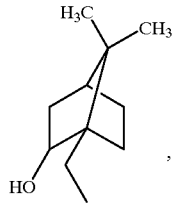

(14)

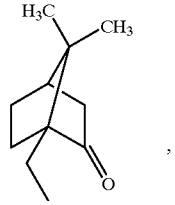

(15)

-continued (16)

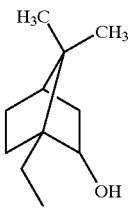
,

(17) perfluoroalkyl of 1 to about 12 carbon atoms,
(18) perfluoroaryl of about 6 to about 14 carbon atoms,
(19) perfluoroaryl alkyl of about 7 to about 15 carbon atoms,
(20) hydrogen, and
(21)

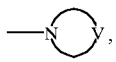, wherein

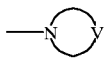

is a 5 to 7 member heterocyclic ring having 3 to 6 ring carbon atoms, where V is —$CH_2$—, —O—, —S(=O)—, —$S(O)_2$—or —S—, wherein $Y_1$, $Y_2$, and $Y_3$ are
(i) independently selected from the group consisting of hydrogen, halogen, cyano, nitro, tetrazolyl, amino, guanidino, amidino, methylamino, methylguanidino, —$CF_3$, —$CF_2CF_3$, —$CF_2H$, $CH(CF_3)_2$, —$C(OH)(CF_3)_2$, —$OCF_3$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)NZ_1Z_2$, —$C(O)OZ_1$, —$P(O)_3H$, —$P(O)_3H_2$, —$PH(O)OH$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) $Y_1$ and $Y_2$ are selected together to be —$OC[(Z_3)(Z^4)]_qO$—, wherein q is an integer from 1 to 4 and $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms;
(c) $R_2$ is selected from the group consisting of hydrogen, alkyl of 1 to about 4 carbon atoms, and alkenyl of about 2 to about 4 carbon atoms;

(d) $R_4$ is selected from the group consisting of
(i) —$R_1$, —$OR_1$, —$NHR_1$, —$S(O)_nR_1$, wherein n is 0, 1 or 2, and $R_1$ is as defined above, with the proviso that $R_1$ is not a camphor derivative or

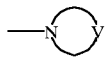

heterocycle,
(ii) —$CF_3$, —$CF_2H$, —$OCF_3$, —$OCF_2H$,
(iii) halogen,
(iv) alkyl of 1 to 6 carbon atoms substituted with $Z_5$, wherein $Z_5$ is selected from the group consisting of hydrogen, —OH, —$OR_8$, —$CH_3$, halogen, —C(O)OH, —$C(O)OR_8$ and —$S(O)_pR_8$, wherein $R_8$ is alkyl of 1 to about 6 carbon atoms, and p is 0, 1 or 2,
(v) alkyl of 1 to 3 carbon atoms substituted with cyclic alkyl of 3 to 5 carbon atoms,
(vi) alkenyl of about 3 to about 6 carbon atoms,
(vii) cycloalkyl of about 3 to about 10 carbon atoms,
(viii) heteroaryl of about 5 to about 10 ring atoms having 1 to about 9 ring carbon atoms and the remainder of the ring atoms heteroatoms selected from oxygen, sulfur and nitrogen, and
(ix) heteroaralkyl of about 5 to about 10 ring atoms having 2 to about 15 carbon atoms which include 1 to about 9 ring carbon atoms and the remainder of the ring atoms heteroatoms selected from oxygen, sulfur and nitrogen;
(e) $R_5$ is selected from the group consisting of
(i) —$R_1$, —$OR_1$, —$NHR_1$, —$S(O)_nR_1$, wherein $R_1$ is as defined above, with the proviso that $R_1$ is not a camphor derivative or

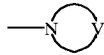

heterocycle,
(ii) —$CF_3$, —$CF_2H$, —$OCF_3$, —$OCF_2H$, and
(iii) halogen;
(f) $R_6$ is selected from the group consisting of
(i) —$R_1$, —$OR_1$, —$NHR_1$, —$S(O)_nR_1$, wherein $R_1$ is as defined above, with the proviso that $R_1$ is not a camphor derivative or

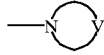

heterocycle,
(ii) —$CF_3$, —$CF_2H$, —$OCF_3$, —$OCF_2H$,
(iii) halogen,
(iv) alkyl of 1 to about 12 carbon atoms substituted with $Z_6$, wherein $Z_6$ is selected from the group consisting of hydrogen, hydroxy, halogen, —$OR_9$, —$NHR_9$, —$C(O)OH$, —$C(O)OR_9$, and —$S(O)_pR_9$, wherein $R_9$ is alkyl of 1 to about 12 carbon atoms, aryl of about 6 to about 10 carbon atoms, aralkyl of about 7 to about 12 carbon atoms, heteroaryl of about 5 to about 10 ring atoms 1 to about 9 ring carbon atoms and the remainder of the ring atoms heteroatoms selected from oxygen, sulfur and nitrogen, which is optionally mono-, di- or tri-substituted in the ring carbons with $Y_1$, $Y_2$ and/or $Y_3$, and heteroaralkyl of about 5 to about 10 ring atoms having about 2 to about 15 carbon atoms which include 1 to about 9 ring carbon atoms and the remainder of the ring atoms heteroatoms selected from oxygen, sulfur and nitrogen, which is optionally mono-, di- or tri-substituted in the ring carbons with $Y_1$, $Y_2$ and/or $Y_3$,
(v) alkyl of 1 to about 3 carbon atoms substituted with cycloalkyl of about 3 to about 8 carbon atoms,
(vi) alkenyl of 2 to about 6 carbon atoms which is optionally substituted with cycloalkyl of about 3 to about 8 carbon atoms, aryl of about 6 to about 10 carbon atoms, or heteroaryl of about 5 to about 10 ring atoms having 1 to about 9 ring carbon atoms,
(vii) aralkyl of about 7 to about 15 carbon atoms which is optionally substituted on the alkyl chain with hydroxy or halogen, and optionally mono-, di- or tri-substituted with $Y_1$, $Y_2$ and/or $Y_3$,
(viii) heteroaralkyl of about 5 to about 10 ring atoms having 1 to about 9 ring carbon atoms and the remainder of the ring atoms heteroatoms selected from oxygen, sulfur and nitrogen, which is optionally substituted on the alkyl chain with hydroxy or halogen, and optionally mono-, di- or tri-substituted on the ring with $Y_1$, $Y_2$ and/or $Y_3$,
(ix) aralkenyl of about 6 to 15 carbon atoms which is optionally mono-, di- or tri-substituted on the aryl with $Y_1$, $Y_2$ and/or $Y_3$, and
(x) heteroaralkenyl ring of about 5 to about 10 ring atoms with 1 to 9 ring carbon atoms and the remainder of the ring atoms heteroatoms selected from oxygen, sulfur and nitrogen, which is optionally mono-, di- or tri-substituted with $Y_1$, $Y_2$ and/or $Y_3$;
(g) $R_7$ is selected from the group consisting of
(i) $R_1$, wherein $R_1$ is as defined above, with the proviso that $R_7$ is not an $R_1$ camphor derivative or

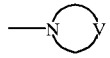

heterocycle,
(ii) —$CF_3$ or $CF_2H$,
(iii) alkyl of 1 to about 10 carbon atoms, optionally substituted with —$CH_2OR_{10}$, —$CO_2R_{10}$, —$SO_2R_{10}$, —$CONR_{10}R_{11}$, wherein each of $R_1$ and $R_{11}$ is independently selected and is alkyl of 1 to about 4 carbon atoms or hydrogen,
(iv) alkenyl of about 3 to about 10 carbon atoms, optionally substituted with —$CH_2OR_{10}$, $CO_2R_{10}$, —$SO_2R_{10}$, $CONR_{10}R_{11}$,
(v) cycloalkyl of 3 to about 10 carbon atoms, optionally substituted with —$CH_2OR_{10}$, —$CO_2R_{10}$, —$SO_2R_{10}$, —$CONR_{10}R_{11}$,
(vi) heteroaryl of about 5 to about 10 ring atoms, having about 1 to about 9 ring carbon atoms which is optionally substituted with —$CH_2OR_{10}$, $CO_2R_{10}$, —$SO_2R_{10}$, or —$CONR_{10}R_{11}$, and
(vii) alkyl of 1 to about 3 carbon atoms substituted with heteroaryl of about 5 to about 16 atoms having 1 to about 9 carbon atoms, which is optionally substituted with —$CH_2OR_{10}$, $CO_2R_{10}$, $SO_2R_{10}$, $CONR_{10}R_{11}$; and (h) $R_{12}$ is selected from the group consisting of
(i) alkyl of 1 to about 12 carbon atoms which is optionally substituted with amino, amidino or guanidino,
(ii) aralkyl of 7 to about 15 carbon atoms which is optionally substituted on a ring carbon with amino, amidino, or guanidino,
(iii) aryl of about 6 to about 14 carbon atoms which is optionally substituted on a ring carbon with amino, amidino, or guanidino,
(iv) heteroaralkyl of 5 to about 14 ring atoms having 1 to about 9 ring carbon atoms and the remainder of the ring atoms heteroatoms selected from oxygen, nitrogen and sulfur which is optionally substituted on a ring carbon with amino, amidino or guanidino; and (j) TS is selected from the group consisting of
(i) —CHO,
(ii) —$C(O)CF_3$,
(iii) —$C(O)CF_2CF_3$,
(iv) —$C(O)$—$C(O)$—$NHR_{13}$,
(v) —$C(O)$—$C(O)_2R_{13}$,
(vi) —$C(O)$—$C(O)$—$NR_{13}R_{14}$,
(vii) —$B(OR_{13})(OR_{14})$,
(viii) —$C(O)CH_2Cl$, and
(ix) —$C(O)$—$R_{15}$;

wherein $R_{13}$ and $R_{14}$ are independently selected from hydrogen lower alkyl of 1 to about 6 carbon atoms, cycloalkyl of 3 to about 10 carbon atoms, aralkyl of 7 to about 15 carbon atoms, and heteroaralkyl of about 5 to about 10 ring atoms having about 2 to about 15 carbon atoms which include 1 to about 9 ring carbon atoms and the remainder of the ring atoms heteroatoms selected from oxygen, nitrogen and sulfur; or when TS is —$B(OR_{13})(OR_{14})$ then $OR_{13}$ and $OR_{14}$ may be taken together to be —$O[C(Z_3)(Z_4)]qO$—; and $R_{15}$ is selected from aryl of 6 to about 14 carbon atoms and heteroaryl of 5 to about 14 ring atoms having 1 to about 13 ring carbon atoms and the remainder of the ring atoms selected from oxygen, nitrogen and sulfur; and pharmaceutically acceptable salts thereof.

* * * * *